(12) United States Patent
Webb et al.

(10) Patent No.: US 9,453,204 B2
(45) Date of Patent: Sep. 27, 2016

(54) PRODUCTION OF PLURIPOTENT CELLS THROUGH INHIBITION OF BRIGHT/ARID3A FUNCTION

(75) Inventors: Carol Webb, Oklahoma City, OK (US); Paul Kincade, Oklahoma City, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 1622 days.

(21) Appl. No.: 12/500,987

(22) Filed: Jul. 10, 2009

(65) Prior Publication Data

US 2010/0008891 A1 Jan. 14, 2010

Related U.S. Application Data

(60) Provisional application No. 61/080,451, filed on Jul. 14, 2008.

(51) Int. Cl.
*C12N 5/02* (2006.01)
*C12N 5/00* (2006.01)
*C12N 15/00* (2006.01)
*C12N 5/074* (2010.01)

(52) U.S. Cl.
CPC ......... *C12N 5/0696* (2013.01); *C12N 2501/60* (2013.01); *C12N 2510/00* (2013.01)

(58) Field of Classification Search
CPC .................................................. C12N 5/0696
USPC ....................................................... 435/377
See application file for complete search history.

(56) References Cited

U.S. PATENT DOCUMENTS

| | | | |
|---|---|---|---|
| 5,494,899 A | 2/1996 | Kincade et al. | 514/21 |
| 5,554,595 A | 9/1996 | Kincade et al. | 514/21 |
| 5,801,154 A | 9/1998 | Baracchini et al. | 514/44 A |
| 6,518,043 B1 | 2/2003 | Oritani et al. | 435/69.1 |
| 2003/0124128 A1 | 7/2003 | Lillie et al. | 424/155.1 |
| 2003/0165434 A1 | 9/2003 | Reinhard et al. | 424/45 |
| 2005/0271651 A1 | 12/2005 | Webb | 424/131.1 |

FOREIGN PATENT DOCUMENTS

WO    WO 2006/040615    4/2006

OTHER PUBLICATIONS

Stadtfield (2008, Cell, 2:230-240).*
Buganim (2012,Cell, 150:1209-1222.*
Hochedlinger et al. (Cell, 121: 465-477 (May 6, 2005)).*
Office Communication received in European Patent Application No. 09790275.3, dated Jul. 6, 2011.
"Appendix E: Stem Cell Markers—Appendix E.i. How do researchers use markers to identify stem cells?" Stem Cell Information: The National Institutes of Health resource for stem cell research, 2001, http://stemcells.nih.gov/info/scireport/appendixE.asp, Jun. 17, 2008.
Attwood, "The babel of bionformatics," *Science*, 290:471-3, 2000.
Branch, "A good antisense molecule is hard to find," *TIBS*, 23:45-50, 1998.
Burns and Peterson, "The yeast SWI-SNF complex facilitates binding of a transcriptional activator to nucleosomal sites in vivo," *Mol. Cell. Biol.*, 17:4811-4819, 1997.
Callery et al., "The ARID domain protein drill is necessary for TGF(beta) signaling in Xenopus embryos," *Dev. Biol.*, 278:542-59, 2005.
Dallas et al., "The human SWI-SNF complex protein p270 is an ARID family member with non-sequence-specific DNA binding activity," *Mol. Cell. Biol.*, 20:3137-3146, 2000.
Edwards and Cambridge, "Prospects for B-cell-targeted therapy in autoimmune disease," *Rheumatology*, 44:151-156, 2005.
Fattaey et al., "Characterization of the retinoblastoma binding proteins RBP1 and RBP2," *Oncogene*, 8:3149-56, 1993.
Feng et al., "Molecules that promote or enhance reprogramming of somatic cells to induced pluripotent stem cells," *Cell Stem Cell*, 4:301-12, 2009.
Flowers et al., "Antagonistic roles for BRM and BRG1 SWI/SNF complexes in differentiation," *J. Biol. Chem.*, 284:10067-75, 2009.
Fukuyo et al., "E2FBP1/hDril1 modulates cell growth through downregulation of promyelocytic leukemia bodies," *Cell Death Differ.*, 11:747-759, 2004.
Goebel et al., "High frequency of matrix attachment regions and cut-like protein x/CCAAT-displacement and B cell regulator of IgH transcription binding sites flanking Ig V region genes," *J. Immunol.*, 169(5):2477-2487, 2002.
Gray et al., "Functional characterization of JMJD2A, a histone deacetylase- and retinoblastoma-binding protein," *J. Biol. Chem.*, 280:28507-18, 2005.
Green et al., "Antisense oligonucleotides: an evolving technology for the modulation of gene expression in human disease," *J Am Coll Surg*, 191:94-105, 2000.
Gregory et al., "Characterization of the dead ringer gene identifies a novel, highly conserved family of sequence-specific DNA-binding proteins," *Mol. Cell. Biol.*, 16:792-799, 1996.
Gurdon and Melton, "Nuclear reprogramming in cells," *Science*, 322:1811-5, 2008.
Hanna et al., "Metastable pluripotent states in NOD-mouse-derived ESCs," *Cell Stem Cell*, 4:513-24, 2009.
Hanna et al., "Direct reprogramming of terminally differentiated mature B lymphocytes to pluripotency," *Cell*, 133:250-264, 2008.
Herrscher et al., "The immunoglobulin heavy-chain matrix-associating regions are bound by Bright: a B cell-specific trans-activator that describes a new DNA-binding protein family," *Genes Dev.*, 9:3067-3082, 1995.
Ho et al., "An embryonic stem cell chromatin remodeling complex, esBAF, is essential for embryonic stem cell self-renewal and pluripotency," *Proc. Natl. Acad. Sci. USA*, 106:5181-6, 2009.

(Continued)

Primary Examiner — Valarie Bertoglio
(74) Attorney, Agent, or Firm — Parker Highlander PLLC

(57) ABSTRACT

The present invention involves the identification of Bright/ARID3a as involved in the regulation of pluripotency in cells, and the targeting of that function for the regulation of pluripotency. Thus, methods of de-differentiating cells into pluripotent cells are provided, as well as methods for re-differentiating such cells in a controlled fashion.

16 Claims, 15 Drawing Sheets

(56) References Cited

OTHER PUBLICATIONS

Horsley and Fuchs, "Reprogramming somatic cells to their embryonic state," *HFSP J.*, 1:89-93, 2007.
Iarovaia et al., "Induction of transcription within chromosomal DNA loops flanked by MAR elements causes an association of loop DNA with the nuclear matrix," *Nucleic Acids Res.*, 33:4157-63, 2005.
Iwahara, and Clubb, "Solution structure of the DNA binding domain from Dead ringer, a sequence-specific AT-rich interaction domain (ARID)," *EMBO J*, 18:6084-6094, 1999.
Jen and Gewertz, "Suppression of gene expression by targeted disruption of messenger RNA: available options and current strategies," *Stem Cells*, 18:307-319, 2000.
Kaplan et al., "Transcriptional activation by a matrix associating region-binding protein. contextual requirements for the function of bright," *J. Biol. Chem.*, 276:21325-21330, 2001.
Kim and Tucker, "A regulated nucleocytoplasmic shuttle contributes to Bright's function as a transcriptional activator of immunoglobulin genes," *Mol. Cell. Biol.*, 26:2187-2201, 2006.
Kim et al., "An extended transcriptional network for pluripotency of embryonic stem cells," *Cell*, 132:1049-61, 2008.
Lewitzky and Yamanaka, "Reprogramming somatic cells towards pluripotency by defined factors," *Curr. Opin. Biotechnol.*, 18:467-473, 2007.
Lin et al., "Bright/ARID3A contributes to chromatin accessibility of the immunoglobulin heavy chain enhancer," *Mol. Cancer*, 6:23, 2007.
Liu, "iPS cells: a more critical review," *Stem Cells Dev.*, 17:391-7, 2008.
Ma et al., "E2FBP1/DRIL1, an AT-rich interaction domain-family transcription factor, is regulated by p53," *Mol. Cancer Res.*, 438-44, 2003.
Maherali and Hockedlinger, "Guidelines and techniques for the generation of induced pluripotent stem cells," *Cell Stem Cell*, 3:595-605, 2008.
Marson et al., "Wnt signaling promotes reprogramming of somatic cells to pluripotency," *Cell Stem Cell*, 3:132-5, 2008.
Meissner et al., "Direct reprogramming of genetically unmodified fibroblasts into pluripotent stem cells," *Nat. Biotechnol.*, 25:1177-81, 2007.
Mikkelsen et al., "Dissecting direct reprogramming through integrative genomic analysis," *Nature*, 454:49-55, 2008.
Mohamed et al., "Nucleocytoplasmic shuttling of Bruton's tyrosine kinase," *J. Biol. Chem.*, 275:40614-40619, 2000.
Nakagawa et al., "Generation of induced pluripotent stem cells without Myc from mouse and human fibroblasts," *Nat. Biotechnol.*, 26:101-6, 2008.
Nixon et al., "The transcription factor, Bright, is not expressed in all human B lymphocyte subpopulations," *Cell. Immunol.*, 228:42-53, 2004.
Nixon et al., "Mutations in the DNA-binding domain of the transcription factor Bright act as dominant negative proteins and interfere with immunoglobulin transactivation," *J. Biol. Chem.*, 279:52465-52472, 2004.
Nixon et al., "Transgenic mice expressing dominant-negative bright exhibit defects in B1 B cells," *J. Immunol.*, 181:6913-22, 2008.
Numata et al., "Bdp, a new member of a family of DNA-binding proteins, associates with the retinoblastoma gene product," *Cancer Res.*, 59:3741-3747, 1999.
Office Communication issued in related U.S. Appl. No. 11/040,448; dated Feb. 6, 2008.
Office Communication issued in related U.S. Appl. No. 11/040,448; dated Jul. 3, 2008.
Office Communication issued in related U.S. Appl. No. 11/040,448; dated May 12, 2009.
Office Communication issued in related U.S. Appl. No. 11/040,448; dated Aug. 12, 2009.
Peeper et al., "A functional screen identifies hDRIL1 as an oncogene that rescues RAS-induced senescence," *Nat. Cell. Biol.*, 4:148-53, 2002.
Pei, "Regulation of pluripotency and reprogramming by transcription factors," *J. Biol. Chem.*, 284:3365-9, 2009.
Pereira et al., "Heterokaryon-based reprogramming of human B lymphocytes for pluripotency requires Oct4 but not Sox2," *PLoS Genet.*, 4:e1000170, 2008.
Peterson and Herskowitz, "Characterization of the yeast SWI1, SWI2, and SWI3 genes, which encode a global activator of transcription," *Cell*, 68:573-583, 1992.
Rajaiya et al., "Bruton's tyrosine kinase regulates immunoglobulin promoter activation in association with the transcription factor Bright," *Mol. Cell. Biol.*, 25:2073-2084, 2005.
Rajaiya et al., "Induction of immunoglobulin heavy-chain transcription through the transcription factor Bright requires TFII-I," *Mol. Cell. Biol.*, 26:4758-4768, 2006.
Shandala et al., "The Drosophila dead ringer gene is required for early embryonic patterning through regulation of argos and buttonhead expression," *Development*, 126:4341-9, 1999.
Shankar et al., "Anti-nuclear antibody production and autoimmunity in transgenic mice that overexpress the transcription factor Bright," *J. Immunol.*, 178:2996-3006, 2007.
Shih et al., "Human embryonic stem cells are prone to generate primitive, undifferentiated tumors in engrafted human fetal tissues in severe combined immunodeficient mice," *Stem Cells Dev.*, 16:893-902, 2007.
Skolnick and Fetrow, "From genes to protein structure and function: novel applications of computational approaches in the genomic era," *Trends in Biotech.*, 18:34-9, 2000.
Suzuki et al., "A novel E2F binding protein with Myc-type HLH motif stimulates E2F-dependent transcription by forming a heterodimer," *Oncogene*, 17:853-865, 1998.
Takahashi et al., "Induction of pluripotent stem cells from adult human fibroblasts by defined factors," *Cell*, 131:1-12, 2007.
Takahashi and Yamanaka, "Induction of pluripotent stem cells from mouse embryonic and adult fibroblast cultures by defined factors," *Cell*, 126:663-76, 2006.
Taylor et al. "Antisense oligonucleotides: a systematic high-throughput approach to target validation and gene function determination," *DDT*, 4(12):562-567, 1999.
Torchilin, "Tat peptide-modified liposomes for intracellular delivery of drugs and DNA," *Cell. Mol. Biol. Lett.*, 7:265-7, 2002.
Treisman et al., "eyelid antagonizes wingless signaling during *Drosophila* development and has homology to the Bright family of DNA-binding proteins," *Genes Dev.*, 11:1949-62, 1997.
Tu et al., "The ARID domain of the H3K4 demethylase RBP2 binds to a DNA CCGCCC motif," *Nat. Struct. Mol. Biol.*, 15:419-21, 2008.
Wang et al., "Cux/CDP homeoprotein is a component of NF-muNR and represses the immunoglobulin heavy chain intronic enhancer by antagonizing the bright transcription activator," *Mol. Cell. Biol.*, 19:284-295, 1999.
Wang et al., "A protein interaction network for pluripotency of embryonic stem cells," *Nature*, 444:364-8, 2006.
Webb et al., "A topoisomerase II-like protein is part of an inducible DNA-binding protein complex that binds 5' of an immunoglobulin promoter," *Nucleic Acids Res.*, 21:4363-68, 1993.
Webb et al., "Differential regulation of immunoglobulin gene transcription via nuclear matrix-associated regions," *Cold Spring Harbor Symp.Quant.Biol.*, LXIV, 64:109-18, 1999.
Webb et al., "Expression of bright at two distinct stages of B lymphocyte development," *J. Immunol.*, 160:4747-54, 1998.
Webb et al., "Identification of a matrix-associated region 5' of an immunoglobulin heavy chain variable region gene," *Mol. Cell. Biol.*, 11:5206-5211, 1991.
Webb et al., "Induction of immunoglobulin mu mRNA in a B cell transfectant stimulated with interleukin-5 and a T-dependent antigen," *J. Immunol.*, 143:3934-39, 1989.
Webb et al., "Novel protein-DNA interactions associated with increased immunoglobulin transcription in response to antigen plus interleukin-5," *Mol. Cell. Biol.*, 11:5197-5205, 1991.

(56) References Cited

OTHER PUBLICATIONS

Webb et al., "The transcription factor Bright associates with Bruton's tyrosine kinase, the defective protein in immunodeficiency disease," *J Immunol.*, 165:6956-65, 2000.

Wilsker et al., "ARID proteins: a diverse family of DNA binding proteins implicated in the control of cell growth, differentiation, and development," *Cell Growth Differ.*, 13:95-106, 2002.

Wilsker et al., "Nomenclature of the ARID family of DNA-binding proteins," *Genomics*, 86:242-251, 2005.

Yu et al., "Induced pluripotent stem cell lines derived from human somatic cells," *Science*, 318:1917-1920, 2007.

Yu et al., "Human induced pluripotent stem cells free of vector and transgene sequences," *Science*, 324:797-801, 2009.

Zong et al., "Regulation of matrix attachment region-dependent, lymphocyte-restricted transcription through differential localization within promyelocytic leukemia nuclear bodies," *EMBO J.*, 19(15):4123-4133, 2000.

Fischer et al., "Lymphoma models for B cell activation and tolerance. X. Anti-μ-mediated growth arrest and apoptosis of murine B cell lymphomas is prevented by the stabilization of myc," *J. Exp. Med.*, 179:221-228, 1994.

Lin et al., "Cross talk between Id1 and its interactive protein DRIL1 mediate fibroblast responses to transforming growth factor-β in pulmonary fibrosis," *Am. J. Pathol.*, 173:337-346, 2008.

Prieur et al., "SUMOylation of DRIL1 directs its transcriptional activity towards Leukocyte lineage-specific genes," *PLoS One*, 4:e5542, 2009.

Schmidt et al., "Signalling of the BCR is regulated by a lipid rafts-localised transcription factor, Bright," *EMBO J.*, 28:711-724, 2009.

International Search Report and Written Opinion, issued in Application No. PCT/US2009/050242, mailed Jan. 27, 2010.

Invitation to Pay Additional Fees (partial search report), issued in Application No. PCT/US2009/050242, mail date Nov. 5, 2009.

Jaenisch and Young, "Stem cells, the molecular circuitry of pluripotency and nuclear reprogramming," *Cell*, 132:567-582, 2008.

Office Communication received in European Patent Application No. 09790275.3, dated May 7, 2012.

Ratliff et al., "The Transcription Factor ARID3a Is Important for in Vitro Differentiation of Human Hematopoietic Progenitors," *The Journal of Immunology*, 196: 614-623, 2016.

\* cited by examiner

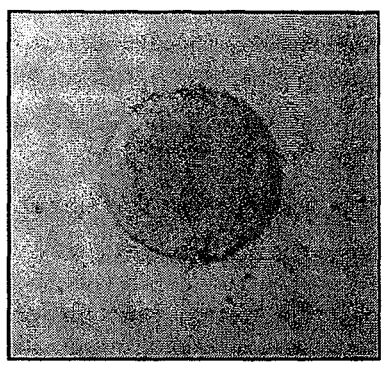 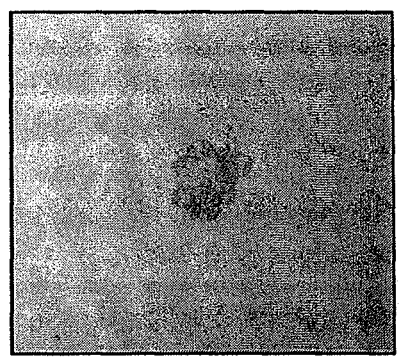
Standard ES cell medium    ES cell differentiation medium
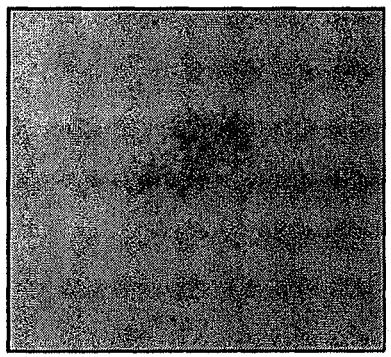 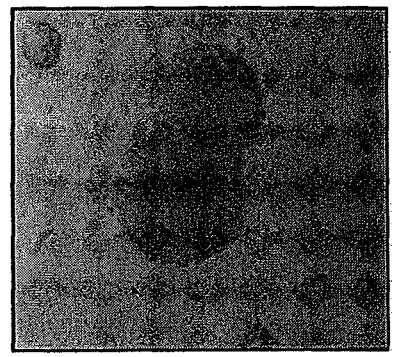
ENDO medium conditioned 9/28/07    RPMI SUP BRES ENDO 10-5-07
FIG. 4

PRODUCTION OF PLURIPOTENT CELLS THROUGH INHIBITION OF BRIGHT/ARID3A FUNCTION

PRIORITY INFORMATION

This application claims benefit of priority to U.S. Provisional Application Ser. No. 61/080,451, filed Jul. 14, 2008, the entire contents of which are hereby incorporated by reference.

GOVERNMENT SUPPORT CLAUSE

This invention was made with government support under grant nos. AI-44215 and AI-64886 awarded by National Institutes of Health. The government has certain rights in the invention.

BACKGROUND OF THE INVENTION

1. Field of the Invention

The present invention relates generally to the fields of developmental and molecular biology. More particularly, it concerns Bright/ARID3a function in the context of cell pluripotency. Specifically, the invention relates to the use inhibitors of Bright to regulate pluripotency, for example, in the context of de-differentiation and re-differentiation of cells.

2. Description of Related Art

Embryonic stem cells (ESCs) are pluripotent and can ultimately lead to the generation of all tissue types. Therefore, these cells have great potential for tissue replacement therapy in degenerative diseases. However, there are several major obstacles to overcome. First, the availability of ESCs is limited and ethically controversial. Second, growth of ESCs is technically challenging and requires feeder layers of other cells. Third, because the molecular mechanisms for controlled differentiation of specific cell types are not clearly delineated, there is risk that pluripotent cells will eventually result in production of unwanted cell types and/or tumor formation if their growth cannot be controlled. Finally, transplantation of tissues is best when major histocompatability antigens are identical and exact tissue matching has not been possible with currently utilized models.

There have been several recent reports that pluripotent cells can be generated from terminally differentiated cells, thereby opening up another possible source for ESCs. Somatic cell fusion technology and incubation of somatic cells with extracts from pluripotent cells have shown limited success, but more promising results have been obtained by focusing on four regulatory factors—Oct3/4, Sox2, c-Myc and Klf4. Yu et al. (2007) used these four genes to successfully reprogram fetal human fibroblasts. Takahashi et al. (2007) achieved similar results with adult human dermal fibroblasts. Nakagawa et al. (2008) was able to reprogram mouse fibroblasts with only Oct3/4, Sox2, and Klf4, thereby obviating concerns over the use of the c-Myc oncogene. Most recently, Hanna et al. (2008) used Oct3/4, Sox2, c-Myc and Klf4 to reprogram non-terminally differentiated mouse B-lymphocytes, although an additional factor was required to reprogram mature lymphocytes.

Despite these successes, the use of four different trangenes to achieve reprogramming has serious limitations. First, these methods are tedious and time consuming, and require introduction through viral vectors which remain in the host cells. Efficiencies are low (<1%), likely because it is not clear what gene dosages are necessary for reprogramming endogenous genes required for pluripotency. Second, the aforementioned concerns over the use of an oncogene will likely present a major hurdle to any in vivo applications in humans. Introduction of pluripotent cells into immuno-compromised mouse models typically leads to teratoma formation. And third, once de-differentiated, it may be difficult to re-differentiate cells if their transformation by Oct3/4, Sox2, c-Myc and Klf4 is stable, i.e., not transient or reversible. As such, there remains a need for improved methods of restoring pluripotency in terminally differentiated human cells.

SUMMARY OF THE INVENTION

Thus, in accordance with the present invention, there is provided a method of rendering a differentiated cell pluripotent comprising (a) providing a differentiated cell; and (b) contacting the cell with a inhibitor of Bright/ARID3a function to induce de-differentiation in the cell, wherein de-differentiation renders the cell pluripotent. The cell of step (a) may be a bone marrow cell, fibroblast cell or a spleen cell, or a peripheral blood cell. The inhibitor of Bright/ARID3a function may be an inhibitor of Bright/ARID3a expression, such as an interfering RNA. Alternatively, the inhibitor of Bright/ARID3a may be a dominant-negative Bright/ARID3a molecule. The dominant-negative Bright/ARID3a molecule may be encoded by an expression vector, such as a viral expression vector. The Bright/ARID3a inhibitor may be a Bright/ARID3a peptide.

The inhibition of Bright/ARID3a function may be reversible. The cell may be further treated, once pluripotent, with a signal that induces re-differentiation, such as a chemokine or growth factor. The cell, once treated, may express or or more markers of ectoderm, endoderm or mesoderm tissue. Re-differentiation may comprise developing one or more characteristics of a fat cell, a neuronal cell, a muscle cell or an endothelial cell, and Bright/ARID3a function in the cell may, once re-differentiated, be restored. The method may further comprise implanting the cell into a subject, and/or the subject may be the source of the cell in step (a).

In another embodiment, there is provided a method of reprogramming a differentiated cell comprising (a) providing a differentiated cell; (b) contacting the cell with an inhibitor of Bright/ARID3a function to induce de-differentiation in the cell; (c) contacting the cell, following de-differentiation, with a signal selected to produce a re-differentiated cell phenotype; (d) culturing said cell with the signal for a period of time sufficient to produce the re-differentiated cell phenotype; and (e) identifying one or more aspects of the re-differentiated cell phenotype in said cell. The cell of step (a) may be a bone marrow cell, a spleen cell, or a peripheral blood cell. The method may further comprise restoring Bright/ARID3a function following step (d). The signal may be a chemokine. The re-differentiated cell phenotype may be a fat cell phenotype, a neuronal cell phenotype, a muscle cell phenotype, a pancreatic cell phenotype, a hematopoietic cell phenotype or an endothelial cell phenotype.

In still another embodiment, there is provided a method of enhancing the growth of a stem cell comprising (a) providing a stem cell; (b) contacting the stem cell in culture with media conditioned by a Bright/ARID3a-deficient cell; and (c) culturing the stem cell. The stem may be an embryonic stem cell or a chord blood stem cell. The conditioned media may be pre-conditioned by culture of Bright/ARID3a-deficient cells media. The conditioned media may be conditioned by co-culturing of the stem cell and the Bright/

ARID3a-deficient cell. The Bright/ARID3a-deficient cell may contain an expression construct expressing a dominant-negative Bright/ARID3a, or an interfering RNA that blocks Bright/ARID3a expression. The method may further comprise contacting the stem cell following step (c) with a signal that induces differentiation. The signal may be chemokine. Bright/ARID3a function may be restored in the Bright/ARID3a-deficient cell.

Also encompassed by the present invention are kits comprising an inhibitor of Bright/ARID3a in a suitable receptacle. The receptacle may be a vial, syringe or tube. The kit may further comprise a pharmaceutically acceptable buffer, diluent or excipient, growth media, cytokines and/or growth factors, and/or may further comprise instructions for the preparation of the Bright/ARID3a inhibitor in a form suitable for administration to a subject. The Bright/ARID3a inhibitor may be selected from the group consisting of an interfering RNA, a dominant-negative Bright/ARID3a molecule, a Bright/ARID3a peptide or an expression vector coding therefor.

As used herein the specification, "a" or "an" may mean one or more. As used herein in the claim(s), when used in conjunction with the word "comprising," the words "a" or "an" may mean one or more than one. As used herein "another" may mean at least a second or more. Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 2A) Tube formation of endothelial-like cells from DN ARID3a spleen cultures. (FIG. 2B) Adherent cells from DN ARID3a cultures shown in FIG. 2A. (FIGS. 2C and 2D) Neural-lineage cells derived from bone marrow cells grown in matrigel and shown at low (FIG. 2C) and high (FIG. 2D) magnifications.

(FIG. 3A) cDNA from LPS stimulated spleen cells from a BCL2 transgenic (negative control) and a splenic ARID3a-deficient culture (BrSES) were amplified for Sox2 expression. (FIG. 3B) Nanog and C-myc expression were measured in mRNA from a standard ES cell line (+ control), two dominant-negative ARID3a spleen cell cultures (SCDND*36 and 50) and a culture derived from a non-transgenic control spleen. (FIGS. 3C and 3D) The samples from (FIG. 3B) were assessed for Lin28 and KLF-4 activity.

FIG. 4—Conditioned medium from ARID3a-deficient spleen cell cultures enhances growth and differentiation of standard ES cells. Standard ES cells were initiated as hanging drop cultures and were grown in either standard media or ES cell differentiation medium (top two panels). Parallel cultures were grown in conditioned media from ARID3a-deficient cells with enhanced endothelial cell growth (ENDO, bottom left) or with conditioned standard RPMI from ARID3a-deficient spleen cell cultures.

(FIG. 6A) Bright$^{-/-}$ spleen cell embryoid-like body (scale bar=50 μm). (FIG. 6B) Bright$^{-/-}$ spleen cells were grown in DMEM with 10% FCS and endothelial cell growth factors (magnification is 4×). (FIG. 6C) Flow cytometry reveals variable expression levels of the markers endothelial protein C receptor (EPCR), mouse thrombomodulin (MTM), and CD31 in a mouse hemangioma cell line (gift of C. Esmon, this institution) as well as the Bright$^{-/-}$ cells. (FIG. 6D) Bright$^{-/-}$ bone marrow cells cultured in RPMI with 5% FCS were seeded into matrigel and grown for three weeks. Branched neuron-like projections developed from cells growing in clusters (left panel, 10× magnification, right panel, 20×). (FIG. 6E) Neuron-like cells isolated from matrigel were stained with DAPI, anti-nestin or an isotype control.

(FIG. 7A) RT-PCR assays were performed with conventional ES cells, 6 week-old normal spleen (WT1) and 2 Bright$^{-/-}$ spleen cultures (BrSPS1 and BrSPS2) greater than 6 months old. (FIG. 7B) Bright$^{-/-}$ kidney cells formed iPSC-like colonies on MEFs similar to ES cells with small nuclei (DAPI stain, left panels) and expression of the early stem cell marker, SSEA-1 (right panels). The MEF monolayer in the same sections did not stain with SSEA-1. (scale bar=50 μm)

(FIG. 8A) DN Bright spleen cultures spontaneously produced embryoid-like bodies (top panel, brightfield, bottom panel, stained with actin-reactive phalloidin for emphasis of the three-dimensional multicellular structure) (20× magnification). (FIG. 8B) DN Bright spleen cultures (DN1 and DN2), control spleen cultures (WT1) and ES cells were assessed for gene expression by RT-PCR. (FIG. 8C) Genomic DNA from fresh spleen cells (spleen), a representative DN Bright cell line after 8 months in culture (DN1) and negative control ES and MEF cells (Con1 and 2) was amplified using primers for the germline Ig heavy chain locus (GL) and D to $J_H$ primers (D-$J_H$4). Arrows indicate expected products. (FIG. 8D) Control spleen, brain and DN1 cell line genomic DNA was amplified with multiple primers to detect $J_\kappa$ rearrangements (Ramsden et al., 1994). DN1a was prepared 50 days prior to the DN1b sample of the DN1 line. Arrows indicate expected products. (FIG. 8E) Sorted pre-B cells from DN-Bright mice formed IPS-like colonies after 3 weeks (left two panels), while control pre-B cells maintained their original morphology (right panel). (Scale bar=50 μm)

(FIG. 9A) Western blotting indicates that ARID3a is expressed more abundantly in 293T cells as compared to human fibroblast cell lines (WL-38, BJ-h, BJ and IM-R90). Samples were developed with anti-actin to show relative loading. Lane 2 is empty. (FIG. 9B) RT-PCR of ARID3a RNA levels demonstrates efficient knockdown in 2 Bright inhibited clones compared to control 293T cells. GAPDH served as a loading control. (FIG. 9C) Bright-inhibited 293T cells (BriPS) exhibited increasing iPS-like colony morphology compared to control 293T cultures with additional passages (p7 versus p10). (Scale bar=100 μm). (FIG. 9D) QRT-PCR of two clones (BriPS) versus the 293T parental cells shows fold-induction levels of KLf4, Oct4, Sox2 and c-myc transcripts relative to GAPDH. (FIG. 9E) Nuclear (DAPI) and Oct-4 staining for Oct4 were performed on BriPS and parental 293T cells. Scale bar=50 μm.

(FIG. 12A) RT-PCR showed that expression of three of the shRNAs (Tables S2, shRNA 1-3) inhibited Bright mRNA production 2 and 4 days after transduction in comparison to the scrambled control shRNAs (Con), which had no effect. Transduction efficiencies were >90%. Actin levels demonstrated equivalent sample loads. (FIG. 12B) Levels of Bright mRNA in (FIG. 12A) were corrected relative to actin levels, quantified for graphic presentation and showed >80% inhibition. Controls were arbitrarily set at 1. (FIG. 12C) Proteins from the cells in (FIG. 12A) were western blotted for Bright and actin, 2 and 4 days after viral infection.

DESCRIPTION OF ILLUSTRATIVE EMBODIMENTS

Figure 1:
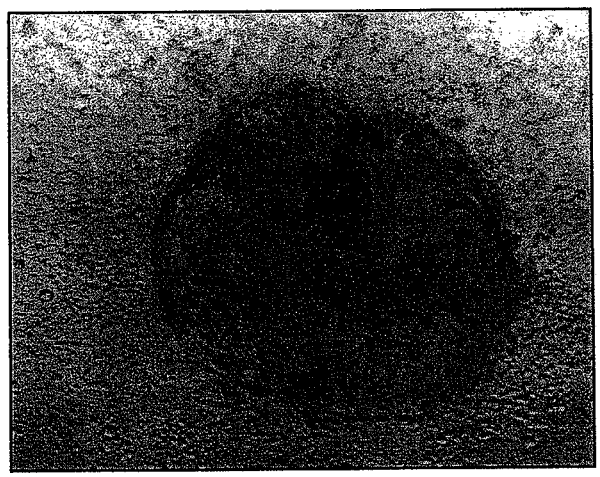
FIG. 1—Formation of embryoid bodies from ARID3a-deficient mice spleen.

Elegant studies from a number of laboratories have demonstrated the feasibility of reprogramming mature cells of multiple lineages into pluripotent states (Meissner et al., 2007; Yu et al., 2007; Takahashi and Yamanaka, 2006). The large number of advances in this field in just the last three years emphasizes the importance of these studies while making it impossible to adequately discuss them (reviewed in (Gurdon and Melton, 2008; Pei, 2009; Feng et al, 2009)). Introduction of combinations of Oct4, Sox2, Klf4, c-myc, Lin28 and Nanog into mature human and mouse cells results in reprogramming of those cells into induced pluripotent stem (iPS) cells which resemble embryonic stem cells (ES) (Meissner et al., 2007; Yu et al., 2007; Takahashi and Yamanaka, 2006). Some of those factors can be replaced by the addition of chemical inhibitors that cause epigenetic effects on chromatin, or by addition of additional protein products to the growth media (Feng et al., 2009; Marson et al., 2008). The increasing number of protocols, cell types and species used for iPS cell production has created controversy over the precise definition and phenotypic characteristics of iPS cells (Maherali and Hochedlinger, 2008). For example, human and mouse iPS cells differ in growth factor requirements, the efficiency by which they promote teratoma formation and in colony morphology (Pei et al., 2009; Feng et al., 2009). Recent data suggest that mouse iPS cells derived from different genetic backgrounds using the same methods, differ phenotypically (Hanna et al., 2009). Together, these studies emphasize the need for a better understanding of the key regulators and mechanistic processes involved in iPS cell production.

Here, the inventors show for the first time that inhibition of the transcription factor Bright (B cell regulator of immunoglobulin (Ig) heavy chain transcription (Webb et al., 1989; Webb et al., 1991; Herrscher et al., 1995)), also known as ARID3a, initiates reprogramming of cells resulting in pluripotency. Bright/ARID3a is the founder of the fifteen member ARID (A+T rich interaction domain) family of proteins (reviewed in (Wilsker et al, 2002; Wilsker et al., 2005)). The functions of most ARID family members have just begun to be elucidated and include roles in cell cycle control, (Flowers et al, 2009; Ho et al., 2009a; Ho et al., 2009b) ARID domain-dependent demethylase (Tu et al., 2008), histone deacetylase (Wilsker et al., 2005; Gray et al., 2005) activities, and chromatin remodeling (Wilsker et al., 2005). These results confirm that regenerative pluripotent cells can be derived from non-embryonic, readily available sources. Moreover, these data suggest the possibility that ESCs could be derived directly from individuals in need of such tissues. Furthermore, preliminary data indicate that supernatants derived from Bright-defective stem cells enhance the growth of currently available ESC lines. Finally, reversible inhibition of Bright function should permit production of stem cells, differentiation into a specific tissue pathway, and re-expression of Bright after removal of the inhibitory agent. Such cells should lose their pluripotency and, presumably, any tumorigenic characteristics. These and other aspects of the invention are described below.

I. BRIGHT/ARID3A

The transcription factor Bright (B cell regulator of IgH transcription) is a member of a growing family of proteins that interact with DNA through a highly conserved A+T-rich interaction domain, or ARID (Herrscher et al., 1995). Currently, Bright is the only member of this family for which target sequences have been identified, and which binds to DNA in a sequence-specific fashion. ARID family proteins include the *Drosophila* proteins Dead ringer and eyelid that play important roles in lineage decisions in the gut and eyelid of the fruit fly, and are required for embryonic segmentation (Gregory et al., 1996; Treisman et al., 1997); retinoblastoma binding protein (Rbp1) that interacts with retinoblastoma protein in a cell cycle-specific fashion (Fattaey et al., 1993); and BDP, a ubiquitously expressed human protein identified in a two-hybrid screen as a novel protein that also interacts with retinoblastoma protein (Rb) (Numata et al., 1999). The yeast protein SWI/1 has homology to Bright, and is a component of a larger protein complex that serves to modulate chromatin organization in that organism (Peterson and Herskowitz, 1992; Burns and Peterson, 1997). Likewise, the human SWI-SNF complex contains a 270 kDa protein with non-sequence specific DNA binding activity that is also a member of the ARID family (Dallas et al., 2000). Thus, members of this family may participate in lineage decisions, cell cycle control, tumor suppression and modulation of chromatin. These functions are not mutually exclusive and may result from overlapping mechanisms.

Sequencing of the human genome identified fifteen members of this family, including the human Bright ortholog known as ARID3a (Wilsker et al., 2005). ARID family proteins have diverse functions including, chromatin remodeling, binding to retinoblastoma protein, regulating X-Y chromosome functions and participation in embryonic development (Wilsker et al., 2005). Generally, these proteins are components of large protein complexes and are tightly regulated throughout development. Human ARID3a can bind to E2F in cell lines of embryonic origin where its over-expression is controversial, as it has been associated with both tumor suppressor and oncogenic functions (Peeper et al., 2002; Suzuki et al, 1998; Ma et al., 2003; Fukuyo et al., 2004). Recent studies indicate that Bright activity is regulated tightly through intracellular partitioning and that it contributes to chromatin accessibility of the heavy chain enhancer (Kim and Tucker, 2006; Lin et al., 2007). It is likely that Bright/ARID3a can participate in a wide variety of regulatory functions in both embryonic and adult tissues because it functions as both a transcription factor and has a role in altering chromatin accessibility.

Most ARID family proteins are expressed ubiquitously. However, murine Bright is expressed widely throughout embryonic development, but expression in the adult is largely limited to the B lymphocyte lineage where its expression is tightly regulated and is restricted at the mRNA level to the pre-B cell and peanut agglutinin-high germinal center cell populations (Herrscher et al., 1995; Webb et al., 1991; Webb et al., 1998). Activated splenic B cells in the mouse can be induced to express Bright after antigen binding, but the protein is not present in the majority of peripheral IgM$^+$ B cells (Webb et al., 1991; Webb et al., 1998). Induction of Bright expression in B cell lines or in mature activated B lymphocytes using lipopolysaccharide or antigen results in upregulation of IgH transcription approximately 3- to 6-fold above basal levels (Herrscher et al., 1995; Webb et al., 1991; Webb et al., 1989). Transcriptional activation is tightly associated with DNA binding sites 5' of some $V_H$ promoters or within the intronic Eµ enhancer.

Bright binding sites associated with the intronic Eµ enhancer also function as matrix-association regions, or MARs, A+T rich regions that have been proposed to organize chromatin into transcriptionally active domains (Herrscher et al. 1995; Webb et al., 1991). NFµNR (nuclear factor µ negative regulator) is another MAR-binding protein complex that binds DNA sequences overlapping Bright binding sites. NFµNR contains the ubiquitously expressed CAAAT displacement protein (CDP/Cut/Cux) (Wang et al., 1999). While non-B cells in the mouse express NFµNR, B lymphocytes generally do not exhibit such protein complexes. These data have led to the hypothesis that Bright and NFµNR play opposing roles in regulating the immunoglobulin locus (Webb et al., 1999). Transfection studies in which Bright and CDP were coexpressed showed repression of Bright (Wang et al, 1999). Therefore, Bright may activate transcription, directly or indirectly through chromatin remodeling or through more complex interactions with additional proteins. NFµNR may act in opposition to that activity (Wang et al., 1999).

The inventor has shown that Bruton's tyrosine kinase, or Btk, associates with Bright in activated murine B lymphocytes (Webb et al., 2000). Btk is an X-linked gene that encodes a tyrosine kinase critical for proper development and maintenance of B lymphocytes both in humans and in mice (reviewed in (Conley et al., 1994; Satterthwaite and Witte, 1996). Defects in this enzyme account for 90% of the severe B cell immunodeficiencies in man, and result in X-linked agammaglobulinemia (XLA), an immunodeficiency state characterized by blocks at the pro-B cell stage of development and severely depressed serum antibody levels (Conley et al., 1994). Although Btk is clearly the defective gene product in both human and murine diseases, the molecular mechanisms by which Btk deficiencies result in blocks in B cell development are currently unknown. Of interest, X-linked immunodeficient (xid) mice, the mouse model for XLA, produce a mutated Btk protein that fails to form stable complexes with Bright (Webb et al., 2000). These data suggest that Bright may function as a component of the same signaling pathway(s) important in XLA.

Very little information is available regarding human Bright protein. Therefore, the inventor sought to characterize the human Bright homologue and to determine its expression in B lymphocyte subpopulations. Bright was cloned from a human B cell library and the sequence was determined to be identical to that published previously as Dril 1 (Kortschak et al., 1998). Although these studies suggested that Dril 1, or human Bright, mRNA was expressed in multiple tissues (Kortschak et al., 1998), protein and DNA binding activity were not investigated. The inventor's data indicate that Bright/Dril 1 mRNA may be expressed in a smaller number of adult tissues than previously thought. Furthermore, these data demonstrate that the human protein effectively binds the Bright prototype sequence motif. Investigation of sorted B cell subpopulations demonstrated that human Bright expression was similar in many ways to expression of the murine homologue; although, Bright mRNA was expressed at slightly earlier stages of normal B cell development in man than in the mouse. On the other hand, expression of Bright protein in human transformed cell lines differed dramatically from that observed in the mouse. Finally, results reveal that human Bright and Btk associate to form DNA-binding complexes, which further involve the Btk substrate TFII-I (Rajaiya et al., 2006).

II. PEPTIDES AND POLYPEPTIDES

In certain embodiments, the present invention may concerns Bright/ARID3a protein molecules. As used herein, a "protein" or "polypeptide" generally refers, but is not limited to, a protein of greater than about 100 amino acids or the full length endogenous sequence translated form of a gene. A peptide is usually from about 3 to about 100 amino acids. All the "proteinaceous" terms described above may be used interchangeably herein. A human ARID3a polypeptide sequence is provided in SEQ ID NO:2.

Proteins may be produced recombinantly or purified from natural sources. Shorter peptide molecules may be synthesized in solution or on a solid support in accordance with conventional techniques. Various automatic synthesizers are commercially available and can be used in accordance with known protocols. See, e.g., Stewart and Young (1984); Tam et al. (1983); Merrifield (1986); and Barany and Merrifield (1979), each incorporated herein by reference.

In certain embodiments the size of the at least one proteinaceous molecule may comprise, but is not limited to, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 505, about 525, about 550, about 575 and 593 amino molecule residues, and any range derivable therein.

As used herein, an "amino acid" refers to any amino acid, amino acid derivative or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

In certain embodiments, the proteinaceous composition comprises at least one protein, polypeptide or peptide. In further embodiments, the proteinaceous composition comprises a biocompatible protein, polypeptide or peptide. As used herein, the term "biocompatible" refers to a substance which produces no significant untoward effects when applied to, or administered to, a given organism according to the methods and amounts described herein. Such untoward or undesirable effects are those such as significant toxicity or adverse immunological reactions. In preferred embodiments, biocompatible protein, polypeptide or peptide containing compositions will generally be mammalian proteins or peptides or synthetic proteins or peptides each essentially free from toxins, pathogens and harmful immunogens.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. The nucleotide and protein, polypeptide and peptide sequences for various genes have been previously disclosed, and may be found at computerized databases known to those of ordinary skill in the art. One such database is the National Center for Biotechnology Information's Genbank and GenPept databases (world-wide-web at ncbi.nlm.nih.gov). The coding regions for these known genes may be amplified and/or expressed using the techniques disclosed herein or as would be know to those of ordinary skill in the art. Alternatively, various commercial preparations of proteins, polypeptides and peptides are known to those of skill in the art.

Peptides may also be fused to other proteinaceous compositions, thereby altering or supplementing their properties. In a particular embodiment, a targeting moiety may be provided which facilitate cellular transport of the Bright derived peptide or polypeptide. In particular, sequences such as Tat can provide nuclear localization signals, thereby transporting peptides into the nucleus.

In certain embodiments, a proteinaceous compound may be purified. Generally, "purified" will refer to a specific or protein, polypeptide, or peptide composition that has been subjected to fractionation to remove various other proteins, polypeptides, or peptides, and which composition substantially retains its activity, as may be assessed, for example, by the protein assays, as would be known to one of ordinary skill in the art for the specific or desired protein, polypeptide or peptide.

III. NUCLEIC ACIDS

In certain embodiments of the present invention, nucleic acids derived from or encoding Bright are provided. In certain aspects, the nucleic acids may comprise wild-type or a mutant version of these genes. In particular aspects, the nucleic acid encodes for or comprises a transcribed nucleic acid. In other aspects, the nucleic acid comprises a nucleic acid segment of SEQ ID NO:1, or a biologically functional equivalent thereof. In particular aspects, the nucleic acid encodes a protein, polypeptide, peptide.

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally-occurring purine or pyrimidine base found in DNA (e.g., an adenine "A," a guanine "G," a thymine "T" or a cytosine "C") or RNA (e.g., an "A," a "G," an uracil "U" or a "C"). The term "nucleic acid" encompass the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length.

These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or "complement(s)" of a particular sequence comprising a molecule. As used herein, a single-stranded nucleic acid may be denoted by the prefix "ss," a double-stranded nucleic acid by the prefix "ds," and a triple-stranded nucleic acid by the prefix "ts."

1. Preparation of Nucleic Acids

A nucleic acid may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266 032, incorporated herein by reference, or via deoxynucleoside H-phosphonate intermediates as described by Froehler et al. (1986) and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 2001, incorporated herein by reference).

2. Purification of Nucleic Acids

A nucleic acid may be purified on polyacrylamide gels, cesium chloride centrifugation gradients, or by any other means known to one of ordinary skill in the art (see for example, Sambrook et al., 2001, incorporated herein by reference).

In certain aspect, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

3. Nucleic Acid Segments

In certain embodiments, the nucleic acid is a nucleic acid segment. As used herein, the term "nucleic acid segment," are smaller fragments of a nucleic acid, such as for non-limiting example, those that encode only part of Bright. Thus, a "nucleic acid segment" may comprise any part of a gene sequence, of from about 2 nucleotides to the full length of Bright. In certain embodiments, the nucleic acid segment may be a probe or primer. As used herein, a "probe" generally refers to a nucleic acid used in a detection method or composition. As used herein, a "primer" generally refers to a nucleic acid used in an extension or amplification method or composition.

4. Nucleic Acid Complements

The present invention also encompasses a nucleic acid that is complementary to a Bright-encoding nucleic acid. In particular embodiments the invention encompasses a nucleic acid or a nucleic acid segment complementary to the sequence set forth in SEQ ID NO:1. A nucleic acid is a "complement(s)" or is "complementary" to another nucleic acid when it is capable of base-pairing with another nucleic acid according to the standard Watson-Crick, Hoogsteen or reverse Hoogsteen binding complementarity rules. As used herein "another nucleic acid" may refer to a separate molecule or a spatial separated sequence of the same molecule.

As used herein, the term "complementary" or "complement(s)" also refers to a nucleic acid comprising a sequence of consecutive nucleobases or semiconsecutive nucleobases (e.g., one or more nucleobase moieties are not present in the molecule) capable of hybridizing to another nucleic acid strand or duplex even if less than all the nucleobases do not base pair with a counterpart nucleobase. In certain embodiments, a "complementary" nucleic acid comprises a sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range derivable therein, of the nucleobase sequence is capable of base-pairing with a single or double stranded nucleic acid molecule during hybridization. In certain embodiments, the term "complementary" refers to a nucleic acid that may hybridize to another nucleic acid strand or duplex in stringent conditions, as would be understood by one of ordinary skill in the art.

In certain embodiments, a "partly complementary" nucleic acid comprises a sequence that may hybridize in low stringency conditions to a single or double stranded nucleic acid, or contains a sequence in which less than about 70% of the nucleobase sequence is capable of base-pairing with a single or double stranded nucleic acid molecule during hybridization.

5. Hybridization

As used herein, "hybridization," "hybridizes" or "capable of hybridizing" is understood to mean the forming of a double or triple stranded molecule or a molecule with partial double or triple stranded nature. The term "anneal" as used herein is synonymous with "hybridize." The term "hybridization," "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions," and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

As used herein "wild-type" refers to the naturally occurring sequence of a nucleic acid at a genetic locus in the genome of an organism, or a sequence transcribed or translated from such a nucleic acid. Thus, the term "wild-type" also may refer to an amino acid sequence encoded by a nucleic acid. As a genetic locus may have more than one sequence or alleles in a population of individuals, the term "wild-type" encompasses all such naturally occurring allele(s). As used herein the term "polymorphic" means that variation exists (i.e., two or more alleles exist) at a genetic locus in the individuals of a population. As used herein "mutant" refers to a change in the sequence of a nucleic acid or its encoded protein, polypeptide or peptide that is the result of the hand of man.

The present invention also concerns the isolation or creation of a recombinant construct or a recombinant host cell through the application of recombinant nucleic acid technology known to those of skill in the art or as described herein. A recombinant construct or host cell may comprise a Bright-encoding nucleic acid, and may express a Bright protein, peptide or peptide, or at least one biologically functional equivalent thereof.

Herein certain embodiments, a "gene" refers to a nucleic acid that is transcribed. In certain aspects, the gene includes regulatory sequences involved in transcription, or message production or composition. In particular embodiments, the gene comprises transcribed sequences that encode for a protein, polypeptide or peptide. As will be understood by those in the art, this function term "gene" includes both genomic sequences, RNA or cDNA sequences or smaller engineered nucleic acid segments, including nucleic acid segments of a non-transcribed part of a gene, including but not limited to the non-transcribed promoter or enhancer regions of a gene. Smaller engineered gene nucleic acid segments may express, or may be adapted to express using nucleic acid manipulation technology, proteins, polypeptides, domains, peptides, fusion proteins, mutants and/or such like.

"Isolated substantially away from other coding sequences" means that the gene of interest forms the significant part of the coding region of the nucleic acid, or that the nucleic acid does not contain large portions of naturally-occurring coding nucleic acids, such as large chromosomal fragments, other functional genes, RNA or cDNA coding regions. Of course, this refers to the nucleic acid as originally isolated, and does not exclude genes or coding regions later added to the nucleic acid by the hand of man.

The nucleic acid(s) of the present invention, regardless of the length of the sequence itself, may be combined with other nucleic acid sequences, including but not limited to, promoters, enhancers, polyadenylation signals, restriction enzyme sites, multiple cloning sites, coding segments, and the like, to create one or more nucleic acid construct(s). As used herein, a "nucleic acid construct" is a nucleic acid engineered or altered by the hand of man, and generally comprises one or more nucleic acid sequences organized by the hand of man.

In a non-limiting example, one or more nucleic acid constructs may be prepared that include a contiguous stretch of nucleotides identical to or complementary to SEQ ID NO:1. A nucleic acid construct may be about 3, about 5, about 8, about 10 to about 14, or about 15, about 20, about 30, about 40, about 50, about 100, about 200, about 500, about 1,000, about 2,000, about 3,000, about 5,000, or about 10,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges," as used herein, means any length or range including or between the quoted values (i.e., all integers including and between such values). Non-limiting examples of intermediate lengths include about 11, about 12, about 13, about 16, about 17, about 18, about 19, etc.; about 21, about 22, about 23, etc.; about 31, about 32, etc.; about 51, about 52, about 53, etc.; about 101, about 102, about 103, etc.; about 151, about 152, about 153, etc.; about 1,001, about 1002, etc.; about 10,001, about 10,002, etc. Non-limiting examples of intermediate ranges include about 3 to about 32, about 150 to about 500, or about 5,000 to about 15,000, etc.

The term "biologically functional equivalent" is well understood in the art. Accordingly, a sequence that has between about 70% and about 80%; or more preferably, between about 81% and about 90%; or even more preferably, between about 91% and about 99%; of amino acids that are identical or functionally equivalent to the amino acids of SEQ ID NO:2 will be a sequence that is "essentially as set forth in SEQ ID NO:2," provided the biological activity of the protein, polypeptide or peptide is maintained, Table 1 provides a listing of preferred human codons.

TABLE 1

| Amino Acids | | | Codons | | | | |
|---|---|---|---|---|---|---|---|
| Alanine | Ala | A | GCC | GCT | GCA | GCG | |
| Cysteine | Cys | C | TGC | TGT | | | |
| Aspartic acid | Asp | D | GAC | GAT | | | |
| Glutamic acid | Glu | E | GAG | GAA | | | |
| Phenylalanine | Phe | F | TTC | TTT | | | |
| Glycine | Gly | G | GGC | GGG | GGA | GGT | |
| Histidine | His | H | CAC | CAT | | | |
| Isoleucine | Ile | I | ATC | ATT | ATA | | |
| Lysine | Lys | K | AAG | AAA | | | |
| Leucine | Leu | L | CTG | CTC | TTG | CTT | CTA | TTA |
| Methionine | Met | M | ATG | | | | |
| Asparagine | Asn | N | AAC | AAT | | | |
| Proline | Pro | P | CCC | CCT | CCA | CCG | |
| Glutamine | Gln | Q | CAG | CAA | | | |
| Arginine | Arg | R | CGC | AGG | CGG | AGA | CGA | CGT |

TABLE 1-continued

| Amino Acids | | | Codons | | | | | |
|---|---|---|---|---|---|---|---|---|
| Serine | Ser | S | AGC | TCC | TCT | AGT | TCA | TCG |
| Threonine | Thr | T | ACC | ACA | ACT | ACG | | |
| Valine | Val | V | GTG | GTC | GTT | GTA | | |
| Tryptophan | Trp | W | TGG | | | | | |
| Tyrosine | Tyr | Y | TAC | TAT | | | | |

It will also be understood that amino acid sequences or nucleic acid sequences may include additional residues, such as additional N- or C-terminal amino acids or 5' or 3' sequences, or various combinations thereof, and yet still be essentially as set forth in one of the sequences disclosed herein, so long as the sequence meets the criteria set forth above, including the maintenance of biological protein, polypeptide or peptide activity where expression of a proteinaceous composition is concerned. The addition of terminal sequences particularly applies to nucleic acid sequences that may, for example, include various non-coding sequences flanking either of the 5' and/or 3' portions of the coding region or may include various internal sequences, i.e., introns, which are known to occur within genes.

Excepting intronic and flanking regions, and allowing for the degeneracy of the genetic code, the present invention also provides for nucleic acid sequences that have between about 70% and about 79%; or more preferably, between about 80% and about 89%; or even more particularly, between about 90% and about 99%; of nucleotides that are identical to the nucleotides of SEQ ID NO:1.

It will also be understood that this invention is not limited to the particular nucleic acid or amino acid sequence of SEQ ID NO:1 or 2. Recombinant vectors and isolated nucleic acid segments may therefore variously include these coding regions themselves, coding regions bearing selected alterations or modifications in the basic coding region, and they may encode larger polypeptides or peptides that nevertheless include such coding regions or may encode biologically functional equivalent proteins, polypeptide or peptides that have variant amino acids sequences.

The nucleic acids of the present invention encompass biologically functional equivalent proteins, polypeptides, or peptides. Such sequences may arise as a consequence of codon redundancy or functional equivalency that are known to occur naturally within nucleic acid sequences or the proteins, polypeptides or peptides thus encoded. Alternatively, functionally equivalent proteins, polypeptides or peptides may be created via the application of recombinant DNA technology, in which changes in the protein, polypeptide or peptide structure may be engineered, based on considerations of the properties of the amino acids being exchanged. Changes designed by man may be introduced, for example, through the application of site-directed mutagenesis techniques as discussed herein below, e.g., to introduce improvements or alterations to the antigenicity of the protein, polypeptide or peptide.

Encompassed by the invention are nucleic acid sequences encoding relatively small peptides or fusion peptides, such as, for example, peptides of from about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, to about 100 amino acids in length, or more preferably, of from about 15 to about 30 amino acids in length; as set forth in SEQ ID NO:2.

IV. SCREENING METHODS

The present invention further comprises methods for identifying inhibitors of Bright activity that are useful in the reprogramming of differentiated cells. These assays may comprise random screening of large libraries of candidate substances; alternatively, the assays may be used to focus on particular classes of compounds selected with an eye towards structural attributes that are believed to make them more likely to inhibit the function of Bright.

To identify an inhibitor of Bright, one generally will determine the function of Bright in the presence and absence of the candidate substance. For example, a method generally comprises:

(a) providing a cell that expresses Bright;
(b) contacting said with a candidate inhibitor substance; and
(c) measuring a Bright-related activity;

wherein a decrease in a Bright related activity, as compared to Bright activity of an untreated cell, identifies the candidate substance as an inhibitor of Bright activity. Activities include stimulation of immunoglobulin production, Bright homodimerization, Bright DNA binding, Bright interaction with Btk, and Bright interaction with TFII-I. Assays also may be conducted in isolated cells, cell extracts, organs, or in living organisms.

It will, of course, be understood that all the screening methods of the present invention are useful in themselves notwithstanding the fact that effective candidates may not be found. The invention provides methods for screening for such candidates, not solely methods of finding them.

A. Modulators

As used herein the term "candidate substance" refers to any molecule that may potentially inhibit the activity Bright. The candidate substance may be a protein or fragment thereof, a small molecule, or even a nucleic acid. It may prove to be the case that the most useful pharmacological compounds will be compounds that are structurally related to Bright/ARID3a, or a Bright/ARID3a interacting protein, such as Btk or TFII-I. Using lead compounds to help develop improved compounds is known as "rational drug design" and includes not only comparisons with know inhibitors and activators, but predictions relating to the structure of target molecules.

The goal of rational drug design is to produce structural analogs of biologically active polypeptides or target compounds. By creating such analogs, it is possible to fashion drugs which are more active or stable than the natural molecules, which have different susceptibility to alteration, or which may affect the function of various other molecules.

In one approach, one would generate a three-dimensional structure for a target molecule, or a fragment thereof. This could be accomplished by x-ray crystallography, computer modeling, or by a combination of both approaches.

It also is possible to use antibodies to ascertain the structure of a target compound, activator, or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecular libraries that are believed to meet the basic criteria for useful drugs in an effort to "brute force" the identification of useful compounds. Screening of such libraries, including combinatorially-generated libraries (e.g., peptide libraries), is a rapid and efficient way to screen large number of related (and unrelated) compounds for activity. Combinatorial approaches also lend themselves to rapid evolution of potential drugs by the creation of second, third, and fourth generation compounds modeled on active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, ribozymes, and antibodies (including single chain antibodies), each of which would be specific for the target molecule. Such compounds are described in greater detail elsewhere in this document. For example, an antisense molecule that bound to a translational or transcriptional start site, or splice junctions, would be ideal candidate inhibitors.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

B. In vitro Assays

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads. A common form of in vitro assay is a binding assay.

A particular format contemplated by the inventors involves the assessing of Bright/ARID3a binding to DNA. Both molecules are labeled with agents that can be detected individually or by virtue of fluorescence energy transfer.

A technique for high throughput screening of compounds is described in WO 84/03564. Large numbers of small peptide test compounds are synthesized on a solid substrate, such as plastic pins or some other surface.

C. In Cyto Assays

The present invention also contemplates the screening of compounds for their ability to modulate Bright/ARID3a activity in cells. Various cells and cell lines can be utilized for such screening assays, including cells specifically engineered for this purpose. Other cells include embryonic fibroblasts and other embryonic tissues. Of particular interest are cells that contain an Ig promoter linked to a selectable or screenable marker gene.

D. In Vivo Assays

In vivo assays involve the use of various animal models, including transgenic animals that have been engineered to have specific defects or carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for inhibitors may be conducted using an animal model derived from any of these species.

Treatment of animals with test compounds will involve the administration of the compound, in an appropriate form, to the animal, or to cells derived from such animals. Administration will be by any route that could be utilized for clinical purposes. Determining the effectiveness of a compound in vivo may involve a variety of different criteria. Also, measuring toxicity and dose response can be performed in animals in a more meaningful fashion than in in vitro or in cyto assays.

V. TREATING DIFFERENTIATED CELLS TO INDUCE PLURIPOTENCY

A. Cell Sources

Cells may be obtained from a wide variety of sources, including kidney, isolated B-cell subpopulations, bone marrow, and fibroblasts B. Bright Inhibitors The present invention contemplates the use of virtually any composition that will inhibit Bright/ARID3a function. Organopharmaceutical compounds that produce the desired effect would find great utility, and such compounds may be identified according to the screening methods described above. In addition, biological inhibitors, as described below, may be utilized to interfere with Bright/ARID3a function.

C. Antisense Constructs

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

D. Ribozymes

Another general class of inhibitors is ribozymes. Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cook, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cook et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cook et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). It has also been shown that ribozymes can elicit genetic changes in some cells lines to which they were applied; the altered genes included the oncogenes H-ras, c-fos and genes of HIV. Most of this work involved the modification of a target mRNA, based on a specific mutant codon that was cleaved by a specific ribozyme.

E. RNAi

RNA interference (also referred to as "RNA-mediated interference" or RNAi) is another mechanism by which protein expression can be reduced or eliminated. Double-stranded RNA (dsRNA) has been observed to mediate the reduction, which is a multi-step process. dsRNA activates post-transcriptional gene expression surveillance mechanisms that appear to function to defend cells from virus infection and transposon activity (Fire et al., 1998; Grishok et al., 2000; Ketting et al., 1999; Lin et al., 1999; Montgomery et al., 1998; Sharp et al., 2000; Tabara et al., 1999). Activation of these mechanisms targets mature, dsRNA-complementary mRNA for destruction. RNAi offers major experimental advantages for study of gene function. These advantages include a very high specificity, ease of movement across cell membranes, and prolonged down-regulation of the targeted gene (Fire et al., 1998; Grishok et al., 2000; Ketting et al., 1999; Lin et al., 1999; Montgomery et al., 1998; Sharp, 1999; Sharp et al., 2000; Tabara et al., 1999). Moreover, dsRNA has been shown to silence genes in a wide range of systems, including plants, protozoans, fungi, C. elegans, Trypanasoma, Drosophila, and mammals (Grishok et al, 2000; Sharp, 1999; Sharp et al., 2000; Elbashir et al., 2001). It is generally accepted that RNAi acts post-transcriptionally, targeting RNA transcripts for degradation, and possibly by inhibiting translation. It appears that both nuclear and cytoplasmic RNA can be targeted (Bosher et al., 2000).

siRNAs must be designed so that they are specific and effective in suppressing the expression of the genes of interest. Methods of selecting the target sequences, i.e. those sequences present in the gene or genes of interest to which the siRNAs will guide the degradative machinery, are directed to avoiding sequences that may interfere with the siRNA's guide function while including sequences that are specific to the gene or genes. Typically, siRNA target sequences of about 21 to 23 nucleotides in length are most effective. This length reflects the lengths of digestion products resulting from the processing of much longer RNAs as described above (Montgomery et al., 1998). Of particular interest are those siRNAs that span an exon-intron junction.

The making of siRNAs has been mainly through direct chemical synthesis; through processing of longer, double stranded RNAs through exposure to Drosophila embryo lysates; or through an in vitro system derived from S2 cells. Use of cell lysates or in vitro processing may further involve the subsequent isolation of the short, 21-23 nucleotide siRNAs from the lysate, etc., making the process somewhat cumbersome and expensive. Chemical synthesis proceeds by making two single stranded RNA-oligomers followed by the annealing of the two single stranded oligomers into a double stranded RNA. Methods of chemical synthesis are diverse. Non-limiting examples are provided in U.S. Pat. Nos. 5,889,136, 4,415,732, and 4,458,066, expressly incorporated herein by reference, and in Wincott et al. (1995).

Several further modifications to siRNA sequences have been suggested in order to alter their stability or improve their effectiveness. It is suggested that synthetic complementary 21-mer RNAs having di-nucleotide overhangs (i.e., 19 complementary nucleotides+3' non-complementary dimers) may provide the greatest level of suppression. These protocols primarily use a sequence of two (2'-deoxy)thymidine nucleotides as the di-nucleotide overhangs. These dinucleotide overhangs are often written as dTdT to distinguish them from the typical nucleotides incorporated into RNA. The literature has indicated that the use of dT overhangs is primarily motivated by the need to reduce the cost of the chemically synthesized RNAs. It is also suggested that the dTdT overhangs might be more stable than UU overhangs, though the data available shows only a slight (<20%) improvement of the dTdT overhang compared to an siRNA with a UU overhang.

Chemically synthesized siRNAs are found to work optimally when they are in cell culture at concentrations of 25-100 nM. This had been demonstrated by Elbashir et al. (2001) wherein concentrations of about 100 nM achieved effective suppression of expression in mammalian cells. siRNAs have been most effective in mammalian cell culture at about 100 nM. In several instances, however, lower concentrations of chemically synthesized siRNA have been used (Caplen et al., 2000; Elbashir et al., 2001).

WO 99/32619 and WO 01/68836 suggest that RNA for use in siRNA may be chemically or enzymatically synthesized. Both of these texts are incorporated herein in their entirety by reference. The enzymatic synthesis contemplated in these references is by a cellular RNA polymerase or a bacteriophage RNA polymerase (e.g., T3, T7, SP6) via the use and production of an expression construct as is known in the art. See U.S. Pat. No. 5,795,715. The contemplated constructs provide templates that produce RNAs that contain nucleotide sequences identical to a portion of the target gene. The length of identical sequences provided by these references is at least 25 bases, and may be as many as 400 or more bases in length. An important aspect of this reference is that the authors contemplate digesting longer dsRNAs to 21-25 mer lengths with the endogenous nuclease complex that converts long dsRNAs to siRNAs in vivo. They do not describe or present data for synthesizing and using in vitro transcribed 21-25 mer dsRNAs. No distinction is made between the expected properties of chemical or enzymatically synthesized dsRNA in its use in RNA interference.

Similarly, WO 00/44914, incorporated herein by reference, suggests that single strands of RNA can be produced enzymatically or by partial/total organic synthesis. Preferably, single stranded RNA is enzymatically synthesized from the PCR™ products of a DNA template, preferably a cloned cDNA template and the RNA product is a complete transcript of the cDNA, which may comprise hundreds of nucleotides. WO 01/36646, incorporated herein by reference, places no limitation upon the manner in which the siRNA is synthesized, providing that the RNA may be synthesized in vitro or in vivo, using manual and/or automated procedures. This reference also provides that in vitro synthesis may be chemical or enzymatic, for example using cloned RNA polymerase (e.g., T3, T7, SP6) for transcription of the endogenous DNA (or cDNA) template, or a mixture of both. Again, no distinction in the desirable properties for use in RNA interference is made between chemically or enzymatically synthesized siRNA.

U.S. Pat. No. 5,795,715 reports the simultaneous transcription of two complementary DNA sequence strands in a single reaction mixture, wherein the two transcripts are immediately hybridized. The templates used are preferably of between 40 and 100 base pairs, and which is equipped at each end with a promoter sequence. The templates can be attached to a solid surface. After transcription with RNA polymerase, the resulting dsRNA fragments may be used for detecting and/or assaying nucleic acid target sequences.

In a specific embodiment, the inventors propose to inhibit ARID3a expression in adult tissues in vitro using siRNA or shRNA in a lentiviral vector. A GFP marker can be utilized to determine that cells took up the vector, and thus permit checking for appropriate inhibition of ARID3a production. The B cell line BCg3R-1d and/or over-expressing transgenic mouse spleen cells can be utilized. After the inventors confirm that inhibition of ARID3a occurs in these cells, they will inhibit ARID3a expression in mouse embryo fibroblasts and culture the GFP+ cells to confirm that pluripotent stem cells develop. The use of an inducible promoter (discussed below) that allow induction of the siRNA or shRNA only under specific growth conditions permit reversible inhibition of ARID3a. Thus, cells can be induced to dedifferentiate into a pluripotent and self-renewing state in vitro, and can then be induced to differentiate into mature lineage cells under different growth conditions without inhibition of ARID3a. These methods offer considerable advantages over current methodologies, which involve introduction of multiple viral copies and genes, some of which are known to be oncogenic. Self-deleting vectors may also be used.

F. Antibodies

In certain aspects of the invention, antibodies may find use as inhibitors of Bright. As used herein, the term "antibody" is intended to refer broadly to any appropriate immunologic binding agent such as IgG, IgM, IgA, IgD and IgE. Generally, IgG and/or IgM are preferred because they are the most common antibodies in the physiological situation and because they are most easily made in a laboratory setting.

The term "antibody" also refers to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art.

Monoclonal antibodies (MAbs) are recognized to have certain advantages, e.g., reproducibility and large-scale production, and their use is generally preferred. The invention thus provides monoclonal antibodies of the human, murine, monkey, rat, hamster, rabbit and even chicken origin. Due to the ease of preparation and ready availability of reagents, murine monoclonal antibodies will often be preferred. Single-chain Mabs are described in U.S. Pat. Nos. 4,946,778 and 5,888,773, each of which are hereby incorporated by reference. The present invention would most likely utilize single-chain antibodies expressed from expression vectors, as described below.

"Humanized" antibodies are also contemplated, as are chimeric antibodies from mouse, rat, or other species, bearing human constant and/or variable region domains, bispecific antibodies, recombinant and engineered antibodies and fragments thereof. Methods for the development of antibodies that are "custom-tailored" to the patient's dental disease are likewise known and such custom-tailored antibodies are also contemplated.

G. Peptides

Peptides may prove to be useful inhibitors of Bright/ARID3a function by competing with or mimicking Bright domains that bind or interact with DNA, Btk, TFII-I or other molecules, or compete with Bright dimerization sequences. Also contemplated are regions of Bright that comprise nuclear shuttling sequences. Bright-derived peptides are therefore a particular type of compound that may prove useful in inhibiting Bright function. The peptides may be designed around an existing structure, i.e., portions of Bright, or they may be selected for function from a randomized library.

Of particular interest is a region of SEQ ID NO:1 from about residue 444 to residue 549, and more particularly from 449-544. This region has been shown to be involved in Brigth/ARID3a dimerization, and also to contain nuclear shuttling sequences. Within these region, all possible peptides of 8 to about 40 residues are contemplated. Other more particular regions include residues 444-483, 449-488, 510-549, 505-544, 444-473, 449-473, 531-549 and 531-544. Particular peptides are illustrated in Table 2.

In general, the peptides will be less than 50 residues, and comprising at least about 10 consecutive residues of Bright/ARID3a. The number of consecutive Bright/ARID3a residues may be 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, with additional non-Bright sequences attached thereto. Ranges of peptide length of 10-50 residues, 10-40 residues, 15-50 residues 15-40, residues, 15-35 residues, 15-30 residues, 15-25 residues, 15-20 residues and 20-25 residues are contemplated. The number of additional non-Bright/ARID3a residues may be 5, 6, 7, 8, 9, 10, 11, 12, 13, 14, 15, 16, 17, 18, 19, 20 or more residues. The overall size of the peptides may therefore range from 8 reisudes to 75 or more residues, with 10-70 residues, 10-60 residues, 10-50 residues, 10-40 residues, 10-30 residues and 15-70 residues, 15-60 residues, 15-50 residues, 15-40 residues, 15-30 residues, 20-70 residues, 20-60 residues, 20-50 residues, 20-40 residues, and 20-30 residues being specifically contemplated ranges.

Peptides may be produced by cleavage of polypeptides, such as Bright, with proteolytic enzymes (trypsin, chymotrypsin, etc.), or chemicals. They may also be produced recombinantly using vectors and techniques described supra. However, it may be be most advantageous to produce peptides using the solid-phase synthetic techniques (Merrifield, 1963). Other peptide synthesis techniques are well known to those of skill in the art (Bodanszky et al., 1976; Peptide Synthesis, 1985; Solid Phase Peptide Synthelia, 1984). Appropriate protective groups for use in such syntheses will be found in the above texts, as well as in Protective Groups in Organic Chemistry, 1973. These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

Aside from the twenty standard amino acids can be used, there are a vast number of "non-standard" amino acids. Two of these can be specified by the genetic code, but are rather rare in proteins. Selenocysteine is incorporated into some proteins at a UGA codon, which is normally a stop codon. Pyrrolysine is used by some methanogenic archaea in enzymes that they use to produce methane. It is coded for with the codon UAG. Examples of non-standard amino acids that are not found in proteins include lanthionine, 2-aminoisobutyric acid, dehydroalanine and the neurotransmitter gamma-aminobutyric acid. Non-standard amino acids often occur as intermediates in the metabolic pathways for standard amino acids—for example ornithine and citrulline occur in the urea cycle, part of amino acid catabolism. Non-standard amino acids are usually formed through modifications to standard amino acids. For example, homocysteine is formed through the transsulfuration pathway or by the demethylation of methionine via the intermediate metabolite S-adenosyl methionine, while hydroxyproline is made by a posttranslational modification of proline.

The present invention may utilize L-configuration amino acids, D-configuration amino acids, or a mixture thereof. While L-amino acids represent the vast majority of amino acids found in proteins, D-amino acids are found in some proteins produced by exotic sea-dwelling organisms, such as cone snails. They are also abundant components of the peptidoglycan cell walls of bacteria. D-serine may act as a neurotransmitter in the brain. The L and D convention for amino acid configuration refers not to the optical activity of the amino acid itself, but rather to the optical activity of the isomer of glyceraldehyde from which that amino acid can theoretically be synthesized (D-glyceraldehyde is dextrorotary; L-glyceraldehyde is levorotary).

One form of an "all-D" peptide is a retro-inverso peptide. Retro-inverso modification of naturally occurring polypeptides involves the synthetic assemblage of amino acids with α-carbon stereochemistry opposite to that of the corresponding L-amino acids, i.e., D-amino acids in reverse order with respect to the native peptide sequence. A retro-inverso analogue thus has reversed termini and reversed direction of peptide bonds (NH—CO rather than CO—NH) while approximately maintaining the topology of the side chains as in the native peptide sequence. See U.S. Pat. No. 6,261,569, incorporated herein by reference.

Peptides may advantageously be attached or fused to certain additional peptide segments for beneficial properties associated therewith. In particular, such domains are cell delivery domains (also called a cell delivery vector, or cell transduction domain). These types of domains are well known in the art and are generally characterized as short amphipathic or cationic peptides and peptide derivatives, often containing multiple lysine and arginine resides (Fischer, 2007). Of particular interest are poly-D-Arg and poly-D-Lys sequences (e.g., dextrorotary residues, eight residues in length). Others are listed below in Table 2.

TABLE 2

| CDD/CTD PEPTIDES | SEQ ID NO |
|---|---|
| QAATATRGRSAASRPTERPRAPARSASRPRRPVE | 5 |
| RQIKIWFQNRRMKWKK | 6 |
| RRMKWKK | 7 |
| RRWRRWWRRWWRRWRR | 8 |
| RGGRLSYSRRRFSTSTGR | 9 |
| YGRKKRRQRRR | 10 |
| RKKRRQRRR | 11 |
| YARAAARQARA | 12 |
| RRRRRRRR | 13 |
| KKKKKKKK | 14 |
| GWTLNSAGYLLGKINLKALAALAKXIL | 15 |
| LLILLRRRIRKQANAHSK | 16 |
| SRRHHCRSKAKRSRHH | 17 |
| NRARRNRRRVR | 18 |
| RQLRIAGRRLRGRSR | 19 |
| KLIKGRTPIKFGK | 20 |
| RRIPNRRPRR | 21 |
| KLALKLALKALKAALKLA | 22 |
| KLAKLAKKLAKLAK | 23 |
| GALFLGFLGAAGSTNGAWSQPKKKRKV | 24 |
| KETWWETWWTEWSQPKKKRKV | 25 |
| GALFLGWLGAAGSTMGAKKKRKV | 26 |
| MGLGLHLLVLAAALQGAKSKRKV | 27 |
| AAVALLPAVLLALLAPAAANYKKPKL | 28 |
| MANLGYWLLALFVTMWTDVGLCKKRPKP | 29 |
| LGTYTQDFNKFHTFPQTAIGVGAP | 30 |
| DPKGDPKGVTVTVTVTGKGDPXPD | 31 |
| PPPPPPPPPPPPPP | 32 |
| VRLPPPVRLPPPVRLPPP | 33 |
| PRPLPPPRPG | 34 |
| SVRRRPRPPYLPRPRPPPFFPPRLPPRIPP | 35 |
| TRSSRAGLQFPVGRVHRLLRK | 36 |
| GIGKFLHSAKKFGKAFVGEIMNS | 37 |
| KWKLFKKIEKVGQNIRDGIIKAGPAVAVVGQATQIAK | 38 |
| ALWMTLLKKVLKAAAKAALNAVLVGANA | 39 |
| GIGAVLKVLTTGLPALISWIKRKRQQ | 40 |

TABLE 2-continued

| CDD/CTD PEPTIDES | SEQ ID NO |
|---|---|
| INLKALAALAKKIL | 41 |
| GFFALIPKIISSPLPKTLLSAVGSALGGSGGQE | 42 |
| LAKWALKQGFAKLKS | 43 |
| SMAQDIISTIGDLVKWIIQTVNXFTKK | 44 |
| LLGDFFRKSKEKIGKEFKRIVQRIKQRIKDFLANLVPRTES | 45 |
| LKKLLKKLLKKLLKKLLKKL | 46 |
| KLKLKLKLKLKLKLKLKL | 47 |
| PAWRKAFRWAWRMLKKAA | 48 |

Linkers or cross-linking agents may be used to fuse peptides to other proteinaceous sequences. Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g. amino, sulfhydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterobifunctional cross-linking reagents and methods of using the cross-linking reagents are described in U.S. Pat. No. 5,889,155, specifically incorporated herein by reference in its entirety. The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides. In instances where a particular peptide does not contain a residue amenable for a given cross-linking reagent in its native sequence, conservative genetic or synthetic amino acid changes in the primary sequence can be utilized.

Peptides modified for in vivo use by the addition, at the amino- and/or carboxyl-terminal ends, of a blocking agent to facilitate survival of the peptide in vivo are contemplated. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. These agents can be added either chemically during the synthesis of the peptide, or by recombinant DNA technology by methods familiar in the art. Alternatively, blocking agents such as pyroglutamic acid or other molecules known in the art can be attached to the amino and/or carboxyl terminal residues.

The inventors also contemplate that certain non-natural amino acids that satisfy the structural constraints of the inhibitory peptides of the present invention without a loss, and perhaps with an improvement in, biological function. In addition, the present inventors also contemplate that structurally similar compounds may be formulated to mimic the key portions of Bright/ARID3a. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Methods for generating specific structures have been disclosed in the art. For example, α-helix mimetics are disclosed in U.S. Pat. Nos. 5,446,128; 5,710,245; 5,840,833; and 5,859,184. Methods for generating conformationally restricted β-turns and β-bulges are described, for example, in U.S. Pat. Nos. 5,440,013; 5,618,914; and 5,670,155. Other types of mimetic turns include reverse and γ-turns. Reverse turn mimetics are disclosed in U.S. Pat. Nos. 5,475,085 and 5,929,237, and γ-turn mimetics are described in U.S. Pat. Nos. 5,672,681 and 5,674,976.

By "molecular modeling" is meant quantitative and/or qualitative analysis of the structure and function of protein-protein physical interaction based on three-dimensional structural information and protein-protein interaction models. This includes conventional numeric-based molecular dynamic and energy minimization models, interactive computer graphic models, modified molecular mechanics models, distance geometry and other structure-based constraint models. Molecular modeling typically is performed using a computer and may be further optimized using known methods. Computer programs that use X-ray crystallography data are particularly useful for designing such compounds. Programs such as RasMol, for example, can be used to generate three dimensional models. Computer programs such as INSIGHT (Accelrys, Burlington, Mass.), GRASP (Anthony Nicholls, Columbia University), Dock (Molecular Design Institute, University of California at San Francisco), and Auto-Dock (Accelrys) allow for further manipulation and the ability to introduce new structures. The methods can involve the additional step of outputting to an output device a model of the 3-D structure of the compound. In addition, the 3-D data of candidate compounds can be compared to a computer database of, for example, 3-D structures.

Compounds of the invention also may be interactively designed from structural information of the compounds described herein using other structure-based design/modeling techniques (see, e.g., Jackson, 1997; Jones et al., 1996). Candidate compounds can then be tested in standard assays familiar to those skilled in the art. Exemplary assays are described herein.

The 3-D structure of biological macromolecules (e.g., proteins, nucleic acids, carbohydrates, and lipids) can be determined from data obtained by a variety of methodologies. These methodologies, which have been applied most effectively to the assessment of the 3-D structure of proteins, include: (a) x-ray crystallography; (b) nuclear magnetic resonance (NMR) spectroscopy; (c) analysis of physical distance constraints formed between defined sites on a macromolecule, e.g., intramolecular chemical crosslinks between residues on a protein (e.g., PCT/US00/14667, the disclosure of which is incorporated herein by reference in its entirety), and (d) molecular modeling methods based on a knowledge of the primary structure of a protein of interest, e.g., homology modeling techniques, threading algorithms, or ab initio structure modeling using computer programs such as MONSSTER (Modeling Of New Structures from Secondary and Tertiary Restraints) (see, e.g., International Application No. PCT/US99/11913, the disclosure of which is incorporated herein by reference in its entirety). Other molecular modeling techniques may also be employed in accordance with this invention (e.g., Cohen et al., 1990; Navia et al., 1992), the disclosures of which are incorporated herein by reference in their entirety). All these methods produce data that are amenable to computer analysis. Other spectroscopic methods that can also be useful in the method of the invention, but that do not currently provide atomic level structural detail about biomolecules, include circular dichroism and fluorescence and ultraviolet/visible light absorbance spectroscopy. A particular method of analysis is x-ray crystallography.

H. Dominant-Negative Bright/ARID3a

Dominant-negative proteins are defective proteins with can negate the effects of normal, functional proteins when both are present in the same environment. In many cases, dominant-negative proteins homo-multimerize and are thus able to "poison" a complex that contains one or more functional proteins. Dominant-negative forms of Bright have been produced which act in just this manner. In designing dominant-negative Bright molecules, several regions present useful points for mutation. First, changes in the DNA binding domain (ARID) that block DNA binding produce dominant-negative effects. Second, alterations in the nuclear localization sequence which block nuclear translocation result in a dominant-negative form of Bright/ARID3a. Third, manipulation of the interaction and dimerization domains cause a dominant-negative function. Other dominant-negative proteins may be produced by interfering with the amino-terminal domain. Dominant-negative forms of Bright are described in Nixon et al. (2004).

VI. CULTURING STEM CELLS

In one aspect, the present invention addresses culturing of de-differentiated cells for expansion. In another aspect, the culturing of multipotent cells is performed for the purpose of re-differentiation. In addition, the present invention also contemplates the use of naturally-occurring or engineered cells that are Bright/ARID3a-defective to enhance the growth of natural ESCs. Such cells have proven to provide signals/factors that stimulate the growth/differentiation of stem cells in culture.

A. Cell Identification and Separation Techniques

Methods of separating ESCs from mixed cell populations are well known in the art and may be applied to the cell populations of the present invention. Cells purified in this fashion may then be used for genetic engineering/gene replacement therapy. Sources of such cells include, but are not limited to, bone marrow and chord blood. In addition, they can be used for tissue regeneration purposes. The following description sets forth exemplary methods for separation of stem cells based upon the surface expression of various markers.

i. Fluorescence Activated Cell Sorting (FACS)

FACS facilitates the quantitation and/or separation of subpopulations of cells based upon surface markers. Cells to be sorted are first tagged with a fluorescently labeled antibody or other marker specific ligand. Generally, labeled antibodies and ligands are specific for the expression of a phenotype specific cell surface molecule. Alternatively, cells may be labeled internally. The labeled cells are then passed through a laser beam and the fluorescence intensity of each cell determined. The sorter distributes the positive and negative cells into label-plus and label-minus wells at a flow rate of approximately 3000-10,000 cells per second.

The use of multiple fluorescent tags exciting at different wavelengths allows for sorting based upon multiple or alternate criteria. Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red. Thus, for example, a single PBMC sample may be analyzed with alternatively labeled anti-Ig antibody, anti-CD3 antibody, anti-CD8 antibody and anti-CD4 antibody to screen for the presence of B cells and T cells within the sample, as well as distinguishing specific T cell subsets.

FACS analysis and cell sorting is carried out on a flow cytometer. A flow cytometer generally consists of a light source, normally a laser, collection optics, electronics and a computer to translate signals to data. Scattered and emitted fluorescent light is collected by two lenses (one positioned in front of the light source and one set at right angles) and by a series of optics, beam splitters and filters, which allow for specific bands of fluorescence to be measured.

Flow cytometer apparatus permit quantitative multiparameter analysis of cellular properties at rates of several thousand cells per second. These instruments provide the ability to differentiate among cell types. Data are often displayed in one-dimensional (histogram) or two-dimensional (contour plot, scatter plot) frequency distributions of measured variables. The partitioning of multiparameter data files involves consecutive use of the interactive one- or two-dimensional graphics programs.

Quantitative analysis of multiparameter flow cytometric data for rapid cell detection consists of two stages: cell class characterization and sample processing. In general, the process of cell class characterization partitions the cell feature into cells of interest and not of interest. Then, in sample processing, each cell is classified in one of the two categories according to the region in which it falls. Analysis of the class of cells is very important, as high detection performance may be expected only if an appropriate characteristic of the cells is obtained. Also, one can use forward side scatter (granularity and size) for separative purposes.

Not only is cell analysis performed by flow cytometry, but so too is sorting of cells. In U.S. Pat. No. 3,826,364, an apparatus is disclosed which physically separates particles, such as functionally different cell types. In this machine, a laser provides illumination which is focused on the stream of particles by a suitable lens or lens system so that there is highly localized scatter from the particles therein. In addition, high intensity source illumination is directed onto the stream of particles for the excitation of fluorescent particles in the stream. Certain particles in the stream may be selectively charged and then separated by deflecting them into designated receptacles. A classic form of this separation is via fluorescent tagged antibodies, which are used to mark one or more cell types for separation.

Additional and alternate methods for performing flow cytometry and fluorescent antibody cell sorting are described in U.S. Pat. Nos. 4,284,412; 4,989,977; 4,498,766; 5,478,722; 4,857,451; 4,774,189; 4,767,206; 4,714,682; 5,160,974; and 4,661,913, herein expressly incorporated by reference.

ii. Micro-Bead Separation

Cells in suspension may be separated to very high purity according to their surface antigens using micro-bead technologies. The basic concept in micro-bead separations is to selectively bind the biomaterial of interest (e.g., a specific cell, protein, or DNA sequence) to a particle and then separate it from its surrounding matrix. Micro-bead separation involves contacting a cell suspension with a slurry of microbeads labeled with a cell surface specific antibody or ligand. Cells labeled with the micro-beads are then separated using an affinity capture method specific for some property of the beads. This format facilitates both positive and negative selection.

Magnetic beads are uniform, superparamagnetic beads generally coated with an affinity tag such as recombinant streptavidin that will bind biotinylated immunoglobulins, or other biotinylated molecules such as, for example, peptides/proteins or lectins. Magnetic beads are generally uniform micro- or nanoparticles of $Fe_3O_4$. These particles are superparamagnetic, meaning that they are attracted to a magnetic field but retain no residual magnetism after the field is removed. Suspended superparamagnetic particles tagged to a cell of interest can be removed from a matrix using a magnetic field, but they do not agglomerate (i.e., they stay suspended) after removal of the field.

A common format for separations involving superparamagnetic nanoparticles is to disperse the beads within the pores of larger microparticles. These microparticles are coated with a monoclonal antibody for a cell-surface antigen. The antibody-tagged, superparamagnetic microparticles are then introduced into a cellular suspension. The particles bind to cells expressing the surface antigen of interest and may be separated out with the application of a magnetic field. This may be facilitated by running the suspension over a high gradient magnetic separation column placed in a strong magnetic field. The magnetically labeled cells are retained in the column while non-labeled cells pass through. When the column is removed from the magnetic field, the magnetically retained cells are eluted. Both, labeled and non-labeled fractions can be completely recovered.

iii. Affinity Chromatography

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed elsewhere in this document.

iv. Surface Markers for Selection of ESCs

As discussed above, cell surface markers are often used to identify. Table 3, below, provides a list of markers and the ESC type with which they are most commonly associated, as well as markers for differentiated cells.

TABLE 3

Markers Commonly Used to Identify Stem Cells and to Characterize Differentiated Cell Types

| Marker Name | Cell Type | Significance |
| --- | --- | --- |
| Blood Vessel | | |
| Fetal liver kinase-1 (Flk1) | Endothelial | Cell-surface receptor protein that identifies endothelial cell progenitor; marker of cell-cell contacts |
| Smooth muscle cell-specific myosin heavy chain | Smooth muscle | Identifies smooth muscle cells in the wall of blood vessels |
| Vascular endothelial cell cadherin | Smooth muscle | Identifies smooth muscle cells in the wall of blood vessels |
| Bone | | |
| Bone-specific alkaline phosphatase (BAP) | Osteoblast | Enzyme expressed in osteoblast; activity indicates bone formation |
| Hydroxyapatite | Osteoblast | Minerlized bone matrix that provides structural integrity; marker of bone formation |
| Osteocalcin (OC) | Osteoblast | Mineral-binding protein uniquely synthesized by osteoblast; marker of bone formation |
| Bone Marrow and Blood | | |
| Bone morphogenetic protein receptor (BMPR) | Mesenchymal stem and progenitor cells | Important for the differentiation of committed mesenchymal cell types from mesenchymal stem and progenitor cells; BMPR identifies early mesenchymal lineages (stem and progenitor cells) |
| CD4 and CD8 | White blood cell (WBC) | Cell-surface protein markers specific for mature T lymphocyte (WBC subtype) |
| CD34 | Hematopoietic stem cell (HSC), satellite, endothelial progenitor | Cell-surface protein on bone marrow cell, indicative of a HSC and endothelial progenitor; CD34 also identifies muscle satellite, a muscle stem cell |
| CD34$^+$Sca1$^+$Lin$^-$ profile | Mesencyhmal stem cell (MSC) | Identifies MSCs, which can differentiate into adipocyte, osteocyte, chondrocyte, and myocyte |
| CD38 | Absent on HSC Present on WBC lineages | Cell-surface molecule that identifies WBC lineages. Selection of CD34$^+$/CD38$^-$ cells allows for purification of HSC populations |
| CD44 | Mesenchymal | A type of cell-adhesion molecule used to identify specific types of mesenchymal cells |
| c-Kit | HSC, MSC | Cell-surface receptor on BM cell types that identifies HSC and MSC; binding by fetal calf serum (FCS) enhances proliferation of ES cells, HSCs, MSCs, and hematopoietic progenitor cells |
| Colony-forming unit (CFU) | HSC, MSC progenitor | CFU assay detects the ability of a single stem cell or progenitor cell to give rise to one or more cell lineages, such as red blood cell (RBC) and/or white blood cell (WBC) lineages |
| Fibroblast colony-forming unit (CFU-F) | Bone marrow fibroblast | An individual bone marrow cell that has given rise to a colony of multipotent fibroblastic cells; such identified cells are precursors of differentiated mesenchymal lineages |
| Hoechst dye | Absent on HSC | Fluorescent dye that binds DNA; HSC extrudes the dye and stains lightly compared with other cell types |
| Leukocyte common antigen (CD45) | WBC | Cell-surface protein on WBC progenitor |

TABLE 3-continued

Markers Commonly Used to Identify Stem Cells and to Characterize Differentiated Cell Types

| Marker Name | Cell Type | Significance |
|---|---|---|
| Lineage surface antigen (Lin) | HSC, MSC Differentiated RBC and WBC lineages | Thirteen to 14 different cell-surface proteins that are markers of mature blood cell lineages; detection of Lin-negative cells assists in the purification of HSC and hematopoietic progenitor populations |
| Mac-1 | WBC | Cell-surface protein specific for mature granulocyte and macrophage (WBC subtypes) |
| Muc-18 (CD146) | Bone marrow fibroblasts, endothelial | Cell-surface protein (immunoglobulin superfamily) found on bone marrow fibroblasts, which may be important in hematopoiesis; a subpopulation of Muc-18+ cells are mesenchymal precursors |
| Stem cell antigen (Sca-1) | HSC, MSC | Cell-surface protein on bone marrow (BM) cell, indicative of HSC and MSC Bone Marrow and Blood cont. |
| Stro-1 antigen | Stromal (mesenchymal) precursor cells, hematopoietic cells | Cell-surface glycoprotein on subsets of bone marrow stromal (mesenchymal) cells; selection of Stro-1+ cells assists in isolating mesenchymal precursor cells, which are multipotent cells that give rise to adipocytes, osteocytes, smooth myocytes, fibroblasts, chondrocytes, and blood cells |
| Thy-1 | HSC, MSC | Cell-surface protein; negative or low detection is suggestive of HSC |
| Cartilage | | |
| Collagen types II and IV | Chondrocyte | Structural proteins produced specifically by chondrocyte |
| Keratin | Keratinocyte | Principal protein of skin; identifies differentiated keratinocyte |
| Sulfated proteoglycan | Chondrocyte | Molecule found in connective tissues; synthesized by chondrocyte |
| Fat | | |
| Adipocyte lipid-binding protein (ALBP) | Adipocyte | Lipid-binding protein located specifically in adipocyte |
| Fatty acid transporter (FAT) | Adipocyte | Transport molecule located specifically in adipocyte |
| Adipocyte lipid-binding protein (ALBP) | Adipocyte | Lipid-binding protein located specifically in adipocyte |
| General | | |
| Y chromosome | Male cells | Male-specific chromosome used in labeling and detecting donor cells in female transplant recipients |
| Karyotype | Most cell types | Analysis of chromosome structure and number in a cell |
| Liver | | |
| Albumin | Hepatocyte | Principal protein produced by the liver; indicates functioning of maturing and fully differentiated hepatocytes |
| B-1 integrin | Hepatocyte | Cell-adhesion molecule important in cell-cell interactions; marker expressed during development of liver |
| Nervous System | | |
| CD133 | Neural stem cell, HSC | Cell-surface protein that identifies neural stem cells, which give rise to neurons and glial cells |
| Glial fibrillary acidic protein (GFAP) | Astrocyte | Protein specifically produced by astrocyte |
| Microtubule-associated protein-2 (MAP-2) | Neuron | Dendrite-specific MAP; protein found specifically in dendritic branching of neuron |
| Myelin basic protein (MPB) | Oligodendrocyte | Protein produced by mature oligodendrocytes; located in the myelin sheath surrounding neuronal structures |
| Nestin | Neural progenitor | Intermediate filament structural protein expressed in primitive neural tissue |

TABLE 3-continued

Markers Commonly Used to Identify Stem Cells and to Characterize Differentiated Cell Types

| Marker Name | Cell Type | Significance |
|---|---|---|
| Neural tubulin | Neuron | Important structural protein for neuron; identifies differentiated neuron |
| Neurofilament (NF) | Neuron | Important structural protein for neuron; identifies differentiated neuron |
| Neurosphere | Embryoid body (EB), ES | Cluster of primitive neural cells in culture of differentiating ES cells; indicates presence of early neurons and glia |
| Noggin | Neuron | A neuron-specific gene expressed during the development of neurons |
| O4 | Oligodendrocyte | Cell-surface marker on immature, developing oligodendrocyte |
| O1 | Oligodendrocyte | Cell-surface marker that characterizes mature oligodendrocyte |
| Synaptophysin | Neuron | Neuronal protein located in synapses; indicates connections between neurons |
| Tau | Neuron | Type of MAP; helps maintain structure of the axon |
| Pancreas | | |
| Cytokeratin 19 (CK19) | Pancreatic epithelium | CK19 identifies specific pancreatic epithelial cells that are progenitors for islet cells and ductal cells |
| Glucagon | Pancreatic islet | Expressed by alpha-islet cell of pancreas |
| Insulin | Pancreatic islet | Expressed by beta-islet cell of pancreas Pancreas |
| Insulin-promoting factor-1 (PDX-1) | Pancreatic islet | Transcription factor expressed by beta-islet cell of pancreas |
| Nestin | Pancreatic progenitor | Structural filament protein indicative of progenitor cell lines including pancreatic |
| Pancreatic polypeptide | Pancreatic islet | Expressed by gamma-islet cell of pancreas |
| Somatostatin | Pancreatic islet | Expressed by delta-islet cell of pancreas |
| Pluripotent Stem Cells | | |
| Alkaline phosphatase | Embryonic stem (ES), embryonal carcinoma (EC) | Elevated expression of this enzyme is associated with undifferentiated pluripotent stem cell (PSC) |
| Alpha-fetoprotein (AFP) | Endoderm | Protein expressed during development of primitive endoderm; reflects endodermal differentiation Pluripotent Stem Cells |
| Bone morphogenetic protein-4 | Mesoderm | Growth and differentiation factor expressed during early mesoderm formation and differentiation |
| Brachyury | Mesoderm | Transcription factor important in the earliest phases of mesoderm formation and differentiation; used as the earliest indicator of mesoderm formation |
| Cluster designation 30 (CD30) | ES, EC | Surface receptor molecule found specifically on PSC |
| Cripto (TDGF-1) | ES, cardiomyocyte | Gene for growth factor expressed by ES cells, primitive ectoderm, and developing cardiomyocyte |
| GATA-4 gene | Endoderm | Expression increases as ES differentiates into endoderm |
| GCTM-2 | ES, EC | Antibody to a specific extracellular-matrix molecule that is synthesized by undifferentiated PSCs |
| Genesis | ES, EC | Transcription factor uniquely expressed by ES cells either in or during the undifferentiated state of PSCs |
| Germ cell nuclear factor | ES, EC | Transcription factor expressed by PSCs |
| Hepatocyte nuclear factor-4 (HNF-4) | Endoderm | Transcription factor expressed early in endoderm formation |
| Nestin | Ectoderm, neural and pancreatic progenitor | Intermediate filaments within cells; characteristic of primitive neuroectoderm formation |
| Neuronal cell-adhesion molecule (N-CAM) | Ectoderm | Cell-surface molecule that promotes cell-cell interaction; indicates primitive neuroectoderm formation |
| Pax6 | Ectoderm | Transcription factor expressed as ES cell differentiates into neuroepithelium |

TABLE 3-continued

Markers Commonly Used to Identify Stem Cells and to Characterize Differentiated Cell Types

| Marker Name | Cell Type | Significance |
| --- | --- | --- |
| Stage-specific embryonic antigen-3 (SSEA-3) | ES, EC | Glycoprotein specifically expressed in early embryonic development and by undifferentiated PSCs |
| Stage-specific embryonic antigen-4 (SSEA-4) | ES, EC | Glycoprotein specifically expressed in early embryonic development and by undifferentiated PSCs |
| Stem cell factor (SCF or c-Kit ligand) | ES, EC, HSC, MSC | Membrane protein that enhances proliferation of ES and EC cells, hematopoietic stem cell (HSCs), and mesenchymal stem cells (MSCs); binds the receptor c-Kit |
| Telomerase | ES, EC | An enzyme uniquely associated with immortal cell lines; useful for identifying undifferentiated PSCs |
| TRA-1-60 | ES, EC | Antibody to a specific extracellular matrix molecule is synthesized by undifferentiated PSCs |
| TRA-1-81 | ES, EC | Antibody to a specific extracellular matrix molecule normally synthesized by undifferentiated PSCs |
| Vimentin | Ectoderm, neural and pancreatic progenitor | Intermediate filaments within cells; characteristic of primitive neuroectoderm formation |
| Skeletal Muscle/Cardiac/Smooth Muscle | | |
| MyoD and Pax7 | Myoblast, myocyte | Transcription factors that direct differentiation of myoblasts into mature myocytes |
| Myogenin and MR4 | Skeletal myocyte | Secondary transcription factors required for differentiation of myoblasts from muscle stem cells |
| Myosin heavy chain | Cardiomyocyte | A component of structural and contractile protein found in cardiomyocyte |
| Myosin light chain | Skeletal myocyte | A component of structural and contractile protein found in skeletal myocyte |

B. Cells and Cell Culture

Stem cells are generally defined as having both the capacity to self-renew (make more stem cells by cell division) as well as being able to differentiate into mature, specialized cells. A progenitor cell is an early descendant of a stem cell that can only differentiate, but it cannot renew itself anymore. In contrast, a stem cell can renew itself (make more stem cells by cell division) or it can differentiate (divide and with each cell division evolve more and more into different types of cells). A progenitor cell is often more limited in the kinds of cells it can become than a stem cell. In scientific terms, it is said that progenitor cells are more differentiated than stem cells.

Cell culture facilitates the maintenance and propagation of cells in vitro under controlled conditions. Cells may be cultured in a variety of types of vessels constructed of, for example, glass or plastic. The surfaces of culture vessels may be pre-treated or coated with, for example, gelatin, collagen, polylysine, or components of the extracellular matrix, to facilitate the cellular adherence. Some sophisticated techniques utilize entire layers of adherent cells, feeder cells, which are used to support the growth of cells with more demanding growth requirements.

Cells are normally cultured under conditions designed to closely mimic those observed in vivo. In order to mimic the normal physiological environment cells are generally incubated in a $CO_2$ atmosphere with semi-synthetic growth media. Culture media is buffered and contains, among other things, amino acids, nucleotides, salts, vitamins, and also a supplement of serum such as fetal calf serum (FCS) horse serum or even human serum. Culture media may be further supplemented with growth factors and inhibitors such as hormones, transferrin, insulin, selenium, and attachment factors.

As a rule, cells grown in vitro do not organize themselves into tissues. Instead, cultured cells grow as monolayers (or in some instances as multilayers) on the surface of tissue culture dishes. The cells usually multiply until they come into contact with each other to form a monolayer and stop growing when they come into contact with each other due to contact inhibition.

Anchorage-dependent cells show the phenomenon of adherence, i.e., they grow and multiply only if attached to the inert surface of a culture dish or another suitable support. Such cells cannot normally be grown without a solid support. Many cells do not require this solid surface and show a phenomenon known as Anchorage-independent growth. Accordingly, one variant of growing these cells in culture is the use of Spinner cultures or suspension cultures in which single cells float freely in the medium and are maintained in suspension by constant stirring or agitation. This technique is particularly useful for growing large amounts of cells in batch cultures.

Anchorage-independent cells are usually capable of forming colonies in semisolid media (e.g., matrigel). Some techniques have been developed that can be used also to grow anchorage-dependent cells in spinner cultures. They make use of microscopically small positively-charged dextran beads to which these cells can attach.

The starting material for the establishment of a cell culture may be tissue from a suitable donor obtained under sterile conditions. The tissues may be minced and treated with proteolytic enzymes such as trypsin, collagenase of dispase to obtain a single cell suspension that can be used to inoculate a culture dish. In some cases dispersion of tissue is also effectively achieved by treatment with buffers containing EDTA. A particular form of initiating a cell culture is the use of tiny pieces of tissues from which cells may grow out in vitro.

Primary cell cultures maintained for several passages may undergo ascrisis. Ascrisis is usually associated with alterations of the properties of the cells and may proceed quickly or extend over many passages. Loss of contact inhibition is frequently an indication of cells having lost their normal characteristics. These cells then grow as multilayers in tissue culture dishes. The most pronounced feature of abnormal cells is the alteration in chromosome numbers, with many cells surviving this process being aneuploid. The switch to abnormal chromosome numbers is usually referred to as cell transformation and this process may give rise to cells that can then be cultivated for indefinite periods of time by serial passaging. Transformed cells give rise to continuous cell lines.

In certain aspects of the instant invention, cells are cultured with differentiating agents. Cells will be cultured under specified conditions to achieve particular types of differentiation, and provided various factors necessary to facilitate the desired differentiation.

C. Cell Growth and (Re)Differentiation

Cell growth and differentiation factors are molecules that stimulate cells to proliferate, first while being maintained in a multipotent state, and second, to induce (re)differentiation. Leukemia inhibitory factor (LIF) may be utilized to impede spontaneous differentiation. In addition, culturing with factors to promote growth and differentiation of multipotent cells into functionally mature forms can be undertaken. Administration of the growth and/or differentiation factors may be repeated as needed.

It is envisioned that a growth and/or differentiation factor may constitute a hormone, cytokine, chemokine, hematopoietin, colony stimulating factor, interleukin, interferon, growth factor, other endocrine factor or combination thereof that act as intercellular mediators. Examples of such intercellular mediators are lymphokines, monokines, growth factors and traditional polypeptide hormones. Included among the growth factors are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factors-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte/macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12; IL-13, IL-14, IL-15, IL-16, IL-17, IL-18. Also contemplated are CD14 or signal transducers of the MyD88 pathway. As used herein, the term growth and/or differentiation factors include proteins from natural sources or from recombinant cell culture and biologically active equivalents of the native sequence, including synthetic molecules and mimetics.

In culturing natural stem cells or de-differentiated cells of the present invention, it may be desirable to use a support. One support is BD Biosciences Matrigel™ Basement Membrane Mix. This material can be used for (re)differentiation of hepatocytes, epithelial cells, endothelial, smooth muscle cells and neurons (Biederer & Scheiffele, 2007; Li et al., 2005; Hadley et al., 1985; Ireland, 1997; McGuire & Orkin, 1987; Bissel, et al., 1987; Page et al., 2007; Li et al., 1987; Barcellof et al., 1989; Roskelley et al., 1994; Xu et al., 2007; Debnath et al., 2003; Muthuswamy et al., 2001; Madison et al., 1985; Xu et al., 1994; Fouad et al., 2005). Other (re)differentiation methods would seek to induce pancreatic cell and hematopoietic cell phenotypes.

The vitamin A derivative, retinoic acid, can be used to differentiate B cells (Chen et al., 2008) and neuronal cells (Guan et al., 2001). In addition, Fico et al. (2008) provide methods and compositions useful for single step differentiation of neurons. The relevant teachings of these papers are incorporated by reference herein.

VII. VECTORS FOR CLONING, GENE TRANSFER AND EXPRESSION

Within certain embodiments, expression vectors are employed to express various products including Bright, peptides, dominant negative Bright proteins, antibodies or fragments thereof, antisense molecules, ribozymes or interfering RNAs. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

A. Regulatory Elements

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

In certain embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In certain embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product. Tables 2 and 3 list several regulatory elements that may be employed, in the context of the present invention, to regulate the expression of the gene of interest. This list is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene of interest in an expression construct (Table 4 and Table 5). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 4

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987a |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |

TABLE 4-continued

Promoter and/or Enhancer

| Promoter/Enhancer | References |
|---|---|
| Neural Cell Adhesion Molecule (NCAM) | Hirsh et al., 1990 |
| $\alpha_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 5

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Ponta et al., 1985; Sakai et al., 1988 |
| β-Interferon | poly(rI) × poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |
| Tet On/Off | Tetracycline | Clontech |

Of particular interest from the above list are promoters/regulatory regions that are inducible. The present invention contemplates the use of vectors that can be delivered to cells to express an inhibitor of Bright/ARID3a when induced, but upon removal of the inducing agent, the Bright/ARID3a inhibition is relieved and the cell may differentiate and lose immortality, optionally for the purpose of reimplantation in an individual.

The present inventors contemplate the use of retroviral and lentiviral vectors for delivery of nucleic acids, and thus they envision use of the endogenous promoters in these vectors.

B. Poly-A and Termination Signals

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

C. Selectable Markers

In certain embodiments of the invention, the cells contain nucleic acid constructs of the present invention, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin, histidinol, GFP, and lacZ are useful selectable markers. Alternatively, enzymes such as herpes simplex virus thymidine kinase (tk) chloramphenicol acetyltransferase (CAT), or HAT selection may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

D. Multigene Constructs and IRES

In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

E. Delivery of Expression Vectors

There are a number of ways in which expression vectors may be introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

i. Adenoviral Vectors

One particular mode of in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors, as described by Karlsson et al. (1986), or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$-$10^{12}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

ii. Retrovirus/Lentivirus

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

An approach designed to allow specific targeting of retrovirus vectors was developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

iii. Other Vectors

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

Epstein-Barr virus, frequently referred to as EBV, is a member of the herpesvirus family and one of the most common human viruses. The virus occurs worldwide, and most people become infected with EBV sometime during their lives. In the United States, as many as 95% of adults between 35 and 40 years of age have been infected. When infection with EBV occurs during adolescence or young adulthood, it causes infectious mononucleosis 35% to 50% of the time. EBV vectors have been used to efficiently deliver DNA sequences to cells, in particular, to B lymphocytes. Robertson et al. (1986) provides a review of EBV as a gene therapy vector.

With the recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al., introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

iv. Non-Viral Methods

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type by any number of receptor-ligand systems with or without liposomes. For example, epidermal growth factor (EGF) may be used as the receptor for mediated delivery of a nucleic acid into cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

VIII. KITS

For use in the applications described herein, kits are also within the scope of the invention. Such kits can comprise a carrier, package or container that is compartmentalized to receive one or more containers such as vials, tubes, and the like, each of the container(s) comprising one of the separate elements to be used in the method, in particular, a Bright inhibitor. The kit of the invention will typically comprise the container described above and one or more other containers comprising materials desirable from a commercial end user standpoint, including buffers, diluents, filters, needles, syringes, and package inserts with instructions for use. In addition, a label can be provided on the container to indicate that the composition is used for a specific therapeutic application, and can also indicate directions for either in vivo or in vitro use, such as those described above. Directions and or other information can also be included on an insert which is included with the kit.

IX. EXAMPLES

The following examples are included to further illustrate various aspects of the invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Provisional Data

Figure 2:
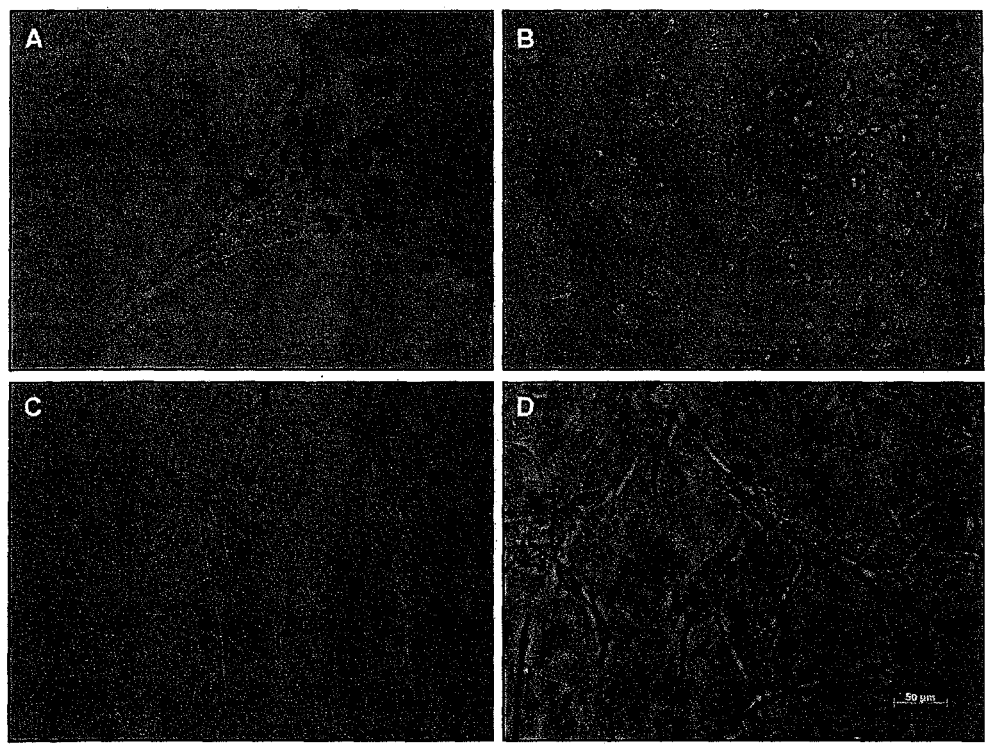
FIGS. 2A-D—ARID3a-deficient cells differentiate into multiple cell types (nerve cells, endothelial cells, adipocytes).
Figure 3:
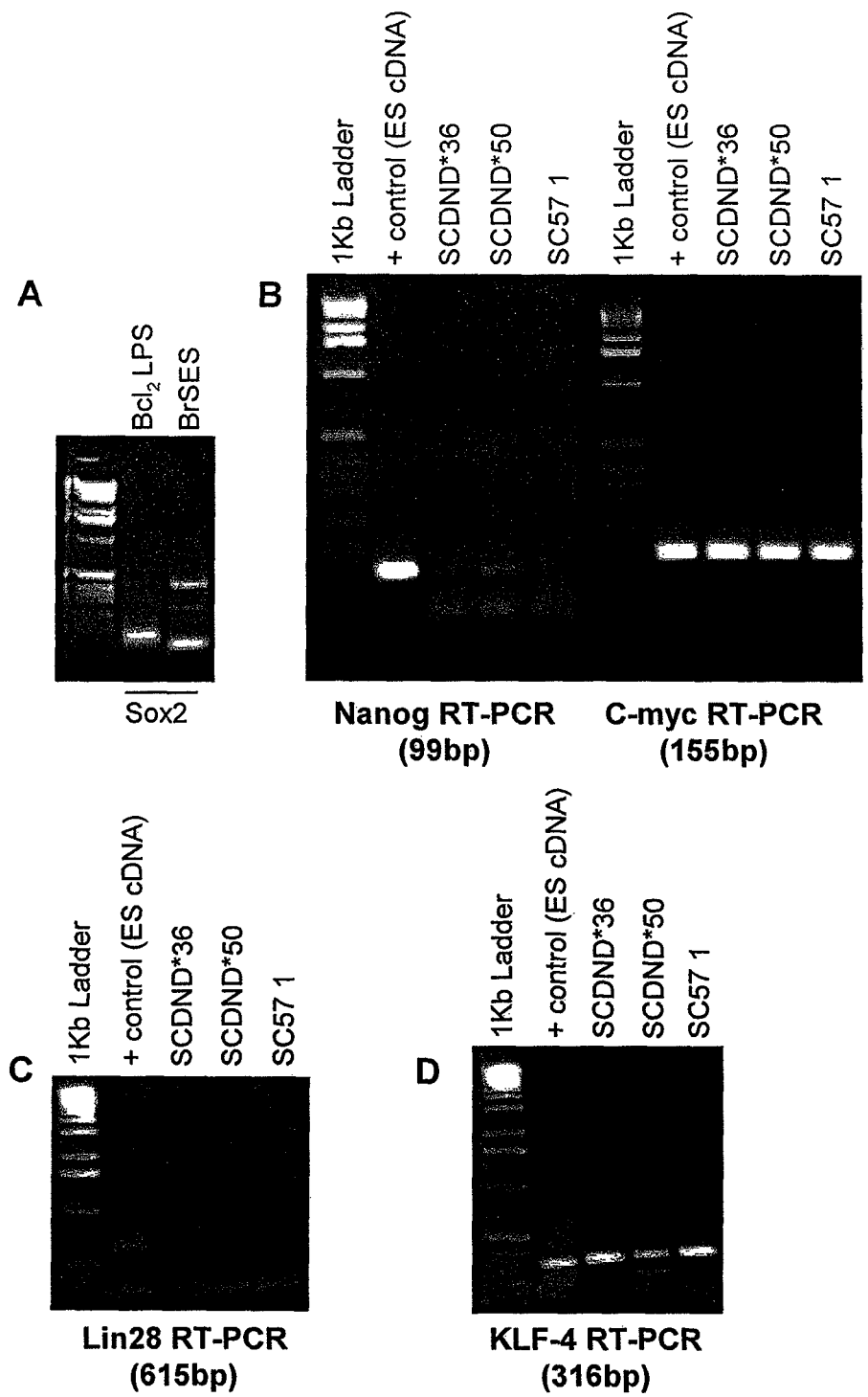
FIGS. 3A-D—Early stem cell gene markers are expressed in ARID3a-deficient cell cultures as shown by RT-PCR.

During analyses of transgenic mice expressing dominant-negative (DN) ARID3a, the inventors cultured whole spleen cells and discovered that the cells from these cultures had self-renewal potential that non-transgenic spleen cells did not have. Indeed, they were able to culture those cells for more than six months and noted that multiple cell types—adherent fibroblast-like and small lymphocyte-like—were maintained over time. Multiple surface markers were also present and unusual groupings of multiple cell types were maintained over time. Control splenic B cells died in about six weeks. Similarly, splenic cells from ARID3a-deficient mice maintained in 5% RPMI growth medium with normal additives (Ho et al., 2009) were found to spontaneously produce embryoid bodies (shown in FIG. 1) after several months of culture. Although multiple embryoid bodies were observed to spontaneously develop, particularly after periods of starvation, to date none have been observed to beat rhythmically as would be indicative of heart tissue. Multiple cell types were observed in these cultures as demonstrated by surface staining and microscopic observation (FIGS. 2A-D). Endothelial-like cells that express EPCR and other endothelial cell markers and form tube-like structures were readily produced from multiple ARID3a-deficient splenic sources (FIG. 2A). Other cells with distinct morphology were apparent in the same cultures (FIG. 2B). Cells from one of the original three spleen cultures have now been maintained for one year. None of the control cultures survived past two months.

The inventors have generated self-renewing pluripotent cells from seven ARID3a-deficient spleens, four ARID3a-deficient bone marrow cultures and one kidney culture. Therefore, ARID3a-deficiency appears to result in cells with self-renewing potential from multiple tissue sources. One of the bone marrow cultures has been tested in matrigel cultures for the ability to produce endothelial tubes, but instead gave rise to neural spheres and differentiated neuron-like cells over a two-three week culture period (FIGS. 2C-D). Bone marrow cultures also readily formed adipocyte and stromal cells (not shown). Kidney cultures contain multiple morphologically distinct cell types of currently unknown identity. These results are consistent with the idea that ARID3a inhibition results in out-growth of, or dedifferentiation into, stem cells capable of differentiating into multiple cell lineages.

Several gene products are known to be crucial for creating and/or maintaining stem cells, and these include Sox-2, Oct-4, myc, nanog, Klf4 and lin28. FIGS. 3A-D indicate that the inventors have observed Sox-2, nanog, myc, and Klf4 expression in their ARID-3a-deficient cultures, suggesting that early pluripotent cells are present. Surface stains for stem cell markers also demonstrate early stem cell lineage markers such as c-kit, sca-1 and CD9 (not shown). These data further indicate that pluripotent cells are present within these self-renewing cultures.

Supernatants from the pluripotent spleen cells were shown to be effective in inducing growth and differentiation of standard ES cell lines (FIG. 4). Thus, it is likely, that the pluripotent cells in ARID3a-deficient cultures produce chemokines and/or growth factors that enhance growth of stem cells. Such supernatants and/or purified growth factors may prove beneficial for growing standard available ES lines.

Figure 5:
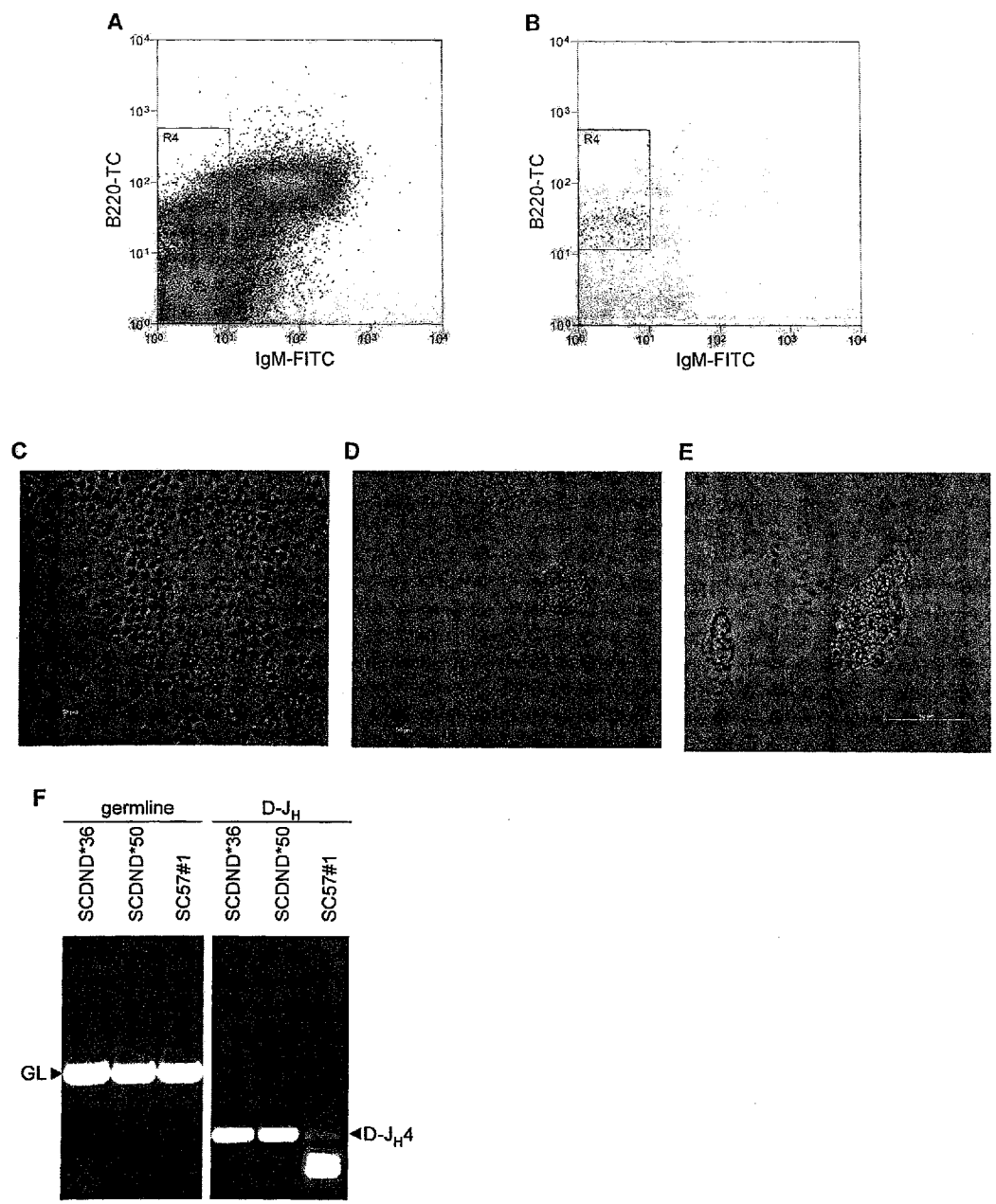
FIGS. 5A-F—Pluripotent stem cell production from B cells. Bone marrow pro-B cells from dominant-negative Bright transgenic mice were isolated by flow cytometry as CD43-IgM-B220+ cells (FIG. 5A) to >95% purity as shown by the post sort in (FIG. 5B). After 4 weeks of growth on irradiated murine embryonic fibroblasts with added LIF, the control C57Bl/6 background pre-B cells still resembled pre-B cells as shown in (FIG. 5C). Multicellular stem cell-like colonies were observed in the dominant-negative cultures even in the absence of LIF (FIGS. 5D and 5E).

Results using both knock-out and dominant-negative ARID3a tissues suggest that ARID3a deficiency is sufficient to cause spontaneous self-renewal and pluripotency, and suggest that stem cells can be produced from multiple adult tissues by ARID3a inhibition. FIGS. 5A-F show pluripotent stem cell production from B cells. Bone marrow pro-B cells from dominant-negative Bright transgenic mice were isolated by flow cytometry as CD43-IgM-B220+ cells (FIG. 5A) to >95% purity as shown by the post sort in (FIG. 5B). After 4 weeks of growth on irradiated murine embryonic fibroblasts with added LIF, the control C57Bl/6 background pre-B cells still resembled pre-B cells as shown in (FIG. 5C). Multicellular stem cell-like colonies were observed in the dominant-negative cultures even in the absence of LIF (FIGS. 5D and 5E). Amplification of genomic DNA from bulk splenic cultures from dominant-negative mice (SCDND*36 and 50) showed increased D-J rearrangement relative to control (SC57#1) cultures suggesting increased numbers of cells were derived from B cell progenitors.

Example 2

Materials & Methods

Mice.

Figure 15:
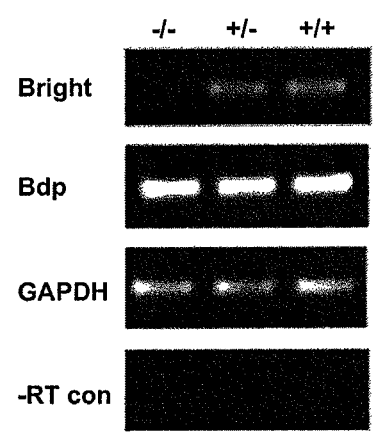
FIG. 15—Adult Bright$^{-/-}$ survivors express no Bright. Transcript expression of Bright and its ARID3b paralogue, Bdp, were evaluated in wild-type (+/+), heterozygous (±) and homozygous null (−/−) splenic B cells (source of highest Bright expression in adult mice) by RT-PCR. Bright mRNA was amplified for 30 cycles using primers which span exons 3 and 4 (forward 5'-GCGGACCCCAAGAGGAAAGAGTT (SEQ ID NO:3)) and (reverse 5'-CTGGGTGAGTAG-GCAAAGAGTGAGC (SEQ ID NO:4)) resulting in a 390 bp product. RT- and GAPDH loading controls are shown.

Conventional Bright$^{-/-}$ mice generated by standard targeting techniques in 129 sV ES cells using a strategy that eliminated exons1-7 to produce a null allele (FIG. 15) (provided by Dr. Philip Tucker, University of Texas at Austin). Greater than 99% of germline transmitted Bright/offspring died between E10.5-E13.5 from failed erythropoiesis. Rare adult homozygous survivors used in this study were 2-5 months old on a mixed C57BL6/129 sV background. DN Bright transgenic mice on the FVB/N background were previously described (Nixon et al., 2008) and have now been backcrossed ten generations onto C57Bl/6. Nod.CB17-Prkdc$^{scid}$/J mice were obtained from Jackson Laboratories. Animals were used with institutional approval and within review board-specified guidelines.

Tissue Culture and iPS Induction.

Whole spleen, kidney, lymph node or bone marrow from Bright$^{-/-}$ or DN transgenic mice were teased into single cell suspension and fed 2-3 times per week with RPMI 1640 containing 5% FBS and standard supplements (Webb et al., 1989). Mouse ES cells and iPS-like cells were grown with 10 ng/ml LIF on MEFs, and were passaged using trypsin as described (Meissner et al, 2009). Embryoid body formation and differentiation assays were performed using standard protocols (Meissner et al., 2009). MEFs were prepared from 129 sv mice as described (Meissner et al., 2009). Teratoma formation was induced by intramuscular injection of Nod/Scid mice with 2×10$^6$ cells. Surgically dissected tumors were paraffin-embedded, stained with heamatoxylin and eosin and evaluated by a licensed pathologist (S. Kosanke, OUHSC, OK).

Immunofluorescence Staining and Microscopy.

Cells were fixed in 4% PFA for 20 min at room temperature, washed and treated with PBS containing 5% donkey serum, 1% BSA (Sigma), and 0.1% Triton X-100 for 45 min at room temperature (Takahashi and Yamanaka, 2006; Takahashi et al., 2007). Primary antibodies were against Sox2 (MAB4343), Oct4 (MAB4305), SSEA1 (MAB4301), Nestin (MAB353), and βIII-T (CBL412) from Chemicon; Nanog (AF2729, R&D Systems) and α-SMA (N1584) and AFP (N1501) from Dako. Polyclonal rabbit and goat anti-Bright reagents were previously described (Herrscher et al., 1995; Nixon et al., 2004). Appropriate isotype controls and fluorophore-labeled secondary antibodies were purchased from Molecular Probes. DAPI was used for nuclear staining (D1306, Molecular Probes).

RT-PCR and Western Blotting.

Total RNA was isolated with the ArrayGrade Total RNA Isolation Kit (SABiosciences, Frederick, Md.), treated with DNase I (Promega, Madison, Wis.) and reverse transcribed using a First Strand Synthesis kit (Invitrogen) according to the manufacturers' protocols. Quantitative PCR was performed with SYBR Green/ROX qPCR Master Mix (SABiosciences, Frederick, Md.) and analyzed with the 7500 real-time PCR system (Applied Biosystems). Gene expression was normalized to GAPDH. Mouse Sox2 and Lin28 primers were 5'-GAAAGGAGAGAAGTTTGGAGCCC-3' (SEQ ID NO:49) and 5'-GCTGTTCTTCTGGTTGCCGC-3' (SEQ ID NO:50), and 5'-CCCTGGTGGTGTGTTCTGTATTGG-3' (SEQ ID NO:51) and 5'-TGGCAAGGGAAATATCA-CACAGC-3' (SEQ ID NO:52), respectively. Other human primers (Yu et al., 2007; Nixon et al., 2004; Park et al., 2008) and mouse primers (Tanaka et al., 2007; Liu et al., 2007; Kinoshita et al., 2007; Shaffer et al., 2002) were as described. Western blotting was performed with polyclonal anti-Bright and anti-actin as described (Nixon et al., 2008).

Lentivirus Production and Transduction.

shRNAs (Table 7) were subcloned into the pSIF-H1-copGFP lentiviral vector (System Biosciences, Mountain View, Calif.) and packaged by co-transfection with pFIV-34N and pVSV-G plasmids with the LipoD293™ DNA transfection reagent (SignaGen Laboratories, Gaithersburg, Md.) according to the manufacturer's protocol. Virus was harvested, filtered using a 0.45 µm sterile filter and concentrated by ultracentrifugation 48-72 hours later. Titers were determined by numbers of GFP-positive cells by flow cytometry. BCg3R-1d or 293T cells were treated with virus and 6 µg/ml polybrene (Sigma) for 24 hours. iPS-like cells were fed with ES medium (DMEM containing 20% FBS, 0.1 mM non-essential amino acid, and 0.1 mM β-mercaptoethanol) with 10 ng/ml LIF, and seeded onto irradiated MEF feeder cells in gelatin-coated plates. Medium was changed every other day.

Example 3

Results

With the exception of its contribution to IgH transcriptional activation in B lymphocytes (Rajaiya et al., 2006; Kaplan et al., 2001), Bright/ARID3a function has remained elusive. As with its orthologues in *Xenopus* and *Drosophila* (Shandala et al., 1999; Callery et al., 2005), null Bright mice died early in embryonic development. However, rare (<1%) Bright$^{-/-}$ mice survived lethality, and in vitro growth of their whole tissues resulted in long-lived, self-renewing cultures that maintained the ability to generate multiple cell types. Furthermore, similar cultures were established from tissue derived from transgenic mice expressing a dominant negative (DN) form of Bright which interferes with its DNA-binding function (Nixon et al., 2004; Nixon et al., 2008). Such cultures were readily maintained in normal RPMI 1640 media containing 5% FBS without any additional growth factors and could be produced from a wide variety of adult tissues, including spleen, bone marrow, lymph node and kidney. These cells exhibited contact inhibition, grew slowly and did not appear to be transformed. Yet, they could be recovered after freezing and could be maintained indefinitely (for >1 year, in some cases) in culture (Table 6). Cells from normal controls typically survived less than six weeks and were largely stroma-like in nature by the end of culture. These data suggest that loss of Bright function is sufficient to promote self-renewal.

Figure 6:
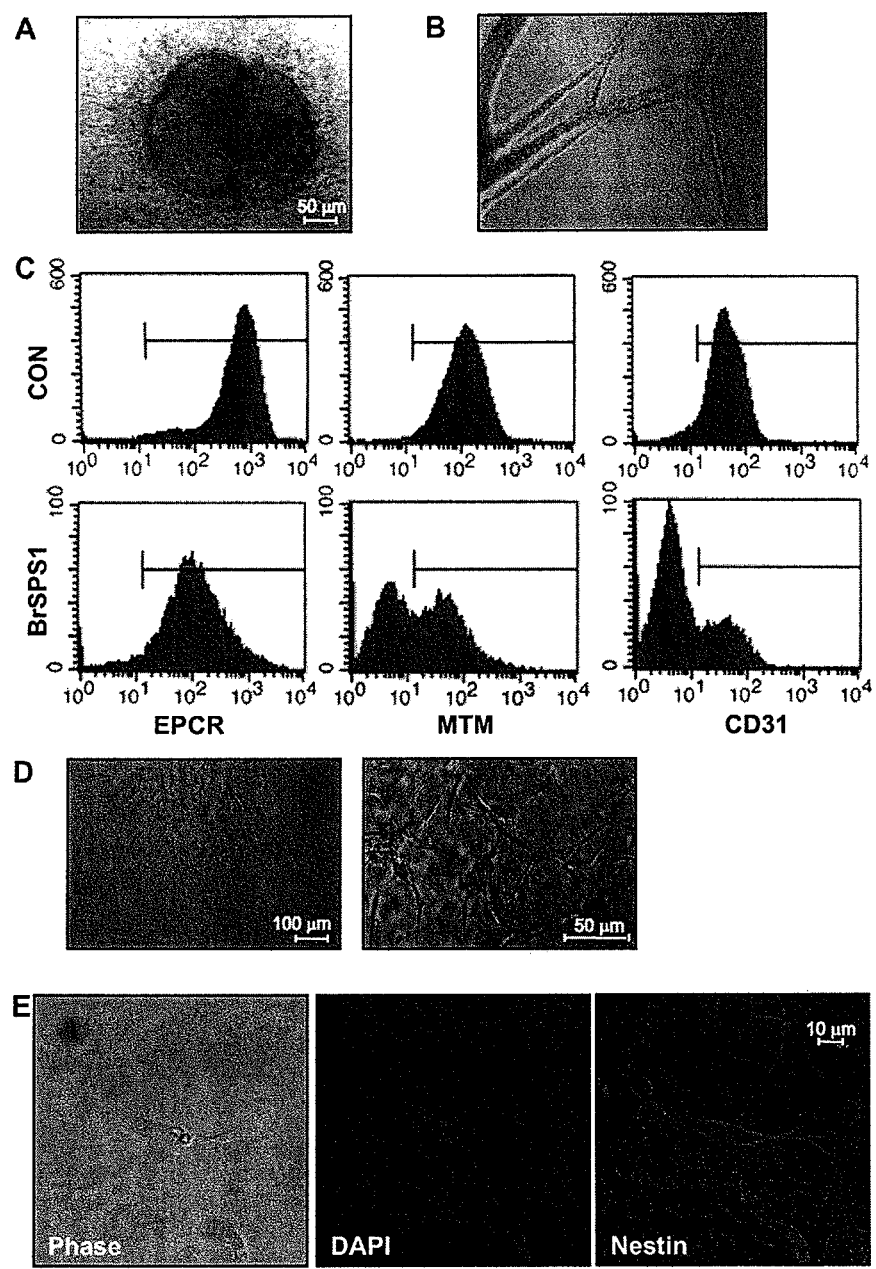
FIGS. 6A-E—Bright deficient cells are spontaneously multipotent.

The inventors observed that overgrown cultures from Bright$^{-/-}$ tissues spontaneously formed embryoid-like bodies that contained cells of multiple morphologies (FIG. 6A). Enriched media caused the bodies to spread, become attached to the culture dish, to disaggregate and to convert into multiple cell types with varying levels of differentiation. Bright$^{-/-}$ spleen lines spontaneously generated endothelial-like cells that grew in branched patterns. When these cultures were fed with growth media containing endothelial cell additives, including 1% brain food and heparin, the knock-out cells spontaneously formed tube-like structures (FIG. 6B) morphologically (Bakre et al., 2007) and immunohistochemically typical of differentiated endothelial cells (FIG. 6C). Three weeks after seeding into matrigel, Bright$^{-/-}$ bone marrow cultures formed large aggregates of neuron-like cells with long axon-like projections (FIG. 6D) that were positive for the early neuronal marker, nestin (FIG. 6E). Collectively, these data suggest that loss of Bright disrupts the normal differentiation patterns of cells such that they maintain an unexpected plasticity.

Because the inventors observed embryoid-like bodies and mature cell types representative of ectoderm and mesoderm lineages, they hypothesized that these Bright-deficient cultures might contain stem cells. That Bright expression was shown previously to increase rapidly following embryoid body differentiation (Wang et al., 2006) further supported this notion. As observed in FIG. 2A, several genes commonly associated with pluripotency were activated in Bright$^{-/-}$ tissues to levels comparable to those in ES cells. Nanog expression, not present in normal spleen-cell-derived cultures, was strongly induced in all Bright$^{-/-}$ cultures, whereas Sox2 showed variable up-regulation. Klf4 and c-myc transcripts were observed in both normal tissue controls and in Bright$^{-/-}$ cultures, while Oct4 and Lin28 expression were typically not observed in the mouse iPS-like cells. These data suggest that Bright$^{-/-}$ cells express a subset of iPS pluripotency markers.

Figure 7:
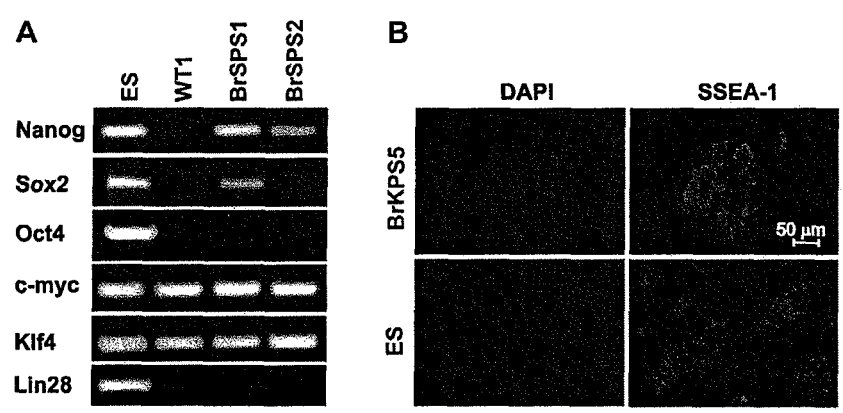
FIGS. 7A-B—Bright deficient cells form iPS-like colonies and express key stem cell markers.

Because these cultures spontaneously differentiated into multiple cell types under normal culture conditions, and thus differed in gene expression patterns over time, the inventors plated Bright$^{-/-}$ cells onto mouse embryonic fibroblast feeders (MEFs) in the presence of the differentiation inhibiting cytokine, leukemia inhibitory factor (LIF), as is done routinely for maintenance of normal ES and iPS cells. After a period of 4-6 weeks, the inventors were able to isolate clones with iPS-like morphology that expressed the ES cell markers SSEA-1 (FIG. 7B) and Nanog (not shown). These cells exhibited a stable iPS-like phenotype and indicate that iPS-like cells can be isolated from multiple tissues of Bright$^{-/-}$ mice.

Figure 8:
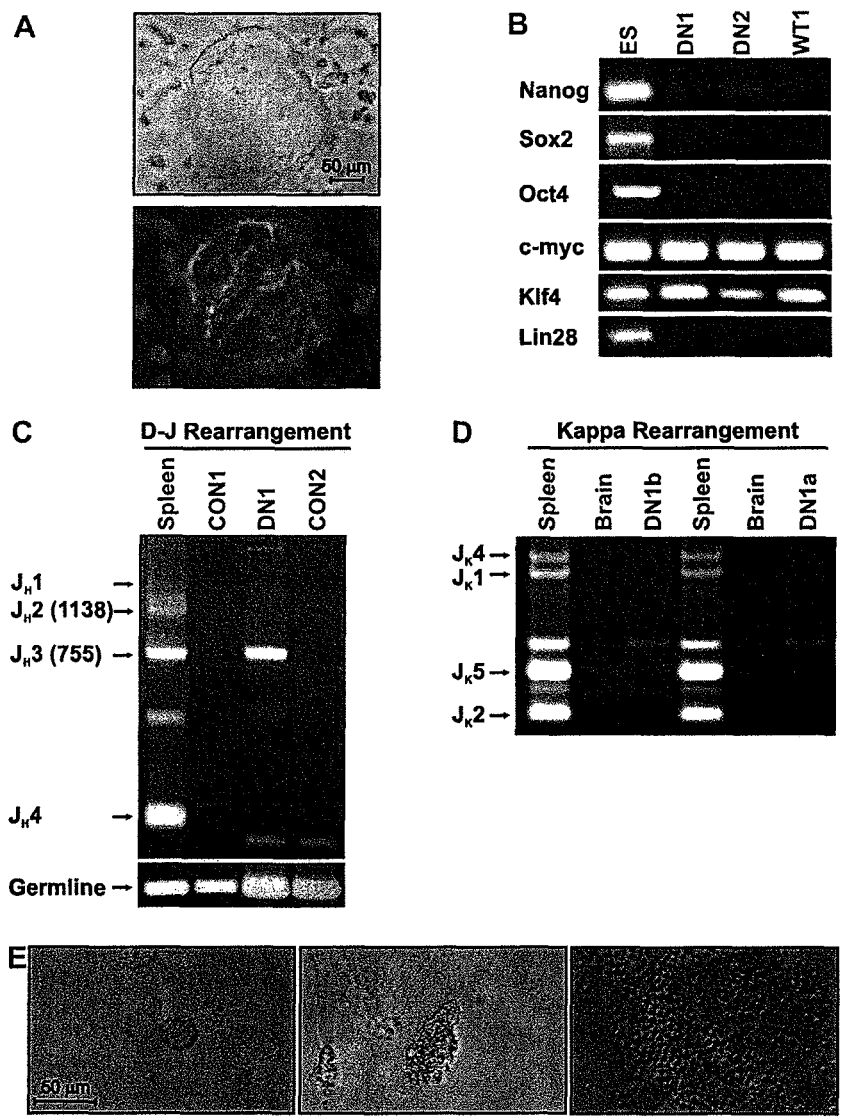
FIGS. 8A-E—DN Bright cell lines exhibit signs of reprogramming and appear to be B lymphocyte-derived.

Similarly, spleen and bone marrow from DN Bright transgenic mice exhibited the ability to spontaneously form embryoid-like bodies (FIG. 8A) and to spontaneously convert into cells with variable lineage surface marker expression (e.g., CD3, Mac-1, and GR-1; data not shown) and upregulation of Nanog (FIG. 8B). The inventors' transgenic mice express DN Bright from the B cell-specific CD19 promoter (Nixon et al., 2008). DN transgenic mice did not generate CD19$^+$ mature, DN Bright-expressing B cells (Nixon et al., 2008). Thus, instead of following normal B cell differentiation pathways, loss of Bright function may halt and reprogram these B lymphocytes. The failure of DN-derived, non-B cell containing tissues (e.g., kidney and liver) from these mice to exhibit self-renewing and long term growth potential is consistent with the hypothesis that self-renewing cells were derived from Bright-deficient B lymphocytes. In further support of the hypothesis, long term cell lines established from DN transgenic bone marrow and spleen exhibited D-J$_H$ rearrangements of their IgH loci (FIG. 8C, and not shown). PCR products demonstrating unrearranged germline bands were also present, and may result from unrearranged alleles or they may indicate the presence of non-B cell-derived stromal cells within the cultures. The inventors also detected evidence of κ light chain rearrangement (FIG. 8D) in the spleen-derived, but not the bone marrow-derived, DN Bright cultures, consistent with this compartment being composed predominantly of early B cells yet to rearrange the light chain loci.

Figure 11:
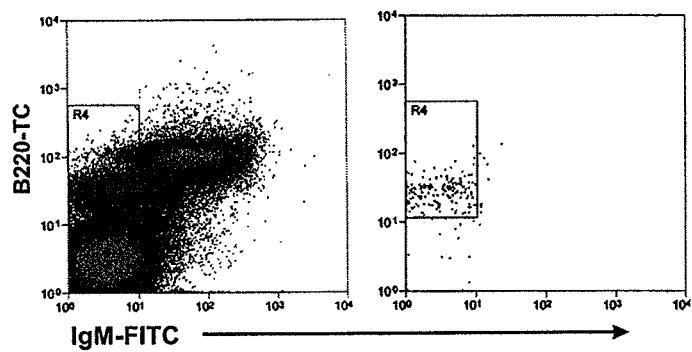
FIG. 11—Isolation of pre-B cells from bone marrow of DN Bright transgenic mice. CD43$^-$IgM$^-$B220$^{lo}$ DN Bright (left panel) and normal control pre-B cells (not shown) were sorted by flow cytometry and plated on MEFs in the presence of LIF. Post-sort analysis of the DN pre-B cells is shown (right panel).

The inventors sorted both DN transgenic and control C57Bl/6 pre-B cells (FIG. 11) and cultured them on MEFs in the presence of LIF. After 4 weeks in culture, some lymphocyte-like cells remained in the C57Bl/6 cultures, but the DN Bright pre-B cells had developed into colonies that morphologically resembled iPS cell colonies (FIG. 8E). These colonies were more difficult to carry continuously in culture and may require additional unidentified growth and/or other factors to facilitate their self-renewing potential. Additional factors were found to be critical for reprogramming B lineage cells using standard methodologies for iPS production (Hanna et al., 2008). Nonetheless, these data suggest that selective inhibition of Bright in B lineage cells also allows those cells to reprogram and convert into iPS-like cells.

Figure 9:
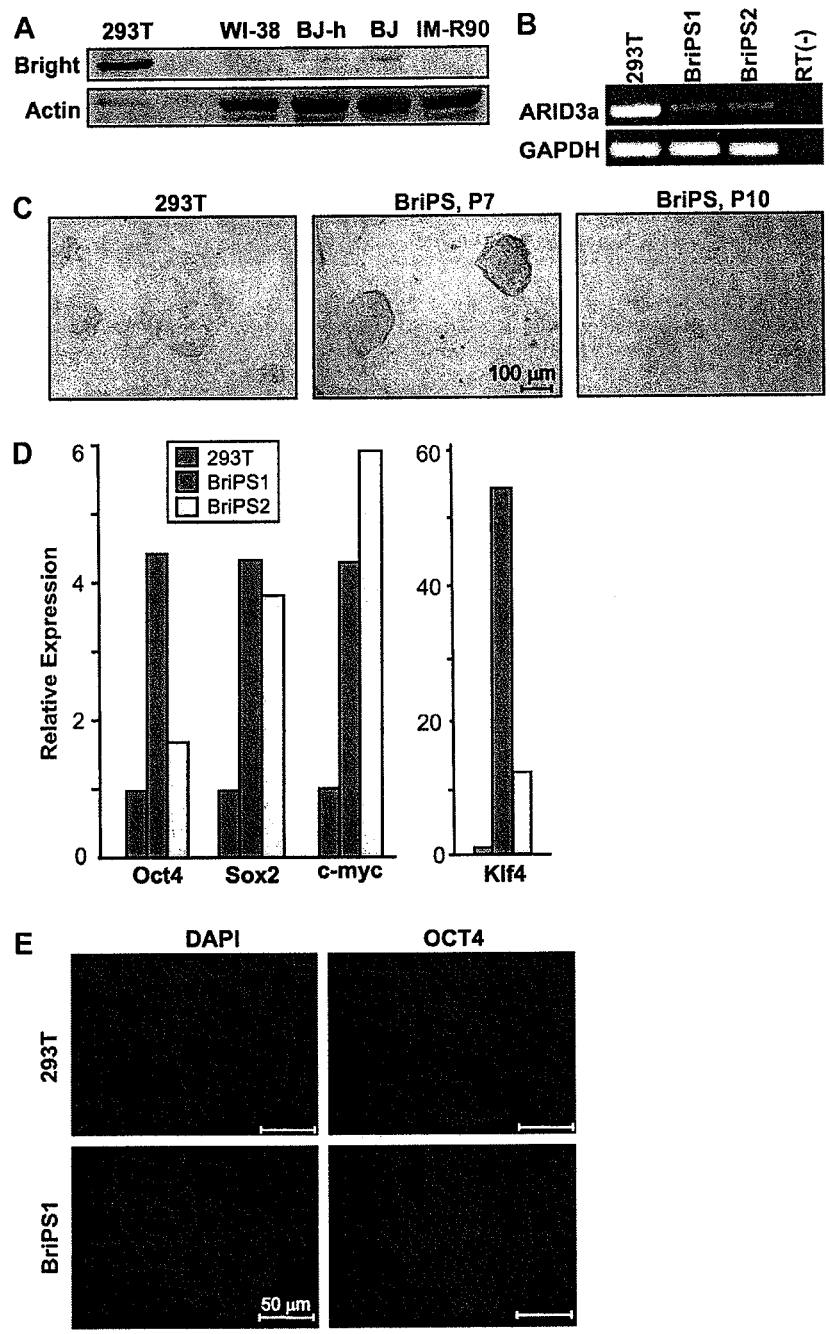
FIGS. 9A-E—ARID3a knockdown results in iPS-like cell generation in a human endothelial cell line.
Figure 12:
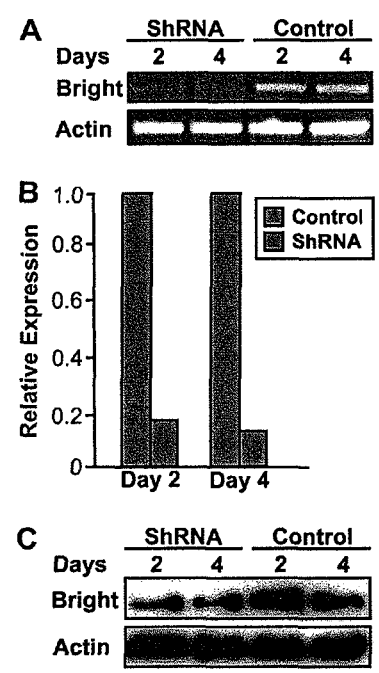
FIGS. 12A-C—Optimization of shRNA knockdown of Bright expression in a highly expressing, mouse B cell line.

The knockout and transgenic results predict that extrinsic reduction of Bright would allow reprogramming of somatic cells into iPS-like states. The inventors generated, expressed and tested a panel of shRNAs (Table 7 and FIG. 12) and were able to effectively inhibit both mouse and human (herafter termed ARID3a) forms of Bright. ARID3a, like its Drosophila and Xenopus orthologues, is expressed broadly in embryonic tissues, but more selectively in adult somatic cells (Webb et al., 1998; Nixon et al., 2004). In addition, reprogramming of human cells was facilitated in some experiments by the presence of SV40 large T antigen (Yu et al., 2009). The human embryonic epithelial cell line, 293T met both of these criteria. 293T epithelia constitutively express high levels of ARID3a relative to the human fibroblast lines more commonly used for iPS production (FIG. 9A), as well as large T antigen. The inventors found that shRNA knockdown efficiently silenced ARID3a expression in these cells (FIG. 9B). After only six days of infection, cells underwent morphological changes and resembled tight iPS-like colonies after multiple passages rather than the typical 293T adherent monolayer (FIG. 9C). Yet the ARID3a-inhibited clones maintained the original 293T transformed karyotype (data not shown). Scrambled control shRNA infected cells exhibited no morphological or other iPS-like features. QRT-PCR experiments confirmed that the ARID3a inhibited colonies expressed significantly higher levels of Oct4, Sox2, c-myc and Klf4 than the parental cell line (FIG. 9D). Immunofluorescence staining also indicated that Oct4 protein was expressed in the shRNA-inhibited cells, but was not detected at levels above background staining in the parent cell line (FIG. 9E). These results indicate that ectopic knockdown of ARID3a in human cells induces the key transcription factors necessary for reprogramming to iPS-like cells.

Figure 10:
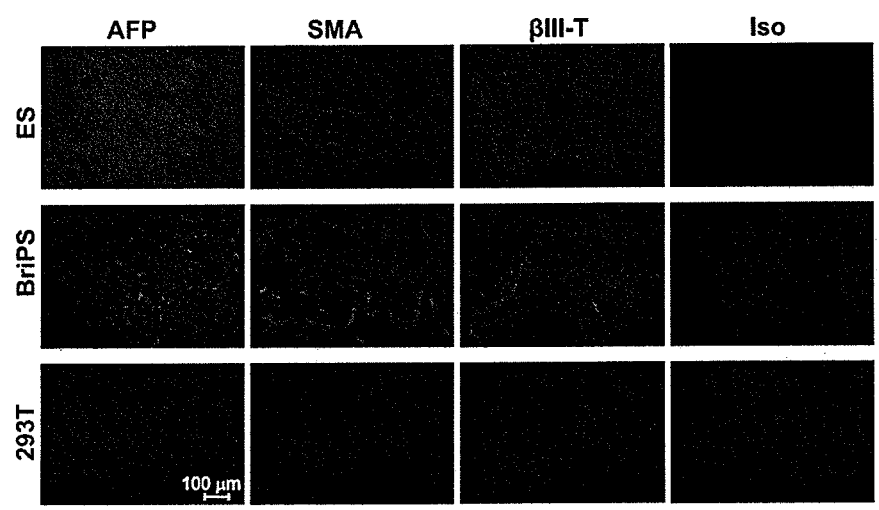
FIG. 10—ARID3a knockdown iPS-like clones differentiate into cells expressing markers for all three germ line lineages. Conventional mouse ES cells (top panels), BriPS (clone A2-P4, middle panels) and parental 293T cells (bottom panels) were stained for α-fetoprotein (AFP), smooth muscle actin (SMA), β-3-tubulin (BIIIT) or an isotype control (ISO). Magnification is 20×.
Figure 13:
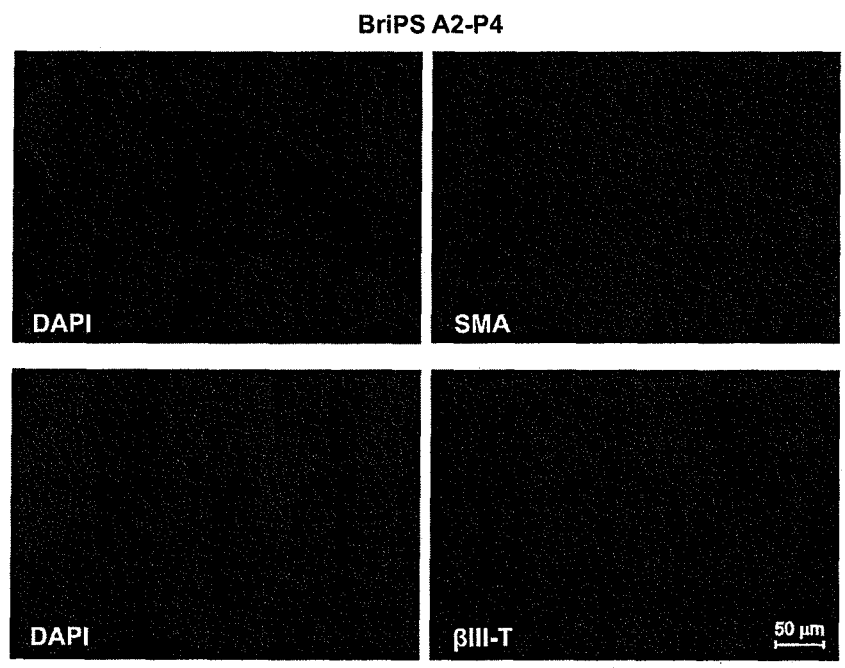
FIG. 13—ARID3a-deficient human iPS cells fail to express differentiation markers prior to embryoid body formation. The clone (BriPS A2-P4) used in FIG. 10 was subjected to nuclear (DAPI, left panels) smooth muscle actin (SMA) and β-III-tubulin (βIII-T) staining. Scale bar shows 50 μm.

To determine if the ARID3a-deficient, iPS-like cells were pluripotent, cells from passage eight were cultured in hanging drops to induce embryoid bodies. After 5 days without LIF, the inventors observed spontaneous expression of markers indicative of mesoderm (smooth muscle actin), endoderm (α-fetoprotein) and ectoderm (β-III tubulin) comparable to that observed in standard murine ES cultures (FIG. 10). Neither the parent 293T cell line (FIG. 10) or the undifferentiated BriPS clones (FIG. 13) expressed these differentiation markers. These data suggest that inhibition of ARID3a is sufficient to reprogram human cells such that they have the ability to express early markers of multiple lineages.

Figure 14:
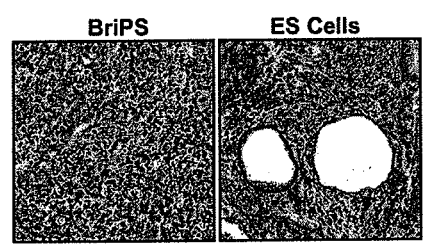
FIG. 14—ARID3a-deficient cells fail to form teratomas in Nod/Scid mice. Shown are representative panels of early neoplastic cells formed from BriPS cells (left) and teratoma formation from conventional ES cells (right). Magnification is 40×.

Further tests for pluripotency were performed by injection of the human ARID3a-deficient iPS-like cells intramuscularly into Nod/Scid mice. Tumor formation was apparent after only 17-21 days, as compared to the parental 293T cells which required 4-6 weeks. However, while pathology reports indicated that mice injected with control mouse ES cells generated teratomas, the ARID3a-deficient human cell tumors remained undifferentiated and did not appear to be metastatic (FIG. 14). Failure to form teratomas in this case could indicate that ARID3a-deficient iPS-like human cells are not truly pluripotent, although certainly multipotent. Still another possibility is that ARID3a inhibition may lead to reprogramming of cells without teratoma production in vivo as has been observed for other human iPS-like cell lines (Shih et al., 2007). These data suggest that ARID3a-deficient cells resemble iPS cells in their ability to express early markers of mesoderm, endoderm, and ectoderm, but that they differ from true iPS cells in that they do not generate teratomas derived from terminally-differentiated tissues of multiple types.

TABLE 6

Self-Renewing Bright Deficient Cell Lines

| Cell Line | Tissue Source | Mouse Phenotype | Time in Culture (months) |
|---|---|---|---|
| DNBr90 | Spleen | DNB | >8 |
| DNBr89 | Spleen | DNB | 6 |
| SKPS1 | Spleen | Bright$^{-/-}$ | >12 |
| SKPS2 | Spleen | Bright$^{-/-}$ | 2 |
| SKPS3 | Spleen | Bright$^{-/-}$ | 2 |
| SKPS7 | Spleen | Bright$^{-/-}$ | >6 |
| SCDNB36* | Spleen | cDNB$^{+/+}$ | >14 |
| SCDNB50* | Spleen | cDND$^{+/+}$ | >6 |
| BKPS4 | Bone Marrow | Bright$^{-/-}$ | >5 |
| BKPS5 | Bone Marrow | Bright$^{-/-}$ | >5 |
| BKPS6 | Bone Marrow | Bright$^{-/-}$ | >8 |
| BKPS7 | Bone Marrow | Bright$^{-/-}$ | >5 |
| cBDND | Bone Marrow | cDND | >10 |
| KKPS5 | Kidney | Bright$^{-/-}$ | >12 |
| LNKPS5 | Lymph Node | Bright$^{-/-}$ | >4 |
| DNpre-BI | Sorted pre-B cells | cDNB | 3 |
| DNpre-BII* | Sorted pre-B cells | DND$^{+/+}$ | 4 |
| DNpre-BIII* | Sorted pre-B cells | cDNB$^{+/+}$ | 5 |
| DNpre-BIV* | Sorted pre-B Cells | cDND$^{+/+}$ | >4 |

Cell lines generated from Bright deficient tissues were named according to their origin from DN or knockout (K) mice with unique numbers.
Asterisks (*) indicate the mice were homozygous for the transgene.
Two DN transgenic lines were generated (B and D).
Transgenic mice on a c57Bl/6 background are preceded by a lower case c.

TABLE 7 shRNA Primers

| ShRNA | Location | Start Amino Acid | Sequence |
|---|---|---|---|
| 1 | Exon 1 | 54 | GGATGCATAGGACTCAGAT (SEQ ID NO: 53) |

TABLE 7-continued shRNA Primers

| ShRNA | Location | Start Amino Acid | Sequence |
|---|---|---|---|
| 2 | Exon 2 | 232 | GCAGTTCAAACAGCTCTAT (SEQ ID NO: 54) |
| 3 | Exon 4 | 274 | CCTCGACCTGTTCATGTTGT (SEQ ID NO: 55) |
| 4 | Exon 7 | 523 | GTATTAGCATGTCCGTGGA (SEQ ID NO: 56) |

ShRNA primer sequences for Bright are listed and their point of origin within the coding sequence is indicated. The DNA binding domains of mouse Bright and human ARID3a are sufficiently homologous that these shRNAs effectively inhibited ARID3a.

Example 4

Discussion

The inventors have provided three independent lines of evidence indicating that inhibition of a single transcription factor, Bright/ARID3a, promotes reprogramming of somatic cells into an iPS-like state. First, Bright$^{-/-}$ cells from multiple tissues exhibit self-renewing growth properties, form embryoid-like bodies, express stem cell markers and exhibit the potential to differentiate into cells of multiple lineages. Second, bone marrow and spleen cells from DN Bright transgenic mice exhibit similar properties. These iPS-like cells retain evidence of Ig recombination, indicating that they originated from B lymphocyte lineage cells in which the DN Bright transgenic protein was specifically expressed. Third, direct knockdown of ARID3a in a human epithelial cell line resulted in upregulation of reprogramming factors, an iPS-like morphology and the ability to express pluripotent markers in vitro. These data suggest that Bright/ARID3a inhibition is important in the production of iPS-like cells in both the mouse and human, and provide strong support for a model in which Bright/ARID3a acts as a suppressor of pluripotency.

The iPS-like cells produced by Bright inhibition differ in some respects from those previously reported. Others have shown that Oct4 regulates Nanog and Sox2, and that Oct4 is critically necessary for production of iPS in the mouse (Takahashi and Yamanaka, 2006; Feng et al., 2009). The inventors have only rarely observed Oct4 induction in either of our Bright-deficient mouse systems. This suggests that these iPS-like cells are slightly more differentiated than conventional LIF-requiring ES cells and may have lost Oct4 expression. In some cases, stem cell formation depends on Oct4, but maintenance does not (Pereira et al., 2008). Oct4 levels are tightly regulated and change quickly with differentiation (Feng et al., 2009). Unlike the situation with murine cells, we observed a marked induction of Oct4 at both the protein and mRNA levels in human ARID3a-deficient clones.

What little is known regarding Bright transcriptional potential derives from studies of IgH gene regulation (reviewed in (Webb et al., 1999)). Binding of Bright to A+T rich sequences within the nuclear matrix associated regions (MARs) in the IgH locus prior to nucleosome assembly allowed enhanced transcription and suggested that Bright contributes to the accessibility of the IgH enhancer (Webb et al., 1991; Lin et al., 2007). A+T rich sequences have been shown to be important sites for recruitment of multiple key pluripotency regulators (Kim et al., 2008). Intriguingly, Sox2, like Bright, is a MAR binding protein (Iarovaia et al., 2005). Previously proposed pluripotency network models linked Bright/ARID3a to Klf4 and to Nanog through expression profiling (Kim et al., 2008) or protein complex analyses (Wang et al., 2006). However, neither study identified or suggested a function for Bright/ARID3a in the pathway. The inventors hypothesize that the lag time required for generating pluripotent cells observed by others in current reprogramming systems is necessary to allow extinction of ARID3a/Bright function. These data indicate that inhibition of ARID3a is sufficient to upregulate, either directly or indirectly, Klf4 and other key regulators. Therefore, current models must be amended to consider Bright/ARID3a as a central upstream repressor of self-renewal/pluripotency.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

X. REFERENCES

The following references, to the extent that they provide exemplary procedural or other details supplementary to those set forth herein, are specifically incorporated herein by reference.

U.S. Pat. No. 3,826,364
U.S. Pat. No. 4,284,412
U.S. Pat. No. 4,989,977
U.S. Pat. No. 4,498,766
U.S. Pat. No. 5,478,722
U.S. Pat. No. 4,857,451
U.S. Pat. No. 4,774,189
U.S. Pat. No. 4,767,206
U.S. Pat. No. 4,714,682
U.S. Pat. No. 5,160,974
U.S. Pat. No. 4,661,913
U.S. Pat. No. 4,415,732
U.S. Pat. No. 4,458,066
U.S. Pat. No. 4,659,774
U.S. Pat. No. 4,816,571
U.S. Pat. No. 5,141,813
U.S. Pat. No. 5,264,566
U.S. Pat. No. 4,959,463
U.S. Pat. No. 5,428,148
U.S. Pat. No. 5,554,744
U.S. Pat. No. 5,574,146
U.S. Pat. No. 5,602,244
U.S. Pat. No. 4,682,195
U.S. Pat. No. 4,683,202
U.S. Pat. No. 4,946,778
U.S. Pat. No. 5,354,855
U.S. Pat. No. 5,440,013
U.S. Pat. No. 5,446,128
U.S. Pat. No. 5,475,085
U.S. Pat. No. 5,618,914

U.S. Pat. No. 5,645,897
U.S. Pat. No. 5,670,155
U.S. Pat. No. 5,672,681
U.S. Pat. No. 5,674,976
U.S. Pat. No. 5,705,629
U.S. Pat. No. 5,710,245
U.S. Pat. No. 5,795,715
U.S. Pat. No. 5,840,833
U.S. Pat. No. 5,859,184
U.S. Pat. No. 5,888,773
U.S. Pat. No. 5,889,136
U.S. Pat. No. 5,889,155
U.S. Pat. No. 5,929,237
U.S. Pat. No. 5,994,136
U.S. Pat. No. 6,013,516
U.S. Pat. No. 6,261,569
Angel et al., *Mol. Cell. Biol.*, 7:2256, 1987a.
Angel et al., *Cell*, 49:729, 1987b.
Arend and Dayer, *Arthritis Rheum.*, 38:151-160, 1995.
Arend et al., *Annu. Rev. Immunol.*, 16:27-55, 1998.
Atchison and Perry, *Cell*, 46:253, 1986.
Atchison and Perry, *Cell*, 48:121, 1987.
Baichwal and Sugden, In: *Gene Transfer*, Kucherlapati (Ed.), NY, Plenum Press, 117-148, 1986.
Bakre et al., *J Biol. Chem.*, 282:31703, 2007.
Banerji et al., *Cell*, 27(2 Pt 1):299-308, 1981.
Banerji et al., *Cell*, 33(3):729-740, 1983.
Barany and Merrifield, In: *The Peptides*, Gross and Meienhofer (Eds.), Academic Press, NY, 1-284, 1979.
Barcellof et al., *Development*, 105:223, 1989.
Benvenisty and Neshif, *Proc. Natl. Acad. Sci. USA*, 83(24): 9551-9555, 1986.
Berkhout et al., *Cell*, 59:273-282, 1989.
Biederer and Scheiffele, *Nature Protocols*, 2(3):670, 2007.
Bissel et al., *J. Clinical Invest.*, 79:801, 1987.
Blanar et al., *EMBO J.*, 8:1139, 1989.
Blomer et al., *J. Virol.*, 71(9):6641-6649, 1997.
Bodanszky et al., *J. Antibiot.*, 29(5):549-53, 1976.
Bodine and Ley, *EMBO J.*, 6:2997, 1987.
Boshart et al., *Cell*, 41:521, 1985.
Bosher et al., *Nat. Cell. Biol.*, 2(2):E31-E36, 2000.
Bosze et al., *EMBO J.*, 5(7):1615-1623, 1986.
Braddock et al., *Cell*, 58:269, 1989.
Bulla and Siddiqui, *J. Virol.*, 62:1437, 1986.
Burns and Peterson, *Mol. Cell. Biol.*, 17:4811-4819, 1997.
Callery et al., *Dev. Biol.*, 278:542, 2005.
Campbell and Villarreal, *Mol. Cell. Biol.*, 8:1993, 1988.
Campbell et al., *Am. Rev. Respir. Dis.*, 130(3):417-423, 1984.
Campere and Tilghman, *Genes and Dev.*, 3:537, 1989.
Campo et al., *Nature*, 303:77, 1983.
Caplen et al., Gene, 252(1-2):95-105, 2000.
Celander and Haseltine, *J. Virology*, 61:269, 1987.
Celander et al., *J. Virology*, 62:1314, 1988.
Chandler et al., Cell, 33:489, 1983.
Chang et al., *Hepatology*, 14:134A, 1991.
Chang et al., *Mol. Cell. Biol.*, 9:2153, 1989.
Chatterjee et al., *Proc. Natl. Acad. Sci. USA*, 86:9114, 1989.
Chen and Okayama, *Mol. Cell Biol.*, 7(8):2745-2752, 1987.
Chen et al., *J. Immunol.*, 180(1):138-45, 2008.
Choi et al., *Cell*, 53:519, 1988.
Coffin, In: *Virology*, Fields et al. (Eds.), Raven Press, NY, 1437-1500, 1990.
Cohen et al., *J. Cell. Physiol.*, 5:75, 1987.
Cohen et al., *J. Med. Chem.*, 33:883-894, 1990.
Conley et al., *Immunol. Rev.*, 138:5-21, 1994.
Cook et al., *Cell*, 27:487-496, 1981.
Costa et al., *Mol. Cell. Biol.*, 8:81, 1988.
Couch et al., *Am. Rev. Resp. Dis.*, 88:394-403, 1963.
Coupar et al., *Gene*, 68:1-10, 1988.
Cripe et al., *EMBO J.*, 6:3745, 1987.
Culotta and Hamer, *Mol. Cell. Biol.*, 9:1376, 1989.
Dallas et al., *Mol. Cell. Biol.*, 20:3137-3146, 2000.
Dandolo et al., *J. Virology*, 47:55-64, 1983.
De Villiers et al., *Nature*, 312(5991):242-246, 1984.
Debnath et al., *Methods*, 30(3):256, 2003.
Deschamps et al., *Science*, 230:1174-1177, 1985.
Dubensky et al., *Proc. Natl. Acad. Sci. USA*, 81:7529-7533, 1984.
Edbrooke et al., *Mol. Cell. Biol.*, 9:1908, 1989.
Edlund et al., *Science*, 230:912-916, 1985.
Elbashir et al., *Nature*, 411(6836):494-498, 2001.
European App. EP 266 032
European Appln. EPO 0273085
Fattaey et al., *Oncogene*, 8:3149-3156, 1993.
Fechheimer, et al., *Proc Natl. Acad. Sci. USA*, 84:8463-8467, 1987.
Feng and Holland, *Nature*, 334:6178, 1988.
Feng et al., *Cell Stem Cell*, 4:301, 2009.
Ferkol et al., *FASEB J.*, 7:1081-1091, 1993.
Fernandez et al., *Mol. Cell Biol.*, 21:196-208, 2001.
Fico et al., *Stem Cells and Development* 17:573-584, 2008.
Firak and Subramanian, *Mol. Cell. Biol.*, 6:3667, 1986.
Fire et al., *Nature*, 391(6669):806-811, 1998.
Firestein et al., *Arthritis Rheum.*, 37:644-652, 1994.
Flowers et al., *J. Biol. Chem.*, 284(15):10067-75, 2009.
Foecking and Hofstetter, *Gene*, 45(1):101-105, 1986.
Forster and Symons, *Cell*, 49(2):211-220, 1987.
Fouad et al., *J. of Neurosci.*, 25(5):1169, 2005.
Fraley et al., *Proc. Natl. Acad. Sci. USA*, 76:3348-3352, 1979.
Friedmann, *Science*, 244:1275-1281, 1989.
Froehler et al., *Nucleic Acids Res.*, 14(13):5399-5407, 1986.
Fujita et al., Cell, 49:357, 1987.
Fukuyo et al., *Cell Death. Differ.*, 11:747-759, 2004.
Gefter et al., *Somatic Cell Genet.*, 3:231-236, 1977.
Gerlach et al., *Nature (London)*, 328:802-805, 1987.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Ghosh-Choudhury et al., *EMBO J.*, 6:1733-1739, 1987.
Gilles et al., *Cell*, 33:717, 1983.
Gloss et al., *EMBO J.*, 6:3735, 1987.
Godbout et al., *Mol. Cell. Biol.*, 8:1169, 1988.
Goding, In: *Monoclonal Antibodies: Principles and Practice*, 2d ed., Academic Press, FL., 60-66, and 71-74, 1986.
Gomez-Foix et al., *J. Biol. Chem.*, 267:25129-25134, 1992.
Goodbourn and Maniatis, *Proc. Natl. Acad. Sci. USA*, 85:1447, 1988.
Goodbourn et al., *Cell*, 45:601, 1986.
Goodman and Gilman's *The Pharmacological Basis Of Therapeutics*, Hardman et al. (Eds.), 10$^{th}$ Ed., 32:853-860; 35:891-893, 2001.
Gopal, *Mol. Cell Biol.*, 5:1188-1190, 1985.
Graham and Prevec, In: *Methods in Molecular Biology. Gene Transfer and Expression Protocol*, Murray (Ed.), Humana Press, Clifton, N.J., 7:109-128, 1991.
Graham and Van Der Eb, *Virology*, 52:456-467, 1973.
Graham et al, *J. General Virology*, 36:59-74, 1977.
Gray et al., *J. Biol. Chem.*, 280:28507, 2005.
Greene et al., *Immunology Today*, 10:272, 1989
Gregory et al., *Mol. Cell. Biol.* 16:792-799, 1996.
Grishok et al., *Science*, 287:2494-2497, 2000.
Grosschedl and Baltimore, *Cell*, 41:885, 1985.

Grunhaus and Horwitz, *Seminar in Virology,* 3:237-252, 1992.
Guan et al., *Cell Tissue Res* 305:171-176, 2001.
Gurdon and Melton, *Science,* 322:1811, 2008.
Hadley et al., *J. Cell Biol.,* 101:1511, 1985.
Hanna et al., *Cell Stem Cell,* 4:1, 2009.
Hanna et al., *Cell,* 133(2):250-264, 2008.
Harland and Weintraub, *J. Cell Biol.,* 101(3):1094-1099, 1985.
Harlow and Lane, In: *Antibodies: A Laboratory Manual,* Cold Spring Harbor Laboratory, Cold Spring Harbor, N.Y., 346-348, 1988.
Haslinger and Karin, *Proc. Natl. Acad. Sci. USA,* 82:8572, 1985.
Hauber and Cullen, *J. Virology,* 62:673, 1988.
Hen et al., *Nature,* 321:249, 1986.
Hensel et al., *Lymphokine Res.,* 8:347, 1989.
Hermonat and Muzycska, *Proc. Natl. Acad. Sci. USA,* 81:6466-6470, 1984.
Herr and Clarke, *Cell,* 45:461, 1986.
Herrscher et al., *Genes Dev.* 9:3067-3082, 1995.
Hersdorffer et al., *DNA Cell Biol.,* 9:713-723, 1990.
Herz and Gerard, *Proc. Natl. Acad. Sci. USA,* 90:2812-2816, 1993.
Hirochika et al., *J. Virol.,* 61:2599, 1987.
Hirsch et al., *Mol. Cell. Biol.,* 10:1959, 1990.
Ho et al., *Proc. Natl. Acad. Sci. USA,* 106:5181, 2009.
Holbrook et al., *Virology,* 157:211, 1987.
Horlick and Benfield, *Mol. Cell. Biol.,* 9:2396, 1989.
Horwich et al. *J. Virol.,* 64:642-650, 1990.
Huang et al., *Cell,* 27:245, 1981.
Hug et al., *Mol. Cell. Biol.,* 8:3065, 1988.
Hwang et al., *Mol. Cell. Biol.,* 10:585, 1990.
Iarovaia et al., *Nucleic Acids Res.,* 33:4157, 2005.
Imagawa et al., *Cell,* 51:251, 1987.
Imbra and Karin, *Nature,* 323:555, 1986.
Imler et al., *Mol. Cell. Biol.,* 7:2558, 1987.
Imperiale and Nevins, *Mol. Cell. Biol.,* 4:875, 1984.
Ireland, *Curr Eye Res.,* 16(8):838, 1997.
Iwahara and Clubb, *EMBO J.,* 18:6084-6094, 1999.
Iwahara et al., *EMBO J.,* 21:1197-1209, 2002.
Jackson et al., *J. Med. Virol.,* 51:67-79, 1997.
Jakobovits et al, *Mol. Cell. Biol.,* 8:2555, 1988.
Jameel and Siddiqui, *Mol. Cell. Biol.,* 6:710, 1986.
Jaynes et al., *Mol. Cell. Biol.,* 8:62, 1988.
Johnson et al., In: *Biotechnology And Pharmacy,* Pezzuto et al. (Eds.), Chapman and Hall, NY, 1993.
Johnson et al., *Mol. Cell. Biol.,* 9:3393, 1989.
Jones and Shenk, *Cell,* 13:181-188, 1978.
Jones et al., *J. Med. Chem.,* 39:904-917, 1996.
Joyce, *Nature,* 338:217-244, 1989.
Kadesch and Berg, *Mol. Cell. Biol.,* 6:2593, 1986.
Kaneda et al., *Science,* 243:375-378, 1989.
Kaplan et al., *J. Biol Chem.,* 276:21325-21330, 2001.
Karin et al., *Mol. Cell. Biol.,* 7:606, 1987.
Karlsson et al., *EMBO J.,* 5:2377-2385, 1986.
Katinka et al., *Cell,* 20:393, 1980.
Kato et al, *J. Biol. Chem.,* 266:3361-3364, 1991.
Kawamoto et al, *Mol. Cell. Biol.,* 8:267, 1988.
Ketting et al., *Cell,* 99(2):133-141, 1999.
Kiledjian et al., *Mol. Cell. Biol.,* 8:145, 1988.
Kim and Cook, *Proc. Natl. Acad. Sci. USA,* 84(24):8788-8792, 1987.
Kim and Tucker, *Mol. Cell Biol.,* 26:2187-2201, 2006.
Kim et al., *Cell,* 132:1049. 2008.
Kinoshita et al., *Biochem. Biophys. Res. Commun.,* 353:686, 2007.
Klamut et al., *Mol. Cell. Biol.,* 10:193, 1990.
Klein et al., *Nature,* 327:70-73, 1987.
Klein et al., *Proc. Natl. Acad. Sci. USA,* 100:2639-2644, 2003.
Koch et al., *Mol. Cell. Biol.,* 9:303, 1989.
Kohler and Milstein, *Eur. J. Immunol.,* 6:511-519, 1976.
Kohler and Milstein, *Nature,* 256:495-497, 1975.
Kortschak et al., *Genomics,* 51:288-292, 1998.
Kriegler and Botchan, In: *Eukaryotic Viral Vectors,* Gluzman (Ed.), Cold Spring Harbor: Cold Spring Harbor Laboratory, NY, 1982.
Kriegler and Botchan, *Mol. Cell. Biol.,* 3:325, 1983.
Kriegler et al., *Cell,* 38:483, 1984.
Kriegler et al., *Cell,* 53:45, 1988.
Kuhl et al., *Cell,* 50:1057, 1987.
Kunz et al., *Nucl. Acids Res.,* 17:1121, 1989.
Larsen et al., *Proc Natl. Acad. Sci. USA.,* 83:8283, 1986.
Laspia et al., *Cell,* 59:283, 1989.
Latimer et al., *Mol. Cell. Biol.,* 10:760, 1990.
Le Gal La Salle et al., *Science,* 259:988-990, 1993.
Lee et al., *Mol. Immunol.,* 39:923-932, 2003.
Lee et al., *Nature,* 294:228, 1981.
Lee et al., *Nucleic Acids Res.,* 12:4191-206, 1984.
Levinson et al., *Nature,* 295:79, 1982.
Levrero et al., *Gene,* 101:195-202, 1991.
Li et al., *Nature,* 434:894, 2005.
Li et al., *Oncogene,* 15:1375-1383, 1997.
Li et al., *Proc. Nat. Acad. Sci. USA,* 84:136, 1987.
Lin and Grosschedl, *Nature,* 376:263-267, 1995.
Lin et al., *Genetics,* 153:1245-1256, 1999.
Lin et al., *Methods Enzymol.,* 241:195-224, 1994.
Lin et al., *Mol Cancer,* 6:23, 2007.
Lin et al., *Mol. Cell. Biol.,* 10:850, 1990.
Lin et al., *Mol. Cell. Biol.,* 22:4771-4780, 2002.
Lipsky, In: *Harrison's principles of internal medicine,* Fauci et al. (Eds.), 14$^{th}$ Ed., NY, McGraw-Hill, 1880-1888, 1998.
Liu et al., *Biochem. Biophys. Res. Commun.,* 362:575, 2007.
Lowry et al., *J. Biol. Chem.,* 276:45276-45281, 2001.
Luria et al., *EMBO J.,* 6:3307, 1987.
Lusky and Botchan, *Proc. Natl. Acad. Sci. USA,* 83:3609, 1986.
Lusky et al. *Mol. Cell. Biol.,* 3:1108, 1983.
Ma et al., *Cell Growth Differ.,* 1:438-444, 2003.
Macejak and Sarnow, *Nature,* 353:90-94, 1991.
Madison et al., *Exp. Neurology,* 88:767, 1985.
Maherali and Hochedlinger, *Cell Stem Cell,* 3:595, 2008.
Majors and Varmus, *Proc. Natl. Acad. Sci. USA,* 80:5866, 1983.
Mann et al., *Cell,* 33:153-159, 1983.
Markowitz et al., *J. Virol.,* 62:1120-1124, 1988.
Marson et al., *Cell Stem Cell,* 3:132, 2008.
McGuire and Orkin, *Biotechniques,* 5(6):456, 1987.
McNeall et al., *Gene,* 76:81, 1989.
Medina et al., *Nat. Immunol.,* 2:718-724, 2001.
Meissner et al., *Methods Mol. Biol.,* 482:3, 2009.
Meissner et al., *Nat. Biotechnol.* 25, 1177, 2007.
Merrifield, *J. Am. Chem. Soc.,* 85:2149-2154, 1963.
Merrifield, *Science,* 232(4748):341-347, 1986.
Michel and Westhof, *J. Mol. Biol.,* 216:585-610, 1990.
Miksicek et al., *Cell,* 46:203, 1986.
Montgomery et al., *Proc. Natl. Acad. Sci. USA,* 95:15502-15507, 1998.
Mordacq and Linzer, *Genes and Dev.,* 3:760, 1989.
Moreau et al., *Nucl. Acids Res.,* 9:6047, 1981.
Muesing et al., *Cell,* 48:691, 1987.
Muthuswamy et al., *Nat. Cell Biol.,* 3(9):785, 2001.

Naldini et al., *Science*, 272(5259):263-267, 1996.
Navia et al., *Curr. Opin. Struct. Biol.*, 2:202-210, 1992.
Ng et al., *Nuc. Acids Res.*, 17:601, 1989.
Nicolas and Rubenstein, In: *Vectors: A survey of molecular cloning vectors and their uses*, Rodriguez and Denhardt (Eds.), Stoneham: Butterworth, 494-513, 1988.
Nicolau and Sene, *Biochim. Biophys. Acta*, 721:185-190, 1982.
Nicolau et al., *Methods Enzymol.*, 149:157-176, 1987.
Nixon et al., *Cellular Immunol.*, 228:42-53, 2004.
Nixon et al., *J. Biol. Chem.*, 279(50):52465-52472, 2004.
Nixon et al., *J. Immunol.*, 181:6913, 2008.
Numata et al., *Cancer Res.*, 59:3741-3747, 1999.
Ondek et al., *EMBO J.*, 6:1017, 1987.
Ornitz et al., *Mol. Cell. Biol.*, 7:3466, 1987.
Page et al., *Toxilogical Sciences*, 97(2):384, 2007.
Palmiter et al., *Nature*, 300:611, 1982.
Park et al., *Nature*, 451:141, 2008.
Paskind et al., *Virology*, 67:242-248, 1975.
PCT Appln. PCT/US00/14667
PCT Appln. WO 00/44914
PCT Appln. WO 01/68836
PCT Appln. WO 84/03564
PCT Appln. WO 99/32619
PCT Appln. WO 01/36646
Pech et al., *Mol. Cell. Biol.*, 9:396, 1989.
Peeper et al., *Nat. Cell Biol.*, 4:148-153, 2002.
Pei, *J. Biol. Chem.*, 284:3365, 2009.
Pelletier and Sonenberg, *Nature*, 334(6180):320-325, 1988.
Peptide Synthesis, 1985
Perales et al., *Proc. Natl. Acad. Sci. USA*, 91:4086-4090, 1994.
Pereira et al., *PLoS. Genet.*, 4e:1000170, 2008.
Perez-Stable and Constantini, *Mol. Cell. Biol.*, 10: 1116, 1990.
Peterson and Herskowitz, *Cell*, 68:573-583, 1992.
Picard and Schaffner, *Nature*, 307:83, 1984.
Pinkert et al., *Genes and Dev.*, 1:268, 1987.
Ponta et al., *Proc. Natl. Acad. Sci. USA*, 82:1020, 1985.
Porton et al., *Mol. Cell. Biol.*, 10:1076, 1990.
Potter et al., *Proc. Natl. Acad. Sci. USA*, 81:7161-7165, 1984.
Protective Groups in Organic Chemistry, 1973
Queen and Baltimore, *Cell*, 35:741, 1983.
Quinn et al., *Mol Cell. Biol.*, 9:4713, 1989.
Racher et al., *Biotechnology Techniques*, 9:169-174, 1995.
Ragot et al., *Nature*, 361:647-650, 1993.
Rajaiya et al., *Mol. Cell. Biol.*, 26:4758-4768, 2006.
Ramsden et al., *J. Immunol.*, 153:1150, 1994.
Redondo et al., *Science*, 247:1225, 1990.
Reinhold-Hurek and Shub, *Nature*, 357:173-176, 1992.
Reisman and Rotter, *Mol. Cell. Biol.*, 9:3571, 1989.
Renan, *Radiother. Oncol.*, 19:197-218, 1990.
Resendez Jr. et al., *Mol. Cell. Biol.*, 8:4579, 1988.
Rich et al., *Hum. Gene Ther.*, 4:461-476, 1993.
Ridgeway, In. *Vectors. A survey of molecular cloning vectors and their uses*, Rodriguez and Denhardt (Eds.), Stoneham:Butterworth, 467-492, 1988.
Ripe et al., *Mol. Cell. Biol.*, 9:2224, 1989.
Rippe et al., *Mol. Cell Biol.*, 10:689-695, 1990.
Rittling et al., *Nuc. Acids Res.*, 17:1619, 1989.
Robertson et al., *Nature* 322:445-448, 1986.
Rooney et al., *Rheumatol. Int.*, 10:217-219, 1990.
Rosen et al., *Cell*, 41:813, 1988.
Rosenfeld et al., *Science*, 252:431-434, 1991.
Rosenfeld, et al., *Cell*, 68:143-155, 1992.
Roskelley et al., *Proc. Nat. Acad. Sci. USA*, 91(26):12378, 1994.
Roux et al., *Proc. Natl. Acad. Sci. USA*, 86:9079-9083, 1989.
Saito et al., *Immunity*, 19:669-678, 2003.
Sakai et al., *Genes and Dev.*, 2:1144, 1988.
Sambrook et al, *In: Molecular cloning*, Cold Spring Harbor Laboratory Press, Cold Spring Harbor, N.Y., 2001.
Sarver et al., *Science*, 247:1222-1225, 1990.
Satake et al., *J. Virology*, 62:970, 1988.
Satterthwaite and Witte, *Ann. Rev. Immunol.*, 14:131-154, 1996.
Scanlon et al., *Proc. Natl. Acad. Sci. USA*, 88:10591-10595, 1991.
Schaffner et al., *J. Mol. Biol.*, 201:81, 1988.
Searle et al., *Mol. Cell. Biol.*, 5:1480, 1985.
Shaffer et al., *Immunity*, 17:51, 2002.
Shandala et al., *Development*, 126:4341, 1999.
Sharp and Marciniak, *Cell*, 59:229, 1989.
Sharp et al., *Science*, 287:2431-2433, 2000.
Sharp, *Genes Dev.*, 13:139-141, 1999.
Shaul and Ben-Levy, *EMBO J.*, 6:1913, 1987.
Sherman et al., *Mol. Cell. Biol.*, 9:50, 1989.
Shih et al., *Stem Cells Dev.*, 16:893, 2007.
Sleigh and Lockett, *J. EMBO*, 4:3831, 1985.
Solid Phase Peptide Synthelia, 1984.
Spalholz et al., *Cell*, 42:183, 1985.
Spandau and Lee, *J. Virology*, 62:427, 1988.
Spandidos and Wilkie, *EMBO J.*, 2:1193, 1983.
Stephens and Hentschel, *Biochem. J.*, 248:1, 1987.
Stewart and Young, In: *Solid Phase Peptide Synthesis*, 2d. ed., Pierce Chemical Co., 1984.
Stratford-Perricaudet and Perricaudet, In: *Human Gene Transfer*, Eds, Cohen-Haguenauer and Boiron, John Libbey Eurotext, France, 51-61, 1991.
Stratford-Perricaudet et al., *Hum. Gene. Ther.*, 1:241-256, 1990.
Stuart et al., *Nature*, 317:828, 1985.
Sullivan and Peterlin, *Mol. Cell. Biol.*, 7:3315, 1987.
Suzuki et al., *Oncogene*, 17:853-865, 1998.
Swartzendruber and Lehman, *J. Cell. Physiology*, 85:179, 1975.
Tabara et al., *Cell*, 99(2):123-132, 1999.
Takahashi et al., *Cell*, 131:861, 2007.
Takahashi, and Yamanaka, *Cell*, 126:663, 2006.
Takebe et al, *Mol. Cell. Biol.*, 8:466, 1988.
Tam et al., *J. Am. Chem. Soc.*, 105:6442, 1983.
Tanaka et al., *Blood*, 110:107, 2007.
Tavernier et al., *Nature*, 301:634, 1983.
Taylor and Kingston, *Mol. Cell. Biol.*, 10: 165, 1990a.
Taylor and Kingston, *Mol. Cell. Biol.*, 10:176, 1990b.
Taylor et al., *J. Biol. Chem.*, 264:15160, 1989.
Temin, In: *Gene Transfer*, Kucherlapati (Ed.), NY, Plenum Press, 149-188, 1986.
Thiesen et al., *J. Virology*, 62:614, 1988.
Top et al., *J. Infect. Dis.*, 124:155-160, 1971.
Treisman et al., *Genes Dev.* 11:1949-1962, 1997.
Treisman, *Cell*, 42:889, 1985.
Tronche et al., *Mol. Biol. Med.*, 7:173, 1990.
Trudel and Constantini, *Genes and Dev.* 6:954, 1987.
Tu et al., *Nature Structural Molec. Biol.*, 15, 419, 2008.
Tur-Kaspa et al., *Mol. Cell Biol.*, 6:716-718, 1986.
Tyndell et al., *Nuc. Acids. Res.*, 9:6231, 1981.
Vannice and Levinson, *J. Virology*, 62:1305, 1988.
Varmus et al, *Cell*, 25:23-36, 1981.
Vasseur et al, *Proc Natl. Acad. Sci. U.S.A.*, 77:1068, 1980.
Wagner et al., *Proc. Natl. Acad. Sci. USA* 87(9):3410-3414, 1990.

Wang and Calame, *Cell*, 47:241, 1986.
Wang et al., *Mol. Cell. Biol.*, 19:284-295, 1999.
Wang et al., *Nature*, 444:364, 2006.
Webb et al., *Biochemistry*, 28:4785-4790, 1989.
Webb et al., *Cold Spring Harbor Symp. Quant. Biol.* LXIV, 109, 1999.
Webb et al., In: *Differential regulation of immunoglobulin gene transcription via nuclear matrix-associated regions*, Cold Spring Harbor Symp. Quant. Biol. LXIV, 109, 1999.
Webb et al., *J. Immunol.*, 143:3934-3939, 1989.
Webb et al., *J. Immunol.*, 160:4747-4754, 1998.
Webb et al., *J. Immunol.*, 165:6956-6965, 2000.
Webb et al., *Mol. Cell. Biol.*, 11:5206-5211, 1991.
Webb et al., *Nuc. Acids Res.*, 21:4363-4368, 1993.
Webb, et al., *Mol. Cell. Biol.*, 11:5197-5205, 1991.
Weber et al., *Cell*, 36:983, 1984.
Weinberger et al. *Mol. Cell. Biol.*, 8:988, 1984.
Wilsker et al., *Cell Growth Differ.*, 13:95, 2002.
Wilsker et al., *Genomics*, 86:242-251, 2005.
Wincott et al., *Nucleic Acids Res.*, 23(14):2677-2684, 1995.
Winoto and Baltimore, *Cell* 59:649, 1989.
Wong et al., *Gene*, 10:87-94, 1980.
Wu and Wu, *Adv. Drug Delivery Rev.*, 12:159-167, 1993.
Wu and Wu, *Biochemistry*, 27:887-892, 1988.
Wu and Wu, *J. Biol. Chem.*, 262:4429-4432, 1987.
Xu et al., *J. Biol. Chem.*, 282(20): 14992, 2007.
Xu et al., *J. Comp. Neurol.*, 351(1):145, 1994.
Yang et al., *Proc. Natl. Acad. Sci. USA*, 87:9568-9572, 1990.
Yao et al., *Proc. Natl. Acad. Sci. USA*, 91:9175-9179, 1994.
Yu et al., *Science*, 318:1917-1920, 2007.
Yu et al., *Science*, 324(5928):797-801, 2009.
Yutzey et al. *Mol. Cell. Biol.*, 9:1397, 1989.
Zelenin et al., *FEBS Lett.*, 280:94-96, 1991.
Zufferey et al., *Nat. Biotechnol.*, 15(9):871-875, 1997.

What is claimed is:

1. A method of rendering a differentiated cell multipotent comprising:
   (a) providing a differentiated cell; and
   (b) contacting said cell with an inhibitory nucleic acid that reduces Bright/ARID3a expression to induce de-differentiation in said cell; and
   (c) culturing said cell in medium including leukemia inhibitory factor,
   wherein de-differentiation renders said cell multipotent.

2. The method of claim 1, wherein said cell of step (a) is a bone marrow cell, fibroblast cell or a spleen cell.

3. The method of claim 1, wherein said cell of step (a) is a peripheral blood cell.

4. The method of claim 1, wherein said inhibitory nucleic acid that reduces Bright/ARID3a expression is an interfering RNA.

5. The method of claim 4, wherein interfering RNA is an shRNA.

6. The method of claim 5, wherein said shRNA is expressed from an expression vector.

7. The method of claim 1, wherein inhibition of Bright/ARID3a function is reversible.

8. A method of reprogramming a differentiated cell comprising:
   (a) providing a differentiated cell;
   (b) contacting said cell with a an inhibitory nucleic acid that reduces Bright/ARID3a expression to induce de-differentiation in said cell; and;
   (c) contacting said cell, following de-differentiation, with a signal selected to produce a re-differentiated cell phenotype;
   (d) culturing said cell with said signal for a period of time sufficient to produce said re-differentiated cell phenotype; and
   (e) identifying one or more aspects of said re-differentiated cell phenotype in said cell.

9. The method of claim 8, wherein said cell of step (a) is a bone marrow cell, a spleen cell, or a peripheral blood cell.

10. The method of claim 8, further comprising restoring Bright/ARID3a function following step (d).

11. The method of claim 8, wherein said signal is a chemokine.

12. The method of claim 8, wherein said re-differentiated cell phenotype is a fat cell phenotype, a neuronal cell phenotype, a pancreatic cell phenotype, a hematopoietic cell phenotype, a muscle cell phenotype or an endothelial cell phenotype.

13. The method of claim 8, wherein said inhibitory nucleic acid is an shRNA.

14. The method of claim 13, wherein said shRNA is expressed from an expression vector.

15. The method of claim 14, wherein said expression vector is a viral expression vector.

16. The method of claim 6, wherein said expression vector is a viral expression vector.

\* \* \* \* \*

UNITED STATES PATENT AND TRADEMARK OFFICE
CERTIFICATE OF CORRECTION

Page 1 of 1

PATENT NO. : 9,453,204 B2
APPLICATION NO. : 12/500987
DATED : September 27, 2016
INVENTOR(S) : Carol Webb and Paul Kincade It is certified that error appears in the above-identified patent and that said Letters Patent is hereby corrected as shown below:

In the Specification

Column 1, Lines 14-17, delete the entire contents of Lines 14-17 and insert --This invention was made with government support under grant number AI044215 awarded by National Institutes of Health. The government has certain rights in the invention.-- therefor.

Signed and Sealed this
Tenth Day of December, 2019

Andrei Iancu
*Director of the United States Patent and Trademark Office*

SEQUENCE LISTING

<160> NUMBER OF SEQ ID NOS: 56

<210> SEQ ID NO 1
<211> LENGTH: 1782
<212> TYPE: DNA
<213> ORGANISM: Homo sapiens

<400> SEQUENCE: 1

```
atgaaactac aggccgtgat ggagacgctg ttgcagcggc agcagcgggc gcgccaggag     60
ctggaggccc ggcagcagct gcccccgat cccctgctg caccccccgg ccgggcccgg      120 gctgccccg acgaggacag agagcccgag agtgcccgga tgcagcgggc tcagatggcc     180
gcactggcag ccatgcgggc tgcagctgcg ggcctggac acccagccag ccccggcggc     240
tctgaggatg ggccccagg ctcggaggag gaggacgcgg cccggaggg gacaccgggc      300 tcacccgggc gaggcagaga agggccagga gaggagcact tgaggacat ggcctccgac     360 gaggacatga agcccaaatg ggaggaggag gagatggagg aagacctcgg ggaggatgag    420
gaggaggagg aggaggatta cgaggatgag gaggaggagg aggacgagga ggggctgggc    480
cccccaggcc ctgccagctt gggcaccacg gcactgttcc cccgaaaggc ccagccaccc    540
caggccttcc gcggcgatgg cgttcccagg gtgctggggg gccaggagcg gccggggcct    600
ggccctgccc accccggagg ggccgcccac gtagcccgc agctgcagcc gcctgaccac     660
ggcgactgga cttacgagga gcagtttaag cagctctacg aactcgacgg ggaccccaag    720
aggaaggaat tcctggatga cttgttcagc ttcatgcaga agcgagggac acctgtgaac    780
cgcatcccca tcatggccaa acaggtcctt gacctgttca tgctgtacgt gctggtgacg    840
gagaagggcg gcctcgtgga ggtcatcaac aagaagctgt ggcgtgagat caccaagggc    900
ctcaacctgc ccacgtccat caccagtgca gccttcaccc tgcggaccca atacatgaag    960
tacctgtacc cctacgagtg tgagaagcgg ggcctcagta accccaatga gctccaggca   1020
gccatagaca gcaaccgacg ggagggccgg cgccagagct ttggtggctc cctctttgcc   1080
tactcgccag gcggggcaca cggcatgctc tcctcaccca agctacccgt gtcctccctg   1140
ggcctggccc aagcaccaa tggcagctcc atcaccccg cccctaagat caagaaagag    1200
gaggactcag ccatccccat cacagtccct ggccgcctgc ctgtgtccct ggcgggccac   1260
cctgtggtgg cagcccaggc agcagctgtg caagcagcag ccgcccaagc agctgtggcc   1320
gcacaggcag ctgcccctgga acagctgcgg gagaagctgg agtctgcaga gcctccggag   1380
aagaagatgg ccctggtggc cgatgagcag caacggctga tgcaacgtgc actccagcag   1440
```

```
aacttcctgg ccatggcggc ccagctgccc atgagcattc ggatcaacag ccaagcctcc   1500
gaaagccgcc aggactctgc tgtgaacctg acgggcacca acggcagcaa cagcatcagc   1560
atgtcggtgg agatcaacgg catcatgtac acaggagttc tgtttgctca gccgccggcc   1620
cccacgccaa cctctgctcc aacaaagga ggcggcggcg gcggcggcag cagcagcaac   1680
gcaggcggcc ggggaggaaa caccggaacc agcggcggcc aggctgggcc agcggggctg   1740
tccacaccct ccacatctac ctcaaataac tcgttgcctt aa                    1782
```

```
<210> SEQ ID NO 2
<211> LENGTH: 593
<212> TYPE: PRT
<213> ORGANISM: Homo sapiens

<400> SEQUENCE: 2
```

```
Met Lys Leu Gln Ala Val Met Glu Thr Leu Leu Gln Arg Gln Gln Arg
1               5                   10                  15

Ala Arg Gln Glu Leu Glu Ala Arg Gln Gln Leu Pro Pro Asp Pro Pro
            20                  25                  30

Ala Ala Pro Pro Gly Arg Ala Arg Ala Ala Pro Asp Glu Asp Arg Glu
        35                  40                  45

Pro Glu Ser Ala Arg Met Gln Arg Ala Gln Met Ala Ala Leu Ala Ala
    50                  55                  60

Met Arg Ala Ala Ala Gly Leu Gly His Pro Ala Ser Pro Gly Gly
65                  70                  75                  80

Ser Glu Asp Gly Pro Pro Gly Ser Glu Glu Asp Ala Ala Arg Glu
                85                  90                  95

Gly Thr Pro Gly Ser Pro Gly Arg Gly Arg Glu Gly Pro Gly Glu Glu
            100                 105                 110

His Phe Glu Asp Met Ala Ser Asp Glu Asp Met Lys Pro Lys Trp Glu
        115                 120                 125

Glu Glu Glu Met Glu Glu Asp Leu Gly Glu Asp Glu Glu Glu Glu Glu
    130                 135                 140

Glu Asp Tyr Glu Asp Glu Glu Glu Glu Asp Glu Glu Gly Leu Gly
145                 150                 155                 160

Pro Pro Gly Pro Ala Ser Leu Gly Thr Thr Ala Leu Phe Pro Arg Lys
                165                 170                 175

Ala Gln Pro Pro Gln Ala Phe Arg Gly Asp Val Pro Arg Val Leu
            180                 185                 190

Gly Gly Gln Glu Arg Pro Gly Pro Gly Pro Ala His Pro Gly Gly Ala
        195                 200                 205

Ala His Val Ala Pro Gln Leu Gln Pro Pro Asp His Gly Asp Trp Thr
    210                 215                 220

Tyr Glu Glu Gln Phe Lys Gln Leu Tyr Glu Leu Asp Gly Asp Pro Lys
225                 230                 235                 240

Arg Lys Glu Phe Leu Asp Asp Leu Phe Ser Phe Met Gln Lys Arg Gly
                245                 250                 255

Thr Pro Val Asn Arg Ile Pro Ile Met Ala Lys Gln Val Leu Asp Leu
            260                 265                 270

Phe Met Leu Tyr Val Leu Val Thr Glu Lys Gly Gly Leu Val Glu Val
        275                 280                 285

Ile Asn Lys Lys Leu Trp Arg Glu Ile Thr Lys Gly Leu Asn Leu Pro
    290                 295                 300

Thr Ser Ile Thr Ser Ala Ala Phe Thr Leu Arg Thr Gln Tyr Met Lys
```

```
            305                 310                 315                 320
        Tyr Leu Tyr Pro Tyr Glu Cys Glu Lys Arg Gly Leu Ser Asn Pro Asn
                        325                 330                 335
        Glu Leu Gln Ala Ala Ile Asp Ser Asn Arg Arg Glu Gly Arg Arg Gln
                        340                 345                 350
        Ser Phe Gly Gly Ser Leu Phe Ala Tyr Ser Pro Gly Gly Ala His Gly
                        355                 360                 365
        Met Leu Ser Ser Pro Lys Leu Pro Val Ser Ser Leu Gly Leu Ala Ala
                370                 375                 380
        Ser Thr Asn Gly Ser Ser Ile Thr Pro Ala Pro Lys Ile Lys Lys Glu
        385                 390                 395                 400
        Glu Asp Ser Ala Ile Pro Ile Thr Val Pro Gly Arg Leu Pro Val Ser
                        405                 410                 415
        Leu Ala Gly His Pro Val Val Ala Ala Gln Ala Ala Val Gln Ala
                        420                 425                 430
        Ala Ala Ala Gln Ala Ala Val Ala Ala Gln Ala Ala Leu Glu Gln
                    435                 440                 445
        Leu Arg Glu Lys Leu Glu Ser Ala Glu Pro Pro Glu Lys Lys Met Ala
                450                 455                 460
        Leu Val Ala Asp Glu Gln Gln Arg Leu Met Gln Arg Ala Leu Gln Gln
        465                 470                 475                 480
        Asn Phe Leu Ala Met Ala Ala Gln Leu Pro Met Ser Ile Arg Ile Asn
                        485                 490                 495
        Ser Gln Ala Ser Glu Ser Arg Gln Asp Ser Ala Val Asn Leu Thr Gly
                        500                 505                 510
        Thr Asn Gly Ser Asn Ser Ile Ser Met Ser Val Glu Ile Asn Gly Ile
                    515                 520                 525
        Met Tyr Thr Gly Val Leu Phe Ala Gln Pro Pro Ala Pro Thr Pro Thr
                530                 535                 540
        Ser Ala Pro Asn Lys Gly Gly Gly Gly Gly Ser Ser Ser Asn
        545                 550                 555                 560
        Ala Gly Gly Arg Gly Gly Asn Thr Gly Thr Ser Gly Gly Gln Ala Gly
                        565                 570                 575
        Pro Ala Gly Leu Ser Thr Pro Ser Thr Ser Thr Ser Asn Asn Ser Leu
                        580                 585                 590
        Pro

<210> SEQ ID NO 3
<211> LENGTH: 23
<212> TYPE: DNA
<213> ORGANISM: Artificial Sequence
<220> FEATURE:
<223> OTHER INFORMATION: Synthetic primer

<400> SEQUENCE: 3
gcggacccca agaggaaaga gtt                                              23

<210> SEQ ID NO 4
<211> LENGTH: 25
<212> TYPE: DNA
<213> ORGANISM: Artificial Sequence
<220> FEATURE:
<223> OTHER INFORMATION: Synthetic primer

<400> SEQUENCE: 4
ctgggtgagt aggcaaagag tgagc                                            25
```

<210> SEQ ID NO 5
<211> LENGTH: 34
<212> TYPE: PRT
<213> ORGANISM: Artificial Sequence
<220> FEATURE:
<223> OTHER INFORMATION: Synthetic peptide

<400> SEQUENCE: 5

Gln Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 6
<211> LENGTH: 16
<212> TYPE: PRT
<213> ORGANISM: Artificial Sequence
<220> FEATURE:
<223> OTHER INFORMATION: Synthetic peptide

<400> SEQUENCE: 6

Arg Gln Ile Lys Ile Trp Phe Gln Asn Arg Arg Met Lys Trp Lys Lys
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Arg Arg Met Lys Trp Lys Lys
1               5

<210> SEQ ID NO 8
<211> LENGTH: 16
<212> TYPE: PRT
<213> ORGANISM: Artificial Sequence
<220> FEATURE:
<223> OTHER INFORMATION: Synthetic peptide

<400> SEQUENCE: 8

Arg Arg Trp Arg Arg Trp Trp Arg Arg Trp Trp Arg Arg Trp Arg Arg
1               5                   10                  15

<210> SEQ ID NO 9
<211> LENGTH: 18
<212> TYPE: PRT
<213> ORGANISM: Artificial Sequence
<220> FEATURE:
<223> OTHER INFORMATION: Synthetic peptide

<400> SEQUENCE: 9

Arg Gly Gly Arg Leu Ser Tyr Ser Arg Arg Arg Phe Ser Thr Ser Thr
1               5                   10                  15

Gly Arg

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide

```
<400> SEQUENCE: 10

Tyr Gly Arg Lys Lys Arg Arg Gln Arg Arg
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Synthetic peptide

<400> SEQUENCE: 11

Arg Lys Lys Arg Arg Gln Arg Arg Arg
1               5

<210> SEQ ID NO 12
<211> LENGTH: 11
<212> TYPE: PRT
<213> ORGANISM: Artificial Sequence
<220> FEATURE:
<223> OTHER INFORMATION: Synthetic peptide

<400> SEQUENCE: 12

Tyr Ala Arg Ala Ala Ala Arg Gln Ala Arg Ala
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Synthetic peptide

<400> SEQUENCE: 13

Arg Arg Arg Arg Arg Arg Arg Arg
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic peptide

<400> SEQUENCE: 14

Lys Lys Lys Lys Lys Lys Lys Lys
1               5

<210> SEQ ID NO 15
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (25)..(25)
<223> OTHER INFORMATION: Xaa can be any naturally occurring amino acid

<400> SEQUENCE: 15

Gly Trp Thr Leu Asn Ser Ala Gly Tyr Leu Leu Gly Lys Ile Asn Leu
1               5                   10                  15

Lys Ala Leu Ala Ala Leu Ala Lys Xaa Ile Leu
            20                  25
```

```
<210> SEQ ID NO 16
<211> LENGTH: 18
<212> TYPE: PRT
<213> ORGANISM: Artificial Sequence
<220> FEATURE:
<223> OTHER INFORMATION: Synthetic peptide

<400> SEQUENCE: 16

Leu Leu Ile Leu Leu Arg Arg Arg Ile Arg Lys Gln Ala Asn Ala His
1               5                   10                  15

Ser Lys

<210> SEQ ID NO 17
<211> LENGTH: 16
<212> TYPE: PRT
<213> ORGANISM: Artificial Sequence
<220> FEATURE:
<223> OTHER INFORMATION: Synthetic peptide

<400> SEQUENCE: 17

Ser Arg Arg His His Cys Arg Ser Lys Ala Lys Arg Ser Arg His His
1               5                   10                  15

<210> SEQ ID NO 18
<211> LENGTH: 11
<212> TYPE: PRT
<213> ORGANISM: Artificial Sequence
<220> FEATURE:
<223> OTHER INFORMATION: Synthetic peptide

<400> SEQUENCE: 18

Asn Arg Ala Arg Arg Asn Arg Arg Arg Val Arg
1               5                   10

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide

<400> SEQUENCE: 19

Arg Gln Leu Arg Ile Ala Gly Arg Arg Leu Arg Gly Arg Ser Arg
1               5                   10                  15

<210> SEQ ID NO 20
<211> LENGTH: 13
<212> TYPE: PRT
<213> ORGANISM: Artificial Sequence
<220> FEATURE:
<223> OTHER INFORMATION: Synthetic peptide

<400> SEQUENCE: 20

Lys Leu Ile Lys Gly Arg Thr Pro Ile Lys Phe Gly Lys
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic peptide

<400> SEQUENCE: 21

Arg Arg Ile Pro Asn Arg Arg Pro Arg Arg
1               5                   10
```

<210> SEQ ID NO 22
<211> LENGTH: 18
<212> TYPE: PRT
<213> ORGANISM: Artificial Sequence
<220> FEATURE:
<223> OTHER INFORMATION: Synthetic peptide

<400> SEQUENCE: 22

Lys Leu Ala Leu Lys Leu Ala Leu Lys Ala Leu Lys Ala Ala Leu Lys
1               5                   10                  15

Leu Ala

<210> SEQ ID NO 23
<211> LENGTH: 14
<212> TYPE: PRT
<213> ORGANISM: Artificial Sequence
<220> FEATURE:
<223> OTHER INFORMATION: Synthetic peptide

<400> SEQUENCE: 23

Lys Leu Ala Lys Leu Ala Lys Lys Leu Ala Lys Leu Ala Lys
1               5                   10

<210> SEQ ID NO 24
<211> LENGTH: 27
<212> TYPE: PRT
<213> ORGANISM: Artificial Sequence
<220> FEATURE:
<223> OTHER INFORMATION: Synthetic peptide

<400> SEQUENCE: 24

Gly Ala Leu Phe Leu Gly Phe Leu Gly Ala Ala Gly Ser Thr Asn Gly
1               5                   10                  15

Ala Trp Ser Gln Pro Lys Lys Lys Arg Lys Val
            20                  25

<210> SEQ ID NO 25
<211> LENGTH: 21
<212> TYPE: PRT
<213> ORGANISM: Artificial Sequence
<220> FEATURE:
<223> OTHER INFORMATION: Synthetic peptide

<400> SEQUENCE: 25

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 26
<211> LENGTH: 23
<212> TYPE: PRT
<213> ORGANISM: Artificial Sequence
<220> FEATURE:
<223> OTHER INFORMATION: Synthetic peptide

<400> SEQUENCE: 26

Gly Ala Leu Phe Leu Gly Trp Leu Gly Ala Ala Gly Ser Thr Met Gly
1               5                   10                  15

Ala Lys Lys Lys Arg Lys Val
            20

<210> SEQ ID NO 27
<211> LENGTH: 23

```
<212> TYPE: PRT
<213> ORGANISM: Artificial Sequence
<220> FEATURE:
<223> OTHER INFORMATION: Synthetic peptide

<400> SEQUENCE: 27

Met Gly Leu Gly Leu His Leu Leu Val Leu Ala Ala Ala Leu Gln Gly
1               5                   10                  15

Ala Lys Ser Lys Arg Lys Val
            20

<210> SEQ ID NO 28
<211> LENGTH: 26
<212> TYPE: PRT
<213> ORGANISM: Artificial Sequence
<220> FEATURE:
<223> OTHER INFORMATION: Synthetic peptide

<400> SEQUENCE: 28

Ala Ala Val Ala Leu Leu Pro Ala Val Leu Leu Ala Leu Leu Ala Pro
1               5                   10                  15

Ala Ala Ala Asn Tyr Lys Lys Pro Lys Leu
            20                  25

<210> SEQ ID NO 29
<211> LENGTH: 28
<212> TYPE: PRT
<213> ORGANISM: Artificial Sequence
<220> FEATURE:
<223> OTHER INFORMATION: Synthetic peptide

<400> SEQUENCE: 29

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 30
<211> LENGTH: 24
<212> TYPE: PRT
<213> ORGANISM: Artificial Sequence
<220> FEATURE:
<223> OTHER INFORMATION: Synthetic peptide

<400> SEQUENCE: 30

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 31
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (24)..(24)
<223> OTHER INFORMATION: Xaa can be any naturally occurring amino acid

<400> SEQUENCE: 31

Asp Pro Lys Gly Asp Pro Lys Gly Val Thr Val Thr Val Thr Val Thr
1               5                   10                  15

Val Thr Gly Lys Gly Asp Pro Xaa Pro Asp
```

```
                20                  25

<210> SEQ ID NO 32
<211> LENGTH: 14
<212> TYPE: PRT
<213> ORGANISM: Artificial Sequence
<220> FEATURE:
<223> OTHER INFORMATION: Synthetic peptide

<400> SEQUENCE: 32

Pro Pro Pro Pro Pro Pro Pro Pro Pro Pro Pro Pro Pro Pro
1               5                   10

<210> SEQ ID NO 33
<211> LENGTH: 18
<212> TYPE: PRT
<213> ORGANISM: Artificial Sequence
<220> FEATURE:
<223> OTHER INFORMATION: Synthetic peptide

<400> SEQUENCE: 33

Val Arg Leu Pro Pro Pro Val Arg Leu Pro Pro Pro Val Arg Leu Pro
1               5                   10                  15

Pro Pro

<210> SEQ ID NO 34
<211> LENGTH: 10
<212> TYPE: PRT
<213> ORGANISM: Artificial Sequence
<220> FEATURE:
<223> OTHER INFORMATION: Synthetic peptide

<400> SEQUENCE: 34

Pro Arg Pro Leu Pro Pro Pro Arg Pro Gly
1               5                   10

<210> SEQ ID NO 35
<211> LENGTH: 30
<212> TYPE: PRT
<213> ORGANISM: Artificial Sequence
<220> FEATURE:
<223> OTHER INFORMATION: Synthetic peptide

<400> SEQUENCE: 35

Ser Val Arg Arg Arg Pro Arg Pro Pro Tyr Leu Pro Arg Pro Arg Pro
1               5                   10                  15

Pro Pro Phe Phe Pro Pro Arg Leu Pro Pro Arg Ile Pro Pro
            20                  25                  30

<210> SEQ ID NO 36
<211> LENGTH: 21
<212> TYPE: PRT
<213> ORGANISM: Artificial Sequence
<220> FEATURE:
<223> OTHER INFORMATION: Synthetic peptide

<400> SEQUENCE: 36

Thr Arg Ser Ser Arg Ala Gly Leu Gln Phe Pro Val Gly Arg Val His
1               5                   10                  15

Arg Leu Leu Arg Lys
            20

<210> SEQ ID NO 37
<211> LENGTH: 23
<212> TYPE: PRT
```

<213> ORGANISM: Artificial Sequence
<220> FEATURE:
<223> OTHER INFORMATION: Synthetic peptide

<400> SEQUENCE: 37

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 38
<211> LENGTH: 37
<212> TYPE: PRT
<213> ORGANISM: Artificial Sequence
<220> FEATURE:
<223> OTHER INFORMATION: Synthetic peptide

<400> SEQUENCE: 38

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
            20                  25                  30

Thr Gln Ile Ala Lys
        35

<210> SEQ ID NO 39
<211> LENGTH: 28
<212> TYPE: PRT
<213> ORGANISM: Artificial Sequence
<220> FEATURE:
<223> OTHER INFORMATION: Synthetic peptide

<400> SEQUENCE: 39

Ala Leu Trp Met Thr Leu Leu Lys Lys Val Leu Lys Ala Ala Ala Lys
1               5                   10                  15

Ala Ala Leu Asn Ala Val Leu Val Gly Ala Asn Ala
            20                  25

<210> SEQ ID NO 40
<211> LENGTH: 26
<212> TYPE: PRT
<213> ORGANISM: Artificial Sequence
<220> FEATURE:
<223> OTHER INFORMATION: Synthetic peptide

<400> SEQUENCE: 40

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 41
<211> LENGTH: 14
<212> TYPE: PRT
<213> ORGANISM: Artificial Sequence
<220> FEATURE:
<223> OTHER INFORMATION: Synthetic peptide

<400> SEQUENCE: 41

Ile Asn Leu Lys Ala Leu Ala Ala Leu Ala Lys Lys Ile Leu
1               5                   10

<210> SEQ ID NO 42
<211> LENGTH: 33

```
<212> TYPE: PRT
<213> ORGANISM: Artificial Sequence
<220> FEATURE:
<223> OTHER INFORMATION: Synthetic peptide

<400> SEQUENCE: 42

Gly Phe Phe Ala Leu Ile Pro Lys Ile Ile Ser Ser Pro Leu Pro Lys
1               5                   10                  15

Thr Leu Leu Ser Ala Val Gly Ser Ala Leu Gly Gly Ser Gly Gly Gln
            20                  25                  30

Glu

<210> SEQ ID NO 43
<211> LENGTH: 15
<212> TYPE: PRT
<213> ORGANISM: Artificial Sequence
<220> FEATURE:
<223> OTHER INFORMATION: Synthetic peptide

<400> SEQUENCE: 43

Leu Ala Lys Trp Ala Leu Lys Gln Gly Phe Ala Lys Leu Lys Ser
1               5                   10                  15

<210> SEQ ID NO 44
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(23)
<223> OTHER INFORMATION: Xaa can be any naturally occurring amino acid

<400> SEQUENCE: 44

Ser Met Ala Gln Asp Ile Ile Ser Thr Ile Gly Asp Leu Val Lys Trp
1               5                   10                  15

Ile Ile Gln Thr Val Asn Xaa Phe Thr Lys Lys
            20                  25

<210> SEQ ID NO 45
<211> LENGTH: 41
<212> TYPE: PRT
<213> ORGANISM: Artificial Sequence
<220> FEATURE:
<223> OTHER INFORMATION: Synthetic peptide

<400> SEQUENCE: 45

Leu Leu Gly Asp Phe Phe Arg Lys Ser Lys Glu Lys Ile Gly Lys Glu
1               5                   10                  15

Phe Lys Arg Ile Val Gln Arg Ile Lys Gln Arg Ile Lys Asp Phe Leu
            20                  25                  30

Ala Asn Leu Val Pro Arg Thr Glu Ser
        35                  40

<210> SEQ ID NO 46
<211> LENGTH: 20
<212> TYPE: PRT
<213> ORGANISM: Artificial Sequence
<220> FEATURE:
<223> OTHER INFORMATION: Synthetic peptide

<400> SEQUENCE: 46

Leu Lys Lys Leu Leu Lys Lys Leu Leu Lys Lys Leu Leu Lys Lys Leu
1               5                   10                  15
```

```
<210> SEQ ID NO 47
<211> LENGTH: 18
<212> TYPE: PRT
<213> ORGANISM: Artificial Sequence
<220> FEATURE:
<223> OTHER INFORMATION: Synthetic peptide

<400> SEQUENCE: 47

Lys Leu Lys Leu Lys Leu Lys Leu Lys Leu Lys Leu Lys Leu Lys Leu
1               5                   10                  15

Lys Leu

<210> SEQ ID NO 48
<211> LENGTH: 18
<212> TYPE: PRT
<213> ORGANISM: Artificial Sequence
<220> FEATURE:
<223> OTHER INFORMATION: Synthetic peptide

<400> SEQUENCE: 48

Pro Ala Trp Arg Lys Ala Phe Arg Trp Ala Trp Arg Met Leu Lys Lys
1               5                   10                  15

Ala Ala

<210> SEQ ID NO 49
<211> LENGTH: 23
<212> TYPE: DNA
<213> ORGANISM: Artificial Sequence
<220> FEATURE:
<223> OTHER INFORMATION: Synthetic primer

<400> SEQUENCE: 49
gaaaggagag aagtttggag ccc                                        23

<210> SEQ ID NO 50
<211> LENGTH: 20
<212> TYPE: DNA
<213> ORGANISM: Artificial Sequence
<220> FEATURE:
<223> OTHER INFORMATION: Synthetic primer

<400> SEQUENCE: 50
gctgttcttc tggttgccgc                                            20

<210> SEQ ID NO 51
<211> LENGTH: 24
<212> TYPE: DNA
<213> ORGANISM: Artificial Sequence
<220> FEATURE:
<223> OTHER INFORMATION: Synthetic primer

<400> SEQUENCE: 51
ccctggtggt gtgttctgta ttgg                                       24

<210> SEQ ID NO 52
<211> LENGTH: 23
<212> TYPE: DNA
<213> ORGANISM: Artificial Sequence
<220> FEATURE:
<223> OTHER INFORMATION: Synthetic primer

<400> SEQUENCE: 52
```

(Leu Lys Lys Leu appears above with position 20 marker)

```
tggcaaggga aatatcacac agc                                              23

<210> SEQ ID NO 53
<211> LENGTH: 19
<212> TYPE: DNA
<213> ORGANISM: Artificial Sequence
<220> FEATURE:
<223> OTHER INFORMATION: Synthetic peptide

<400> SEQUENCE: 53
ggatgcatag gactcagat                                                   19

<210> SEQ ID NO 54
<211> LENGTH: 19
<212> TYPE: DNA
<213> ORGANISM: Artificial Sequence
<220> FEATURE:
<223> OTHER INFORMATION: Synthetic primer

<400> SEQUENCE: 54
gcagttcaaa cagctctat                                                   19

<210> SEQ ID NO 55
<211> LENGTH: 20
<212> TYPE: DNA
<213> ORGANISM: Artificial Sequence
<220> FEATURE:
<223> OTHER INFORMATION: Synthetic primer

<400> SEQUENCE: 55
cctcgacctg ttcatgttgt                                                  20

<210> SEQ ID NO 56
<211> LENGTH: 19
<212> TYPE: DNA
<213> ORGANISM: Artificial Sequence
<220> FEATURE:
<223> OTHER INFORMATION: Synthetic primer

<400> SEQUENCE: 56
gtattagcat gtccgtgga                                                   19
```